US006936714B2

(12) United States Patent
Danishefsky et al.

(10) Patent No.: US 6,936,714 B2
(45) Date of Patent: Aug. 30, 2005

(54) COMPOUNDS OF THE SAFRAMYCIN-ECTEINASCIDIN SERIES, USES, AND SYNTHESIS THEREOF

(75) Inventors: Samuel J. Danishefsky, Englewood, NJ (US); Bishan Zhou, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/728,580

(22) Filed: Dec. 5, 2003

(65) Prior Publication Data

US 2004/0127709 A1 Jul. 1, 2004

Related U.S. Application Data

(62) Division of application No. 09/765,515, filed on Jan. 19, 2001, now Pat. No. 6,686,470.
(60) Provisional application No. 60/177,071, filed on Jan. 19, 2000.

(51) Int. Cl.$^7$ ........................................... C07D 471/14
(52) U.S. Cl. ..................................................... 544/342
(58) Field of Search ......................................... 544/342

(56) References Cited

U.S. PATENT DOCUMENTS

| 5,721,362 A | 2/1998 | Corey |
| 6,124,292 A | 9/2000 | Corey |
| 6,348,467 B1 | 2/2002 | Corey |
| 6,686,470 B2 | 2/2004 | Danishefsky |
| 6,809,099 B2 * | 10/2004 | Myers et al. ............... 514/250 |
| 2003/0008873 A1 * | 1/2003 | Myers et al. ............... 514/249 |

FOREIGN PATENT DOCUMENTS

| WO | WO 9951238 | 10/1999 |
| WO | WO 0018233 | 4/2000 |

OTHER PUBLICATIONS

Arai T. et al., "New antibiotics saframycins A, B, C, D and E," *J Antibiot. (Tokyo)* 1977, vol. 30, No. 11, p.p. 1015–1018.
Bobbitt, J. et al., "Isoquinolines. III. A New Synthesis of 1,2,3,4–tetrahydro isoquinolines," *J. Org. Chem.* 1965, vol. 30, p.p. 2247–2250.
Cabre–Castellvi, J. et al., "Convenient Synthesis of Carboxilic Acid Anhydrides using N,N–Bis[2–oxo–3–oxazol idinyl]phosphorodiamidic Chloride," *Synthesis* 1981, No. 7, p.p. 616–620.
Caldwell C. et al., "Synthesis of the Lipophilic Side Chain of the Cyclic Hexa–depsipeptide Antibiotic L–156, 602," *J. Org. Chem.* 1990, vol. 44, p.p. 2355–2361.

Caron, M. et al., "Highly Enantioselective Solvolyses of L– and D–Phenylalanine p–Nitrophenyl Esters by an L–Histidyl Dipeptide in Surfacant Coaggregates Formed by Cholesterol–Containing Amphiphiles," *J. Org. Chem.* 1988, vol. 53, No. 21, p.p. 5187–5189.
Corey, E. et al., "Enantioselective Total Synthesis of Ecteinacidin 743," *J. Am. Chem. Soc.* 1996, vol. 118, p.p. 9202–9203.
Danishefsky, S. et al., "Total synthesis of Quinocarcinol Methyl Ester," *J. Am. Chem. Soc.* 1985, vol. 107, No. 5, p.p. 1421–1423.
Fukuyama, T. et al., "Total Synthesis of(±) Saframycin A," *J. Am. Chem. Soc.* 1990, vol. 112, No. 8, p.p. 3712–3713.
Fukuyama, T. et al., "A Sterocontrolled Total Synthesis of (±) Reniramycin A," *Tetrahedron Lett.* 1990, vol. 31, No. 42, p.p. 5989–5992.
Fukuyama, T. et al., "Stereocontrolled total Synthesis of (±) Saframycin B," *J. Am. Chem. Soc.* 1982, vol. 104, No. 118, p.p. 4957–4958.

(Continued)

*Primary Examiner*—Emily Bernhardt
(74) *Attorney, Agent, or Firm*—John P. White, Esq.; Cooper & Dunham LLP

(57) ABSTRACT

Compounds of the saframycin-ecteinascidin series with cytotoxic properties having the following general formula, their uses and synthesis, are disclosed:

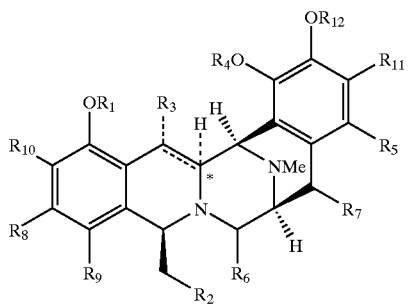

wherein $R_1$ and $R_4$ is H, a $C_1$ to $C_4$ alkyl group, or an acyl group;
wherein $R_2$ is an ether, ester, amide, or a phthalimide group;
wherein $R_3$ is =O, OH, an ether group, an acyl group such as OC(O)Me, OC(O)Bn and OC(O)Et, or a sulfide group; wherein $R_5$ is H, halogen, OH, an ether group, an acyl group, or an amide group; wherein $R_6$ is =O, OH, OCH$_3$, CN, or an acyloxy group;
wherein $R_7$, is =O, OH, halogen, an ether group, or an acyl group; wherein $R_8$ and $R_9$ are independently H, CH$_3$, OCH$_3$, OC$_2$H$_5$, CF$_3$, halogen such as Br and F, or $R_8$ and $R_9$ are joined together as a methylenedioxy group, or other five or six membered ring; wherein $R_{10}$ and $R_{11}$ are independently CH$_3$, OCH$_3$, OC$_2$H$_5$, SCH$_3$, or SC$_2$H$_5$; wherein $R_{12}$ is H, a $C_1$ to $C_4$ alkyl group, or an acyl group; and wherein the chiral center marked * has the R or the S configuration.

43 Claims, 22 Drawing Sheets

OTHER PUBLICATIONS

Gao, Y. et al., "Catalytic Asymmetric Epoxidation and Kinetic Resolution: Modified Procedures Including in Situ Derivatization," *J. Am. Chem. Soc.* 1987, vol. 109, No. 18, p.p. 5765–5780.

Guan, Y. et al., "Molecular and crystal structures of ecteinascidins: potent antitumor compounds from the Caribbean tunicate Ecteinascidia tur binata," *J. Biomol Struct. Dyn.* 1993, vol. 10, No. 5, p.p. 793–817.

Kishi, K. et al., "Structure–activity relationships of saframycins," *J Antibiot. (Tokyo)* 1984, vol. 37, No. 8, p.p. 847–852.

Kitahara, Y. et al., "Synthesis of 4,7–Indolequinones. The Oxidative Demethylation of 4,7 Dimethoxyindoles with Ceric Ammonium Nitrate," *Chem. Phar. Bull. (Japan)* 1985, vol. 33, No. 5, p.p. 2122–2128.

Kubo, A. et al., "Stereoselective total Synthesis of (±) Saframycin B," *J. Org. Chem.* 1988, vol. 53, No. 18, p.p. 4295–4310.

Martinez, E. et al., "Phthalascidin, a synthetic antitumor agent with potency and mode of action comparable to ecteinacidin 743," *Proc. Natl. Acad. Sci.* 1999, vol. 96, p.p. 3496–3501.

Medina, E. et al., "Enantioselective synthesis of N–Boc–1–naphthylglycine," *Tetrahedron Asym.* 1997, vol. 8, No. 10, p.p. 1581–1586.

Mikami, Y. et al., "Saframycin S, a new saframycin group antibiotic," *J. Pharmacobiodyn.* 1981, No. 4, p.p. 282–286.

Myers, A. et al. "A concise, Stereocontrolled Synthesis of (−) Saframycin A by the Directed Condensation of a–Amino Aldehyde Precursors," *J. Am. Chem. Soc.* 1999, vol. 121, No. 43, p.p. 10828–10829.

Sakai, R. et al., "Additional antitumor ecteinacidins from a Caribbean tunicate: Crystal structures and activites in vivo," *Proc. Natl. Acad. Sci.* 1992, vol. 89, p.p. 11456–11460.

Sakai, R. et al., "Ecteinascidins: Putative Biosynthetic Precursors and Absolute Stereochemistry," *J. Am. Chem. Soc.* 1996, vol. 118, No. 35, p.p. 9017–9023.

Sharpless, K. B. et al., "The Osmium–Catalyzed Asymmetric Dihydroxylation: A New Ligand Class and a Process Improvement," *J. Org. Chem.* 1992, vol., 57, No. 6, p.p. 2768–2771.

Zhou et al., "A novel face specific Mannich closure providing access to the saframycin–ecteinascidin series of piperazine based alkaloids," *Tetrahedron Letters* 2000, vol. 41, p.p. 2043–2046.

Zhou et al., "Synthetic explorations in the saframycin ecteinascidin series: construction of major chiral subunits through catalytic asymmetric induction," *Tetrahedron Letters* 2000, vol. 41, p.p. 2039–2042.

* cited by examiner

FIGURE 2

| Cell lines, $IC_{50}$ (ng/mL) | | Synthesis inhibition $IC_{50}$ (µg/mL) | |
|---|---|---|---|
| P 388 | 0.2 | Prot | >1 |
| A 549 | 0.2 | | |
| HT 29 | 0.5 | DNA | 0.1 |
| MEL 28 | 5.0 | RNA | 0.03 |
| CV-1 | 1.0 | | |

High regioselectivity and unexpected low stereoselectivity for the azide-opening step:

COMPOUNDS OF THE SAFRAMYCIN-ECTEINASCIDIN SERIES, USES, AND SYNTHESIS THEREOF

This application is a divisional of U.S. Ser. No. 09/765,515, filed Jan. 19, 2001, now U.S. Pat. No. 6,686,470 B2, issued Feb. 3, 2004 to Danishefsky, et al., claiming priority of U.S. Provisional Application No. 60/177,071, filed Jan. 19, 2000.

This invention has been made with government support under National Institutes of Health Grant Nos. CA-28824 and HL-25848. Accordingly, the U.S. Government may have certain rights in the invention.

Throughout this application, various publications may be referenced by Arabic numerals in brackets. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

FIELD OF INVENTION

The disclosed invention relates to novel compounds of the saframycin-ecteinascidin series having cytotoxic properties and to schemes for the total synthesis of such compounds.

BACKGROUND OF THE INVENTION

The screening of natural product sources for new drug candidates with useful therapeutic margins has led to a variety of novel structures. One of the most fascinating and promising of these is ecteinascidin 743 (ET 743) derived from the marine tunicate Ecteinascidia turbinata. (1) The novel structure of Et 743, its difficult availability, and its exceedingly potent cytotoxicity render it an attractive target for total synthesis. This goal was undertaken and accomplished in a most interesting fashion by E. J. Corey and coworkers. (2) Follow-up studies by Corey, Schreiber (3) and co-workers resulted in the demonstration that a significantly simplified version of ET 743 (ie: phthalascidin) retains the cytotoxicity of the natural product. Previously, well before the ecteinascidins were known, some of the named inventors had accomplished what was then the only total synthesis of quinocarcinol.(4) The central Mannich-like envelopment strategy, learned from work in the quinocarcin series, was adapted to the ET problem.

While ET 743 was previously known, the total synthesis of ET 743 was first accomplished by Corey in 1996 and, prior to this invention, was the only total synthesis of an ecteinascidin.

It is known that saframycin B, saframycin A (13,14), saframycin S (15), ecteinascidin 729 (Et 729)(16), Et 743 and Phthalascidin (3) all posses cytotoxic antitumor and antibiotic characteristics. It is also known that saframycin S, saframycin B, saframycin A, Et 729, Et 743 (17), and phthalascidin (3) all possess a two tetrahydroisoquinoline aromatic carbon nitrogen framework. Saframycins and ecteinascidins have been shown to interact with DNA. Interactions are believed to occur between DNA and the tetrahydroisoquinoline aromatic carbon nitrogen framework. (2,18)

SUMMARY OF THE INVENTION

The subject invention provides compounds of the saframycin-ecteinascidin series with cytotoxic properties having the following general formula, their uses and synthesis:

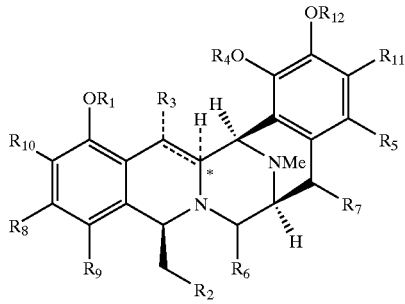

wherein $R_1$ and $R_4$ is H, a $C_1$ to $C_4$ alkyl group, or an acyl group;
wherein $R_2$ is an ether, ester, amide, a phthalimide group, a substituted phthalimide group or is covalently bound to $R_6$;
wherein $R_3$ is =O, OH, an ether group, an acyl group such as OC(O)Me, OC(O)Bn and OC(O)Et, or a sulfide group; wherein $R_5$ is H, halogen, OH, an ether group, an acyl group, or an amide group; wherein $R_6$ is =O, OH, OCH$_3$, CN, or an acyloxy group or is covalently bound to $R_2$; wherein $R_7$, is =O, OH, halogen, an ether group, or an acyl group; wherein $R_8$ and $R_9$ are independently H, CH$_3$, OCH$_3$, OC$_2$H$_5$, CF$_3$, halogen such as Br and F, or $R_8$ and $R_9$ are joined together as a methylenedioxy group, or other five or six membered ring; wherein $R_{10}$ and $R_{11}$ are independently CH$_3$, OCH$_3$, OC$_2$H$_5$, SCH$_3$, or SC$_2$H$_5$; wherein $R_{12}$ is H, a $C_1$ to $C_4$ alkyl group, or an acyl group; and wherein the chiral center marked * has the R or the S configuration.

The subject invention also provides for a group of saframycin-ecteinascidin series compounds with cytotoxic properties having the following general formula, their uses and synthesis:

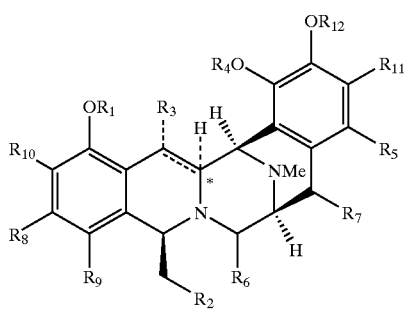

wherein $R_1$ and $R_4$ is H, a $C_1$ to $C_4$ alkyl group, or an acyl group;
wherein $R_2$ is an ether, ester, amide, an aromatic group or is covalently bound to $R_6$; wherein $R_3$ is =O, OH, an ether group, an acyl group such as OC(O)Me, OC(O)Bn and OC(O)Et, a sulfide group or H; wherein $R_5$ is H, halogen, OH, an ether group, an acyl group, or an amide group; wherein $R_6$ is =O, OH, OCH$_3$, CN, or an acyloxy group or is covalently bound to $R_2$; wherein $R_7$, is =O, OH, halogen, an ether group, or an acyl group; wherein $R_8$ and $R_9$ are independently H, CH$_3$, OCH$_3$, OC$_2$H$_5$, CF$_3$, halogen such as Br and F, or $R_8$ and $R_9$ are joined together as a methylenedioxy group, or other five or six membered ring; wherein $R_{10}$ and $R_{11}$ are independently CH$_3$, OCH$_3$, $OC_2H_5$, $SCH_3$, or $SC_2H_5$; wherein $R_{12}$ is H, a $C_1$ to $C_4$ alkyl group, or an acyl group; and wherein the chiral center marked * has the R or the S configuration.

DESCRIPTION OF THE FIGURES

FIG. 2 is a Table showing the cytotoxicity, antimetabolism and antimicrobial activity of ET 743.

DETAILED DESCRIPTION OF THE INVENTION

Figure 1:
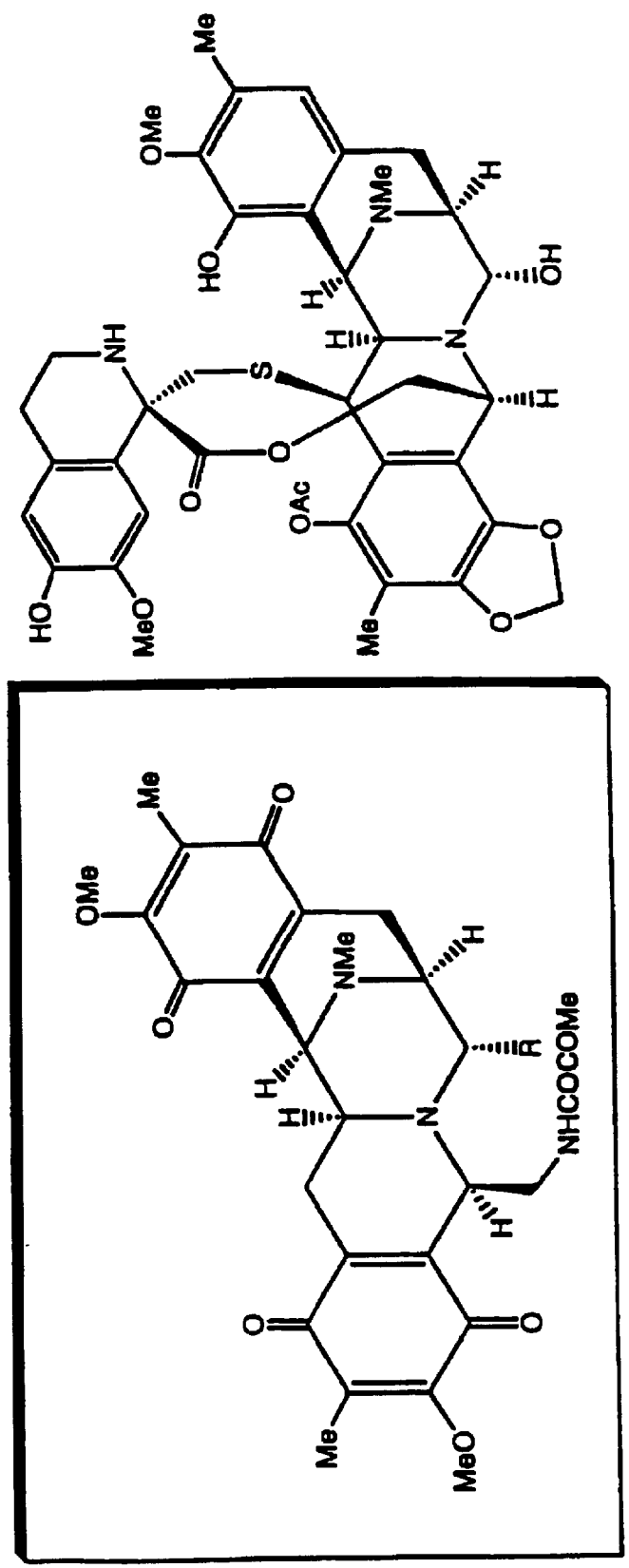
FIG. 1 shows the structures of Saframycin B and Ecteinascidin 743.
Figure 3:
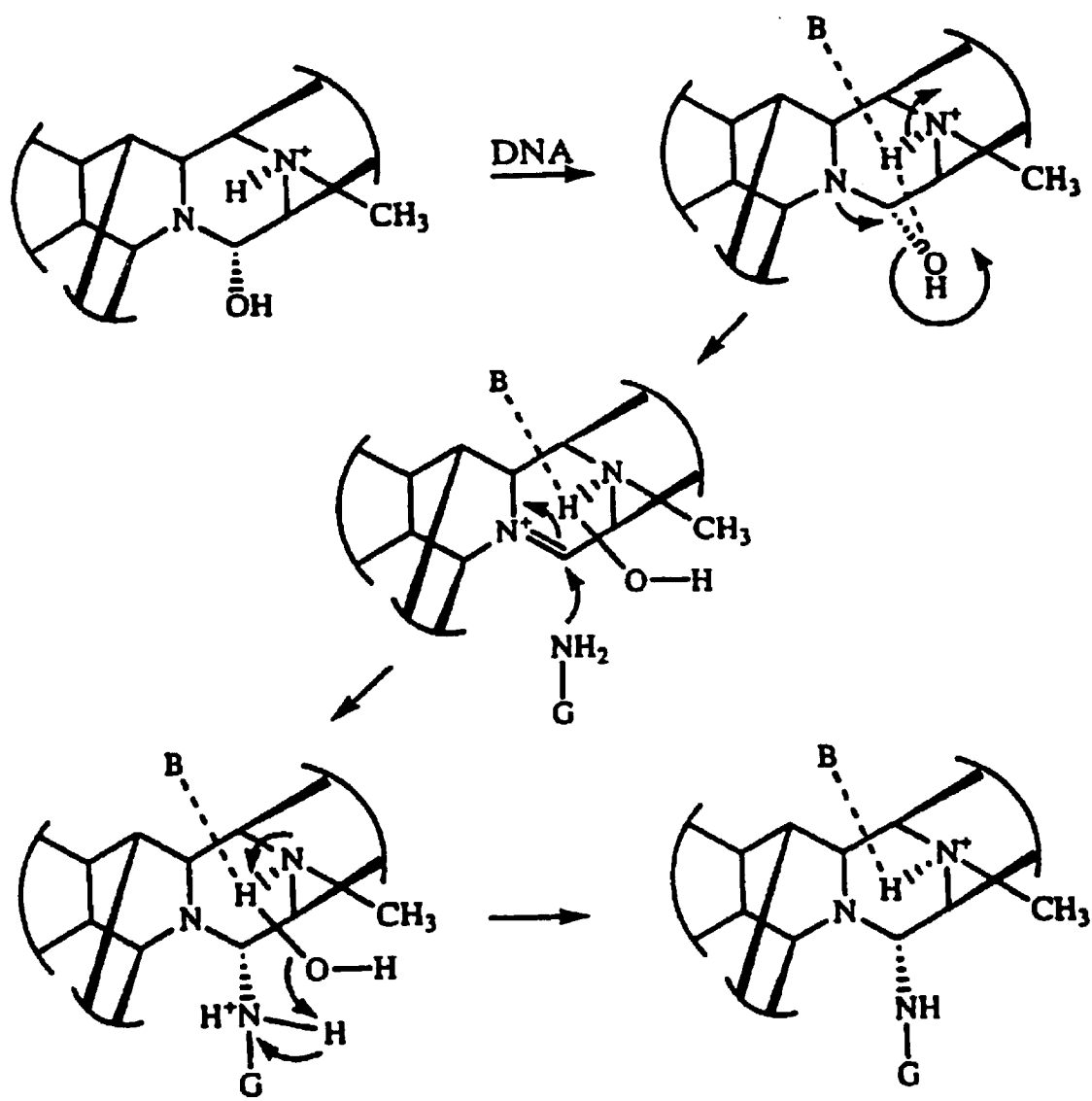
FIG. 3 shows the mechanism for the catalytic activation of ET 743 and alkylation of 6GN2.
Figure 4A:
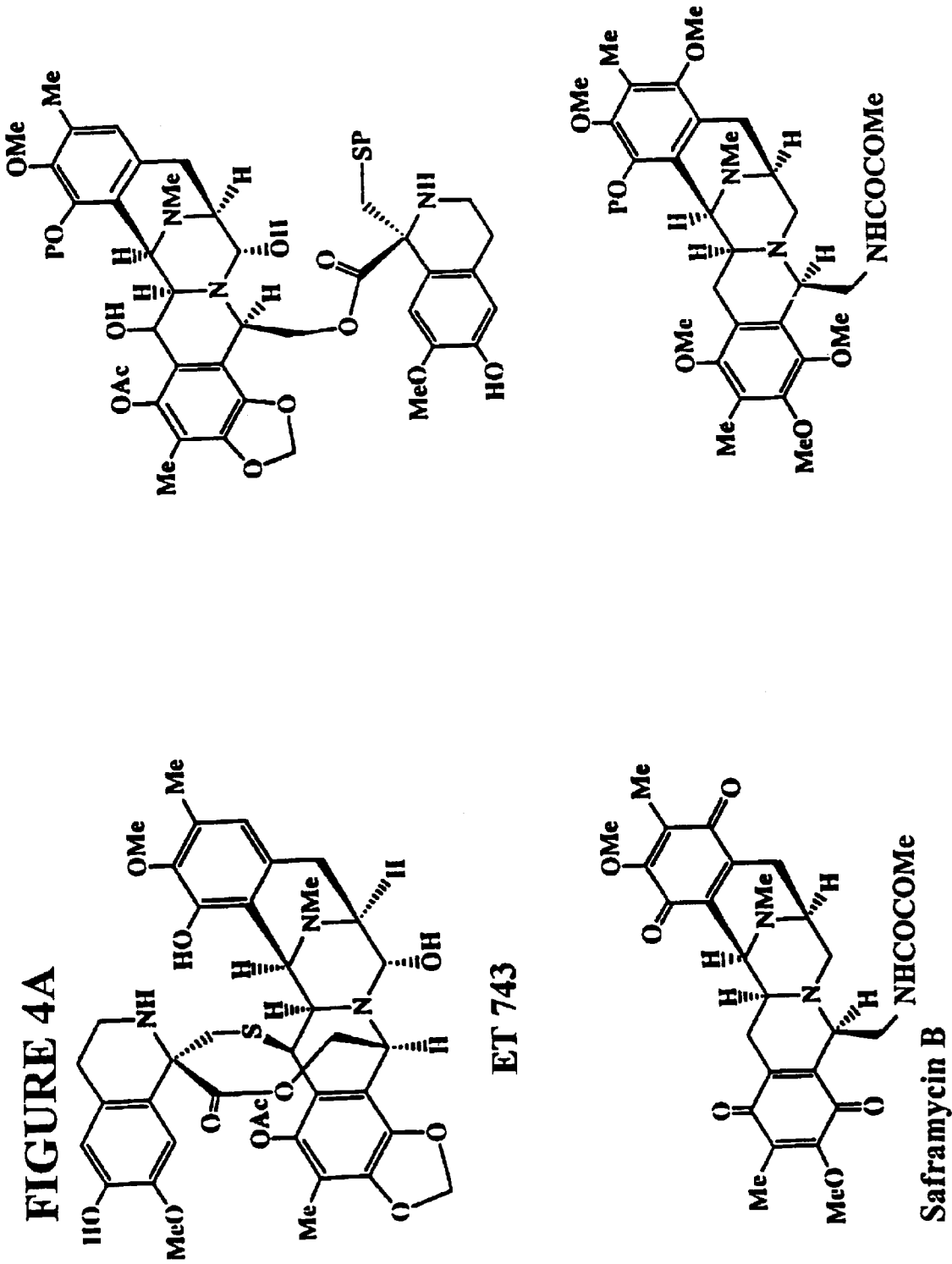
FIGS. 4A, 4B and 4C show the retrosynthesis analysis of ET 743 and Saframycin B.
Figure 4B:
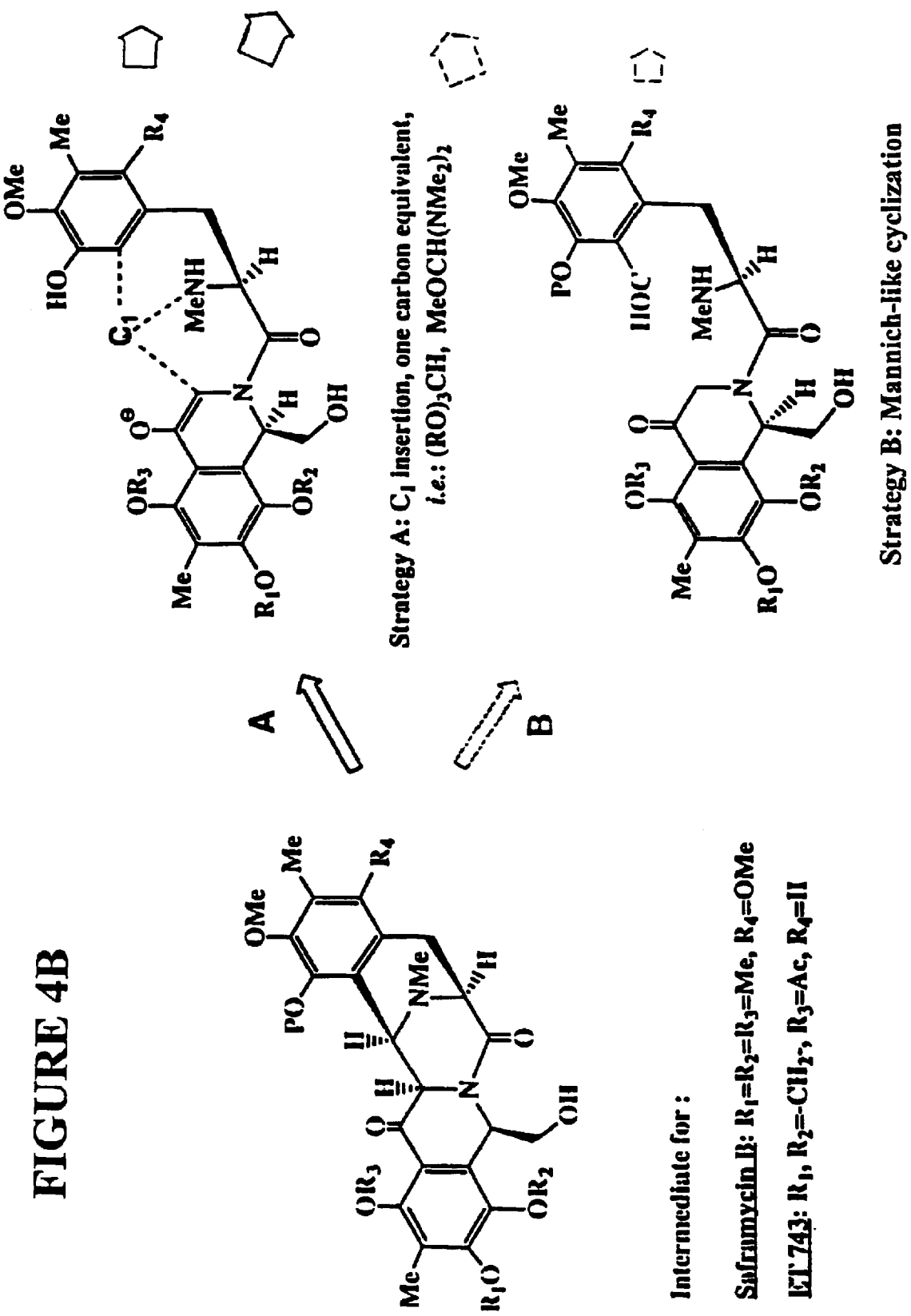
Figure 4C:
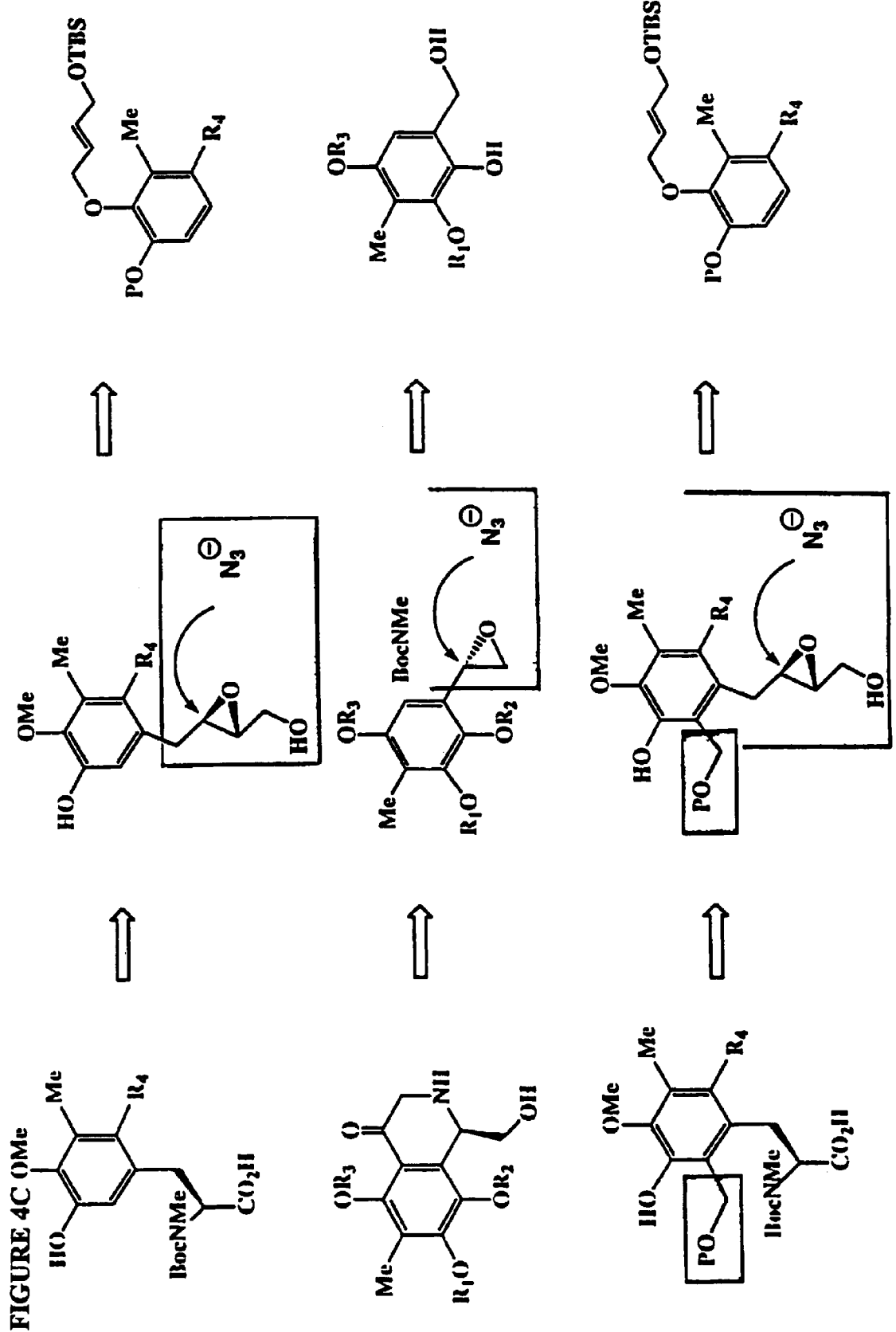
Figure 5A:
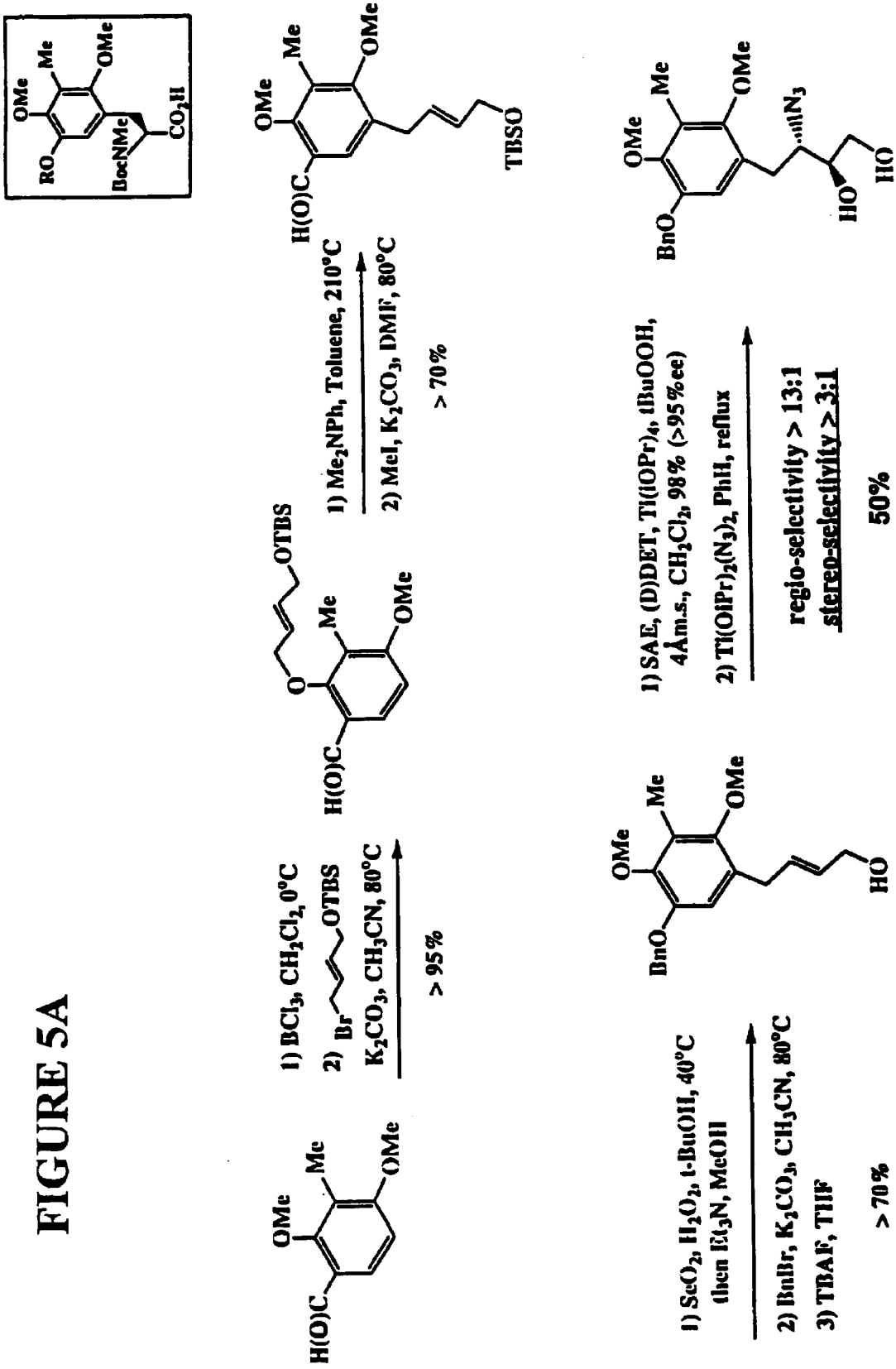
FIGS. 5A and 5B show the enantioselective synthesis of amino acid for the synthesis strategy A of Saframycin B.
Figure 5B:
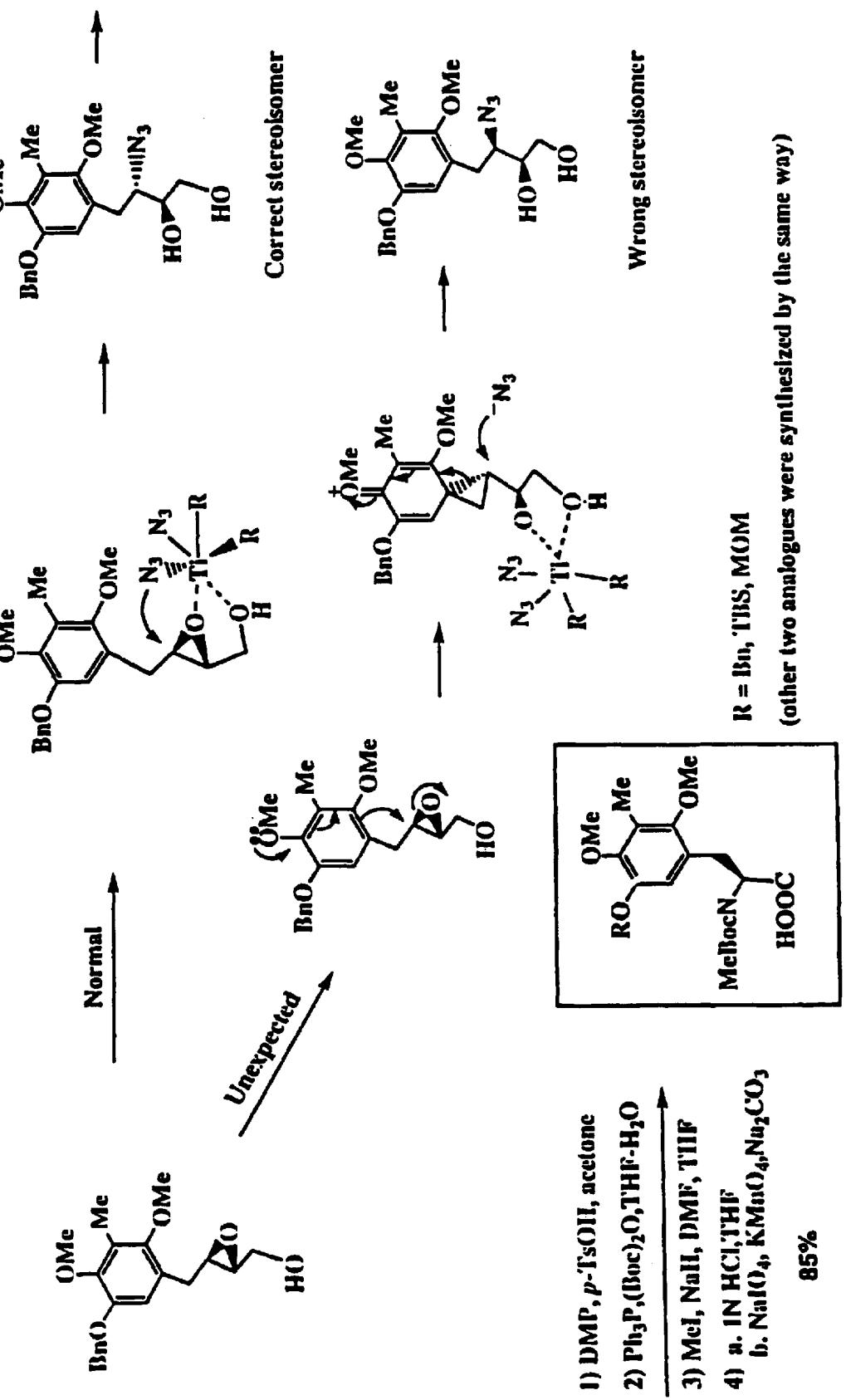
Figure 6:
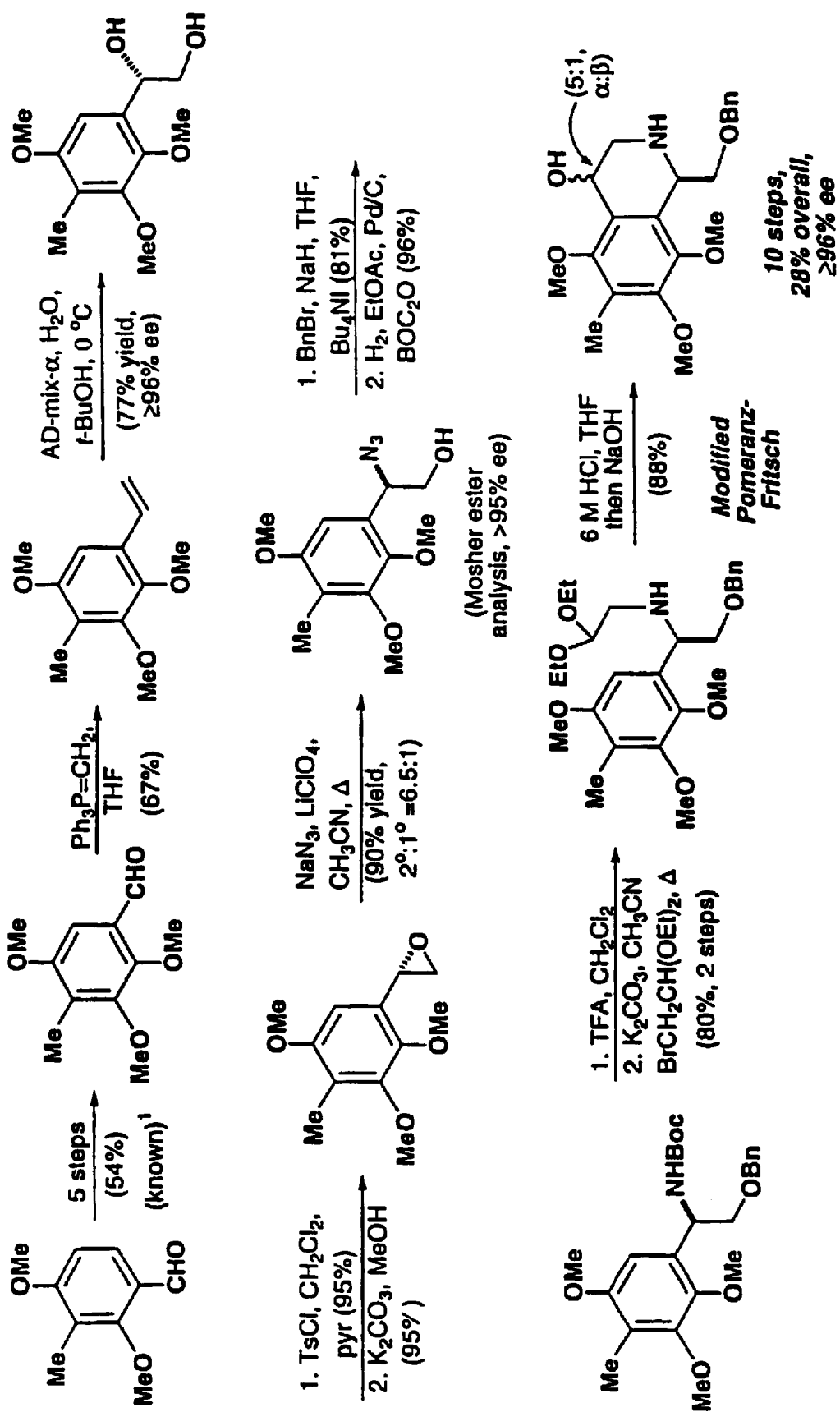
FIG. 6 shows the enantioselective synthesis of tertahydroisoquinoline, which is used as a subunit in the foregoing synthesis.
Figure 7A:
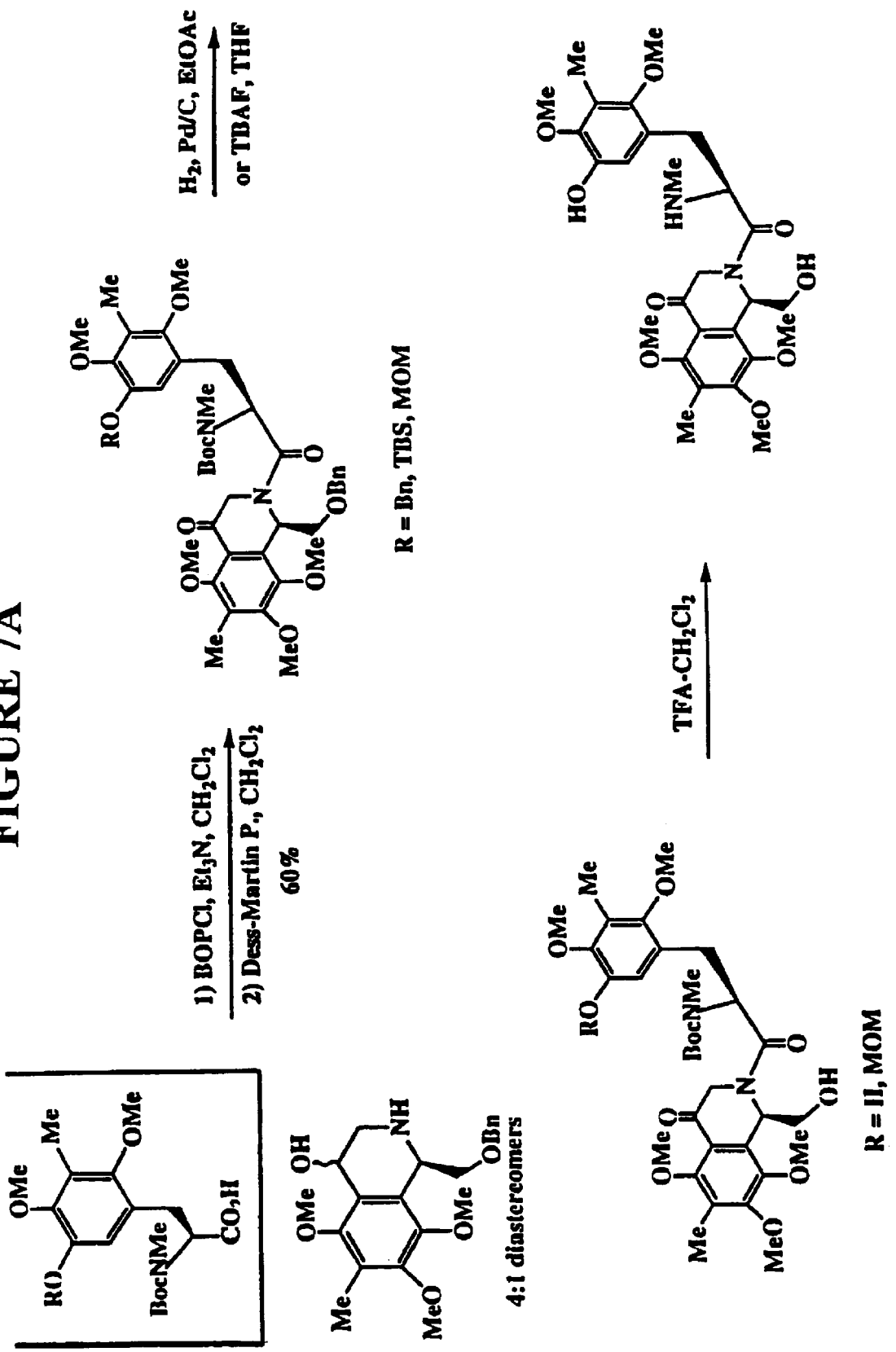
FIGS. 7A and 7B show the coupling strategy for the synthesis strategy A of Saframycin B.
Figure 7B:
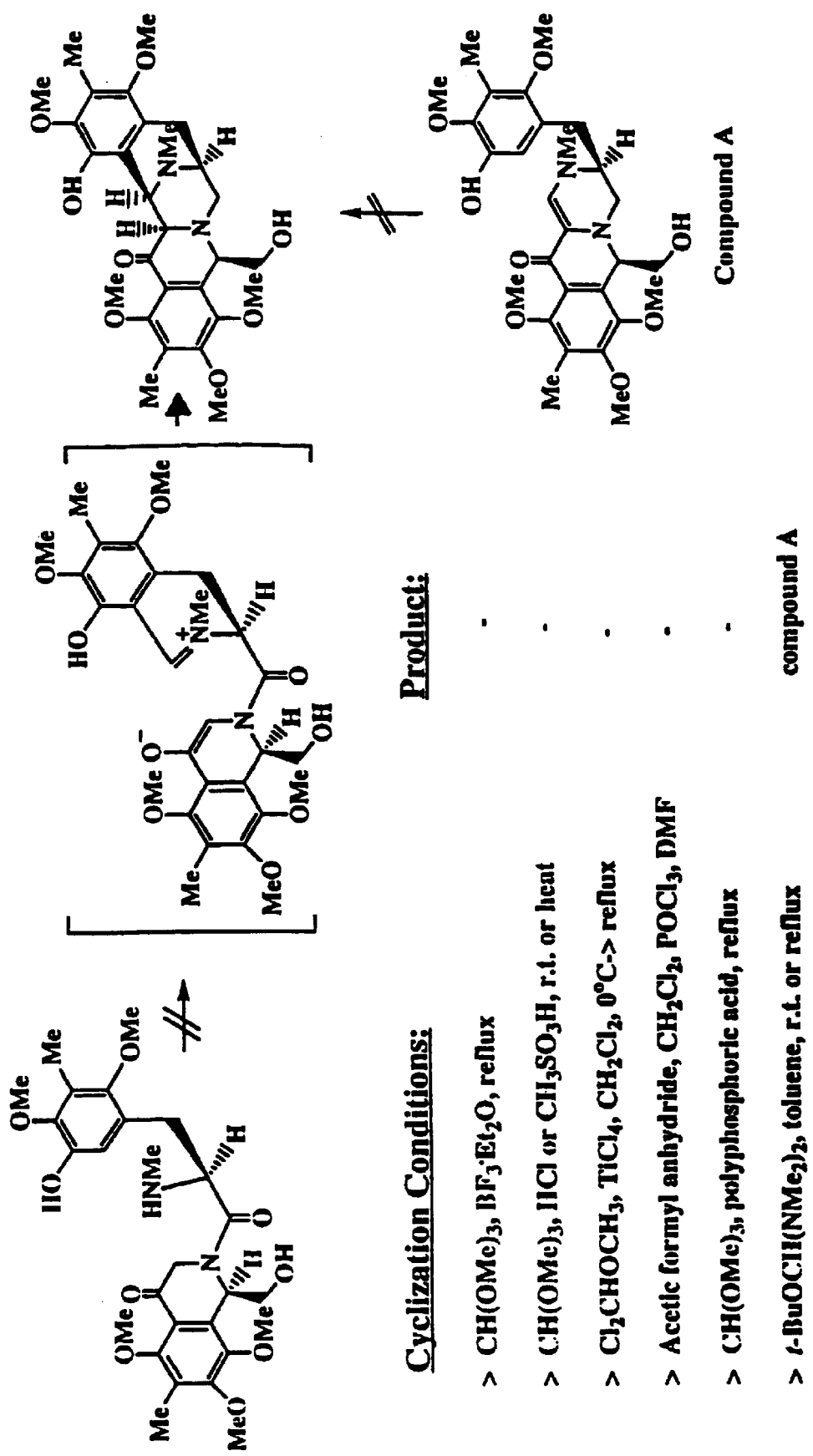
Figure 8A:
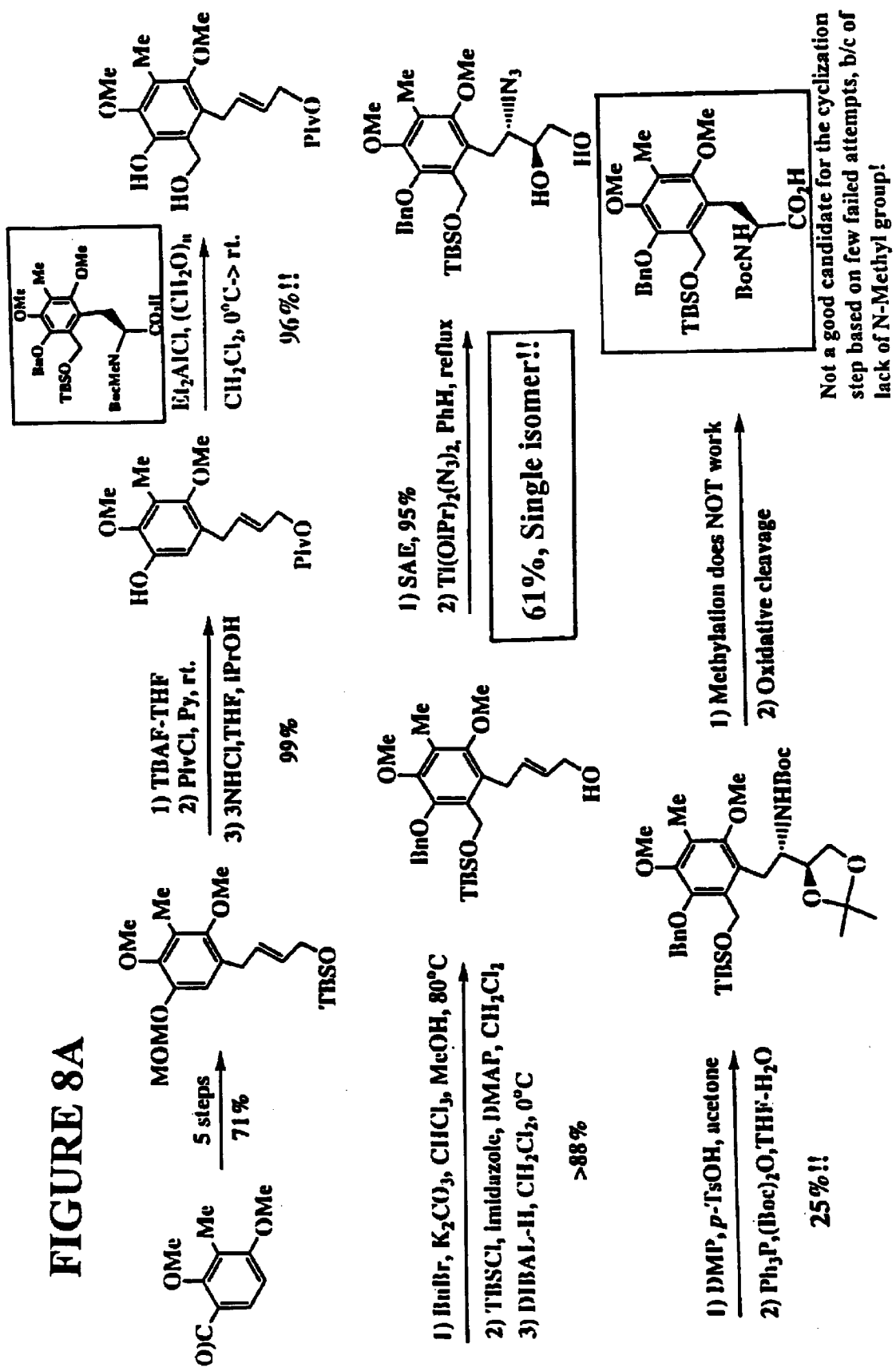
FIGS. 8A and 8B show the modified synthesis of amino acid for synthesis strategy B of Saframycin B.
Figure 8B:
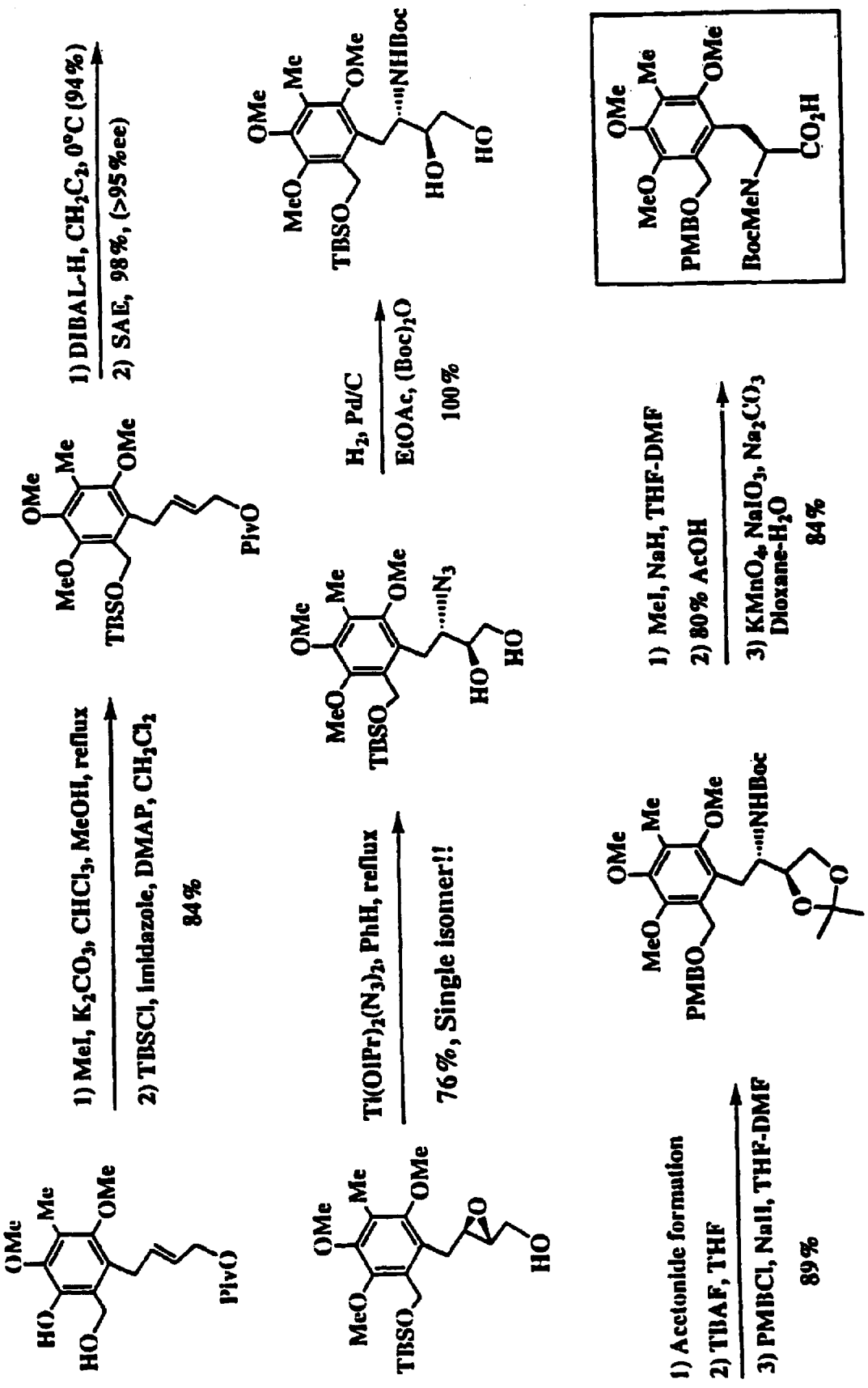
Figure 9A:
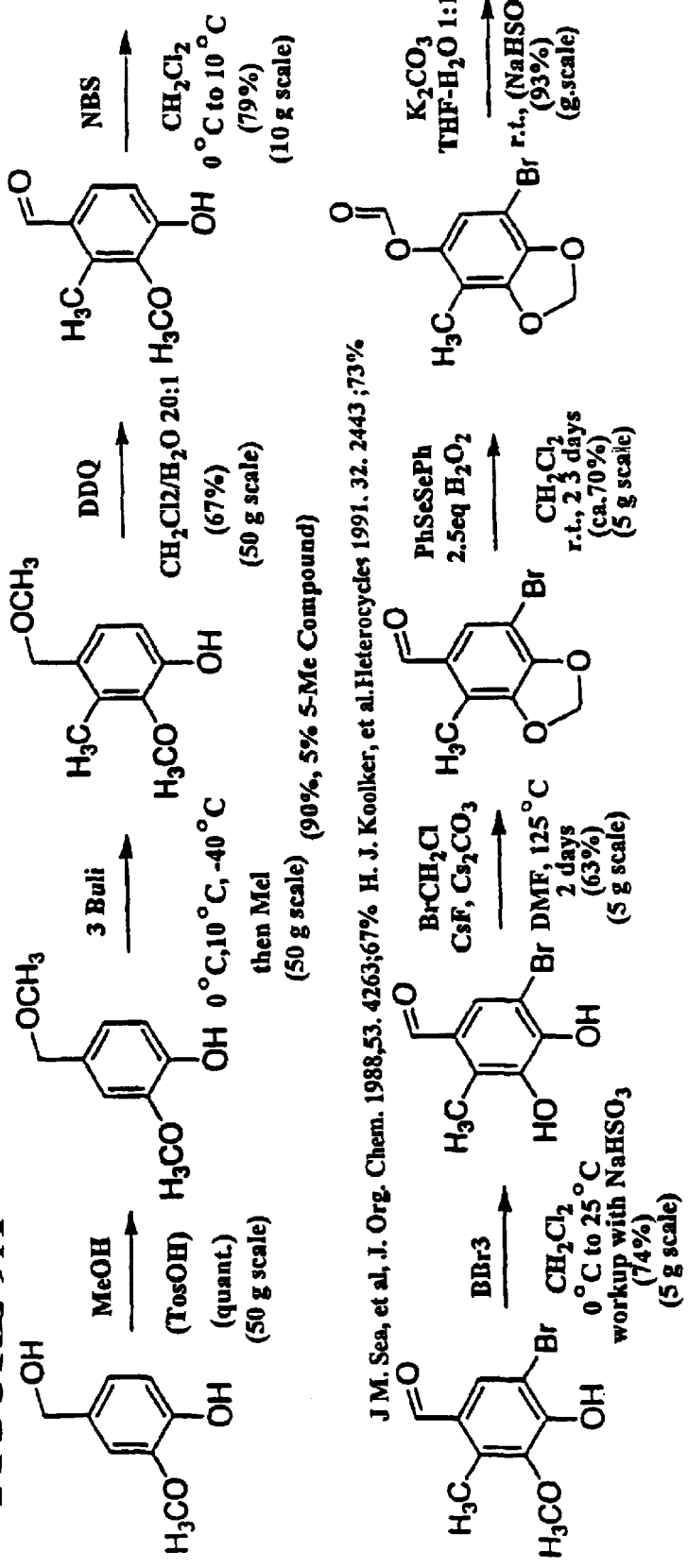
FIGS. 9A and 9B show the synthesis of the pentasubstituted aromatic system and the tertahydroisoquinoline of ET 743, i.e. the left part of ET 743.
Figure 9A:
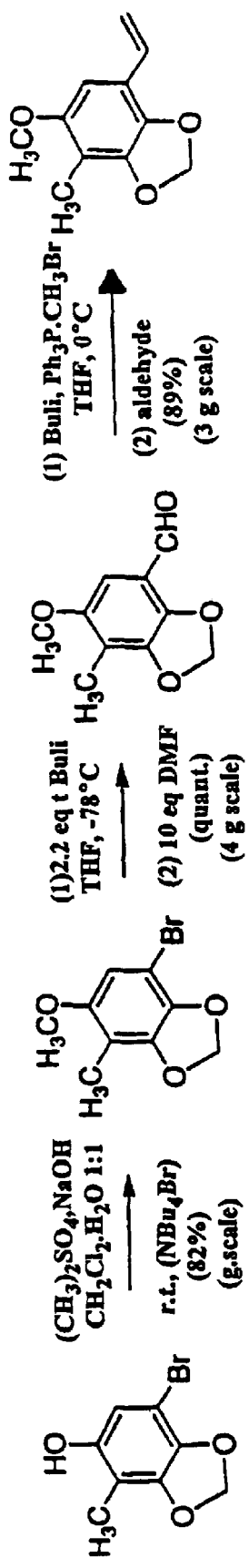
Figure 9B:
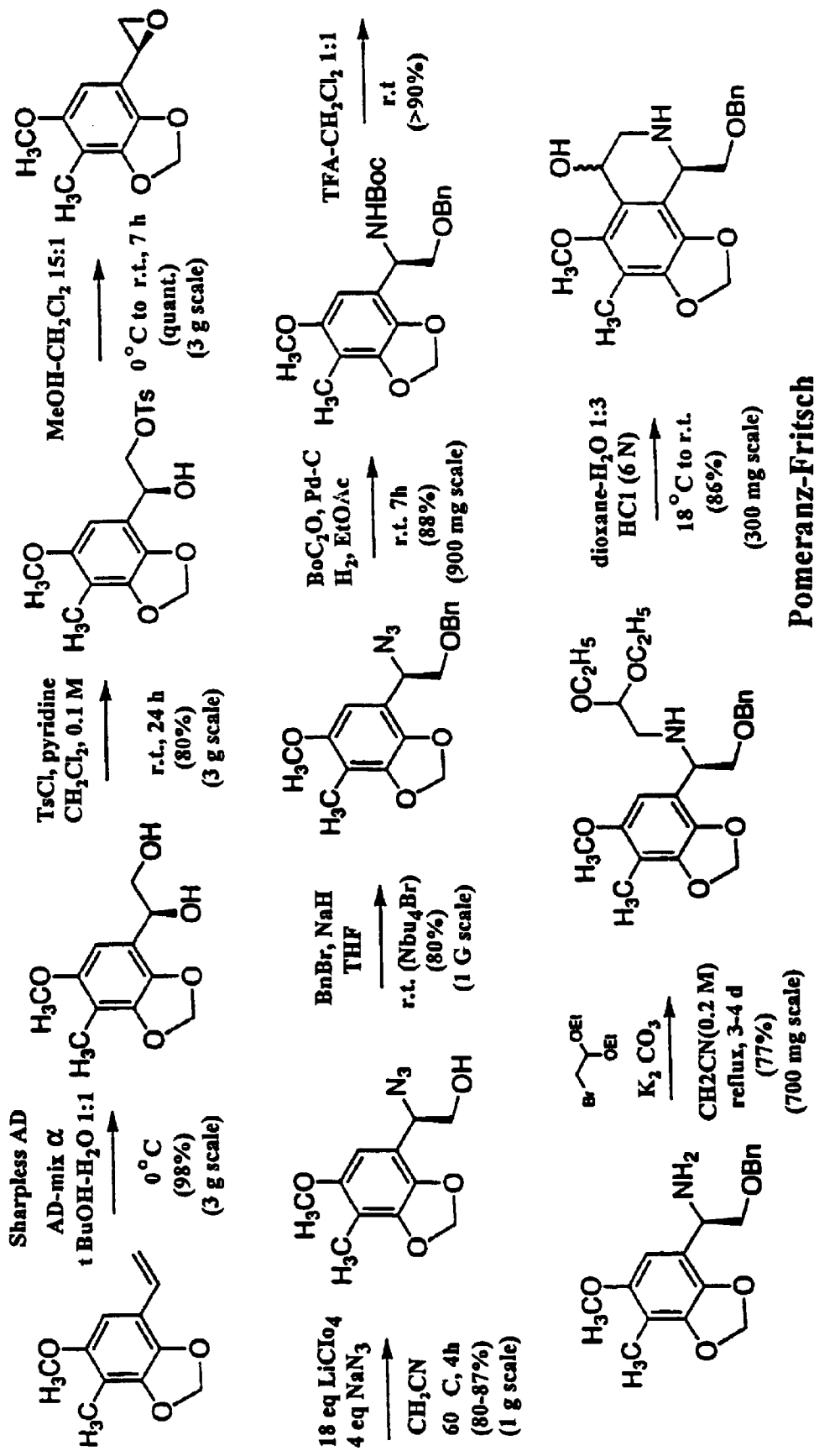
Figure 10A:
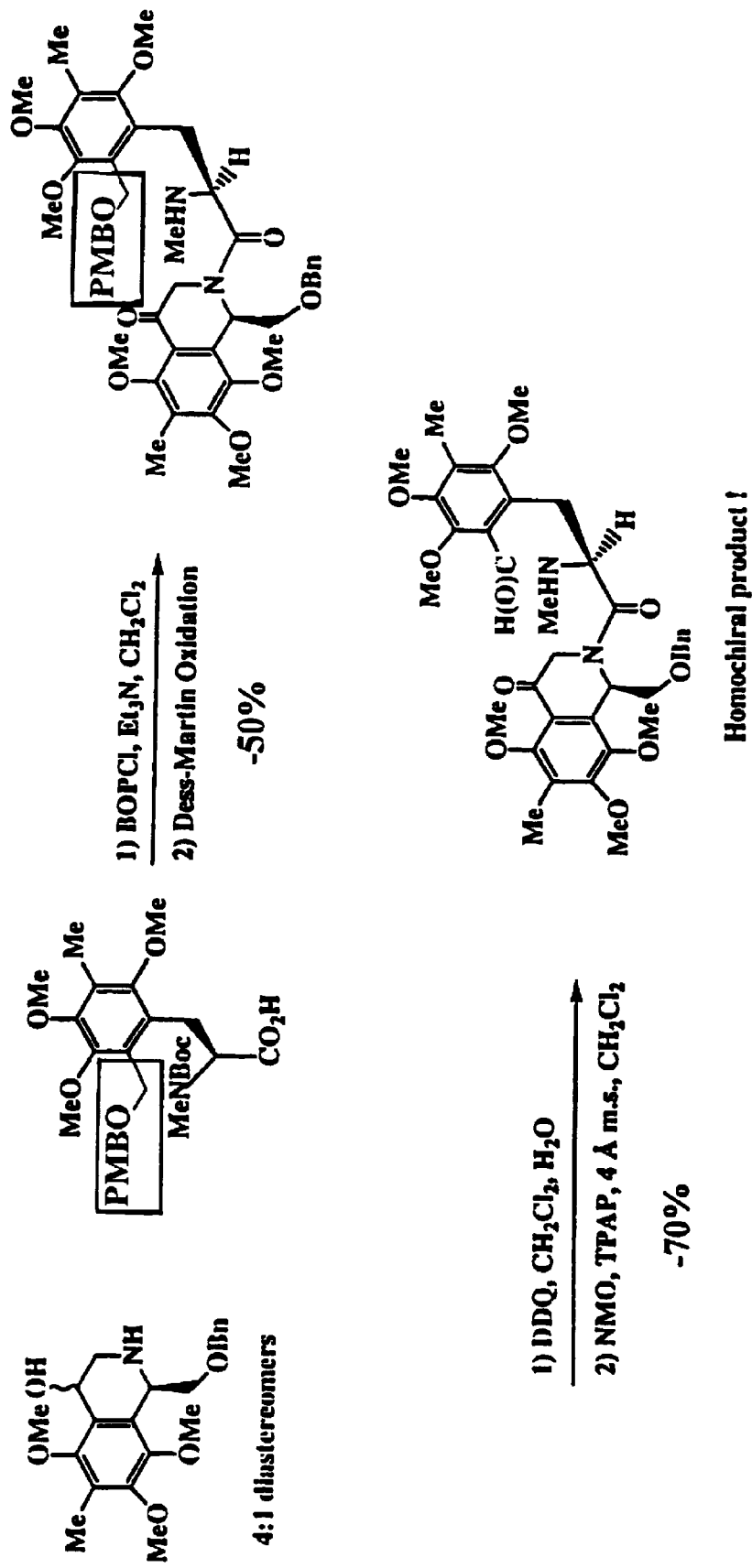
FIG. 10A shows the coupling steps for the synthesis strategy B for Saframycin B.
Figure 10B:
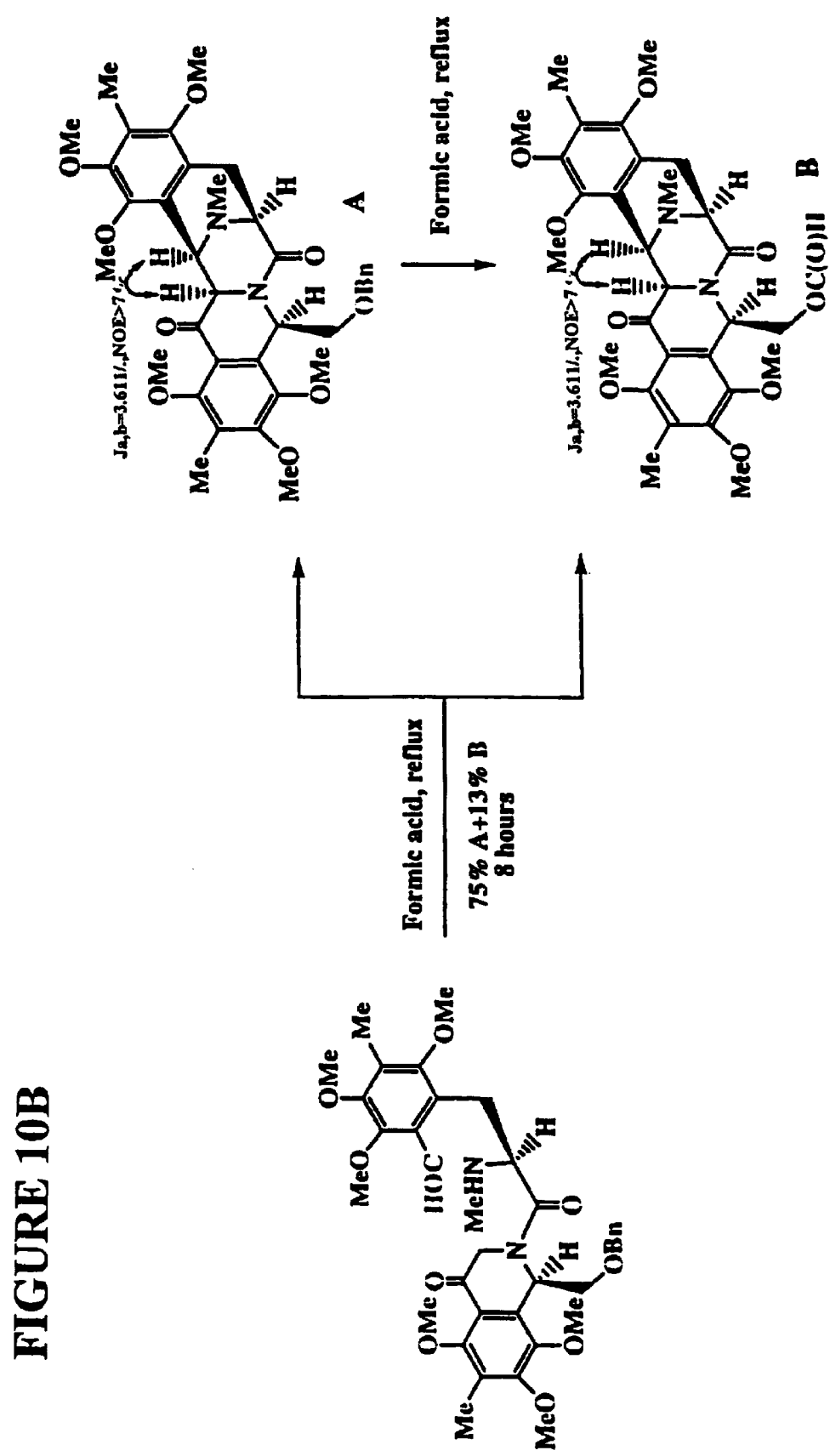
FIG. 10B shows the cyclization for the synthesis strategy B of Saframycin B.
Figure 11:
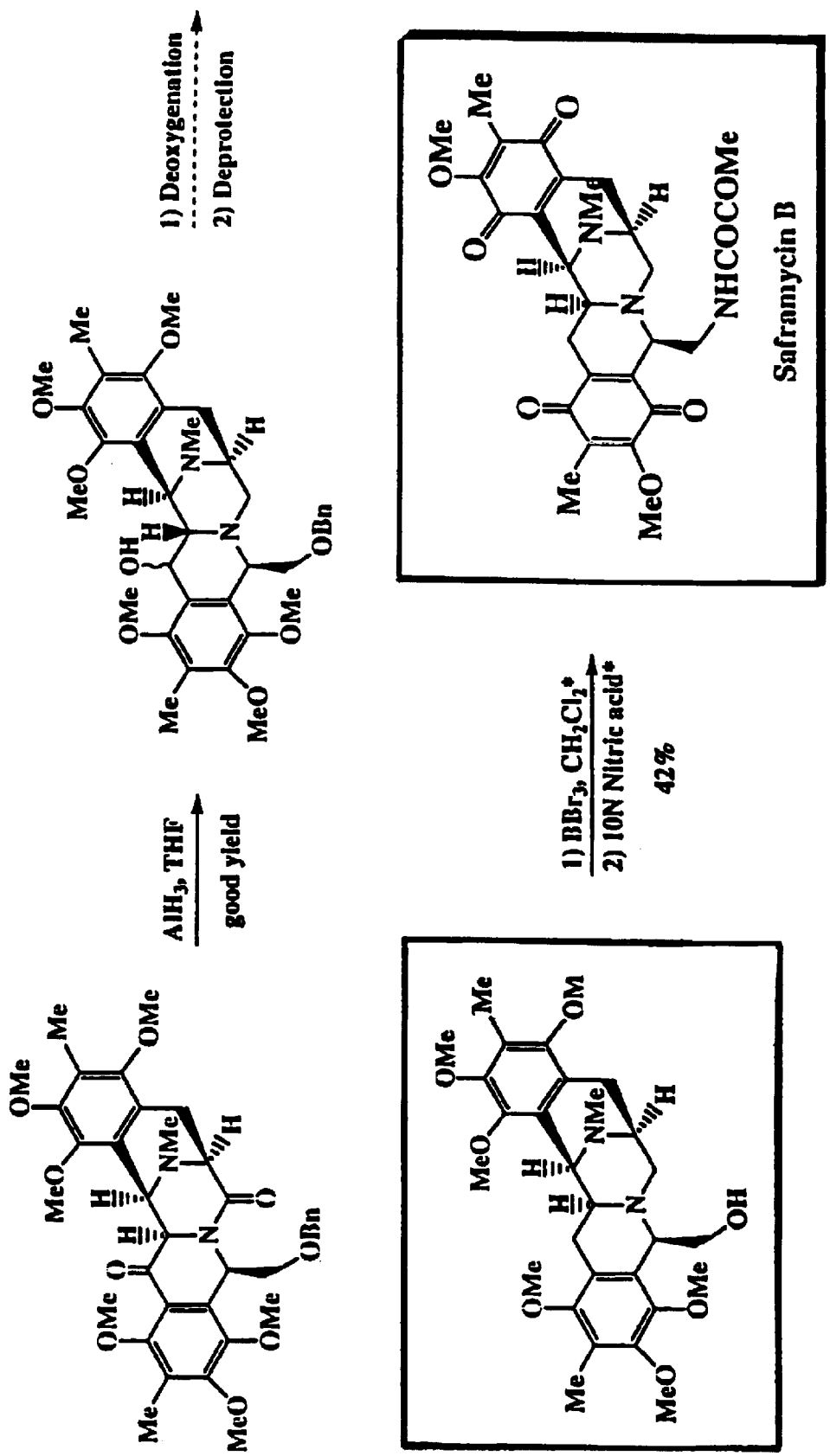
FIG. 11 shows the final steps for the total synthesis of Saframycin B.
Figure 12:
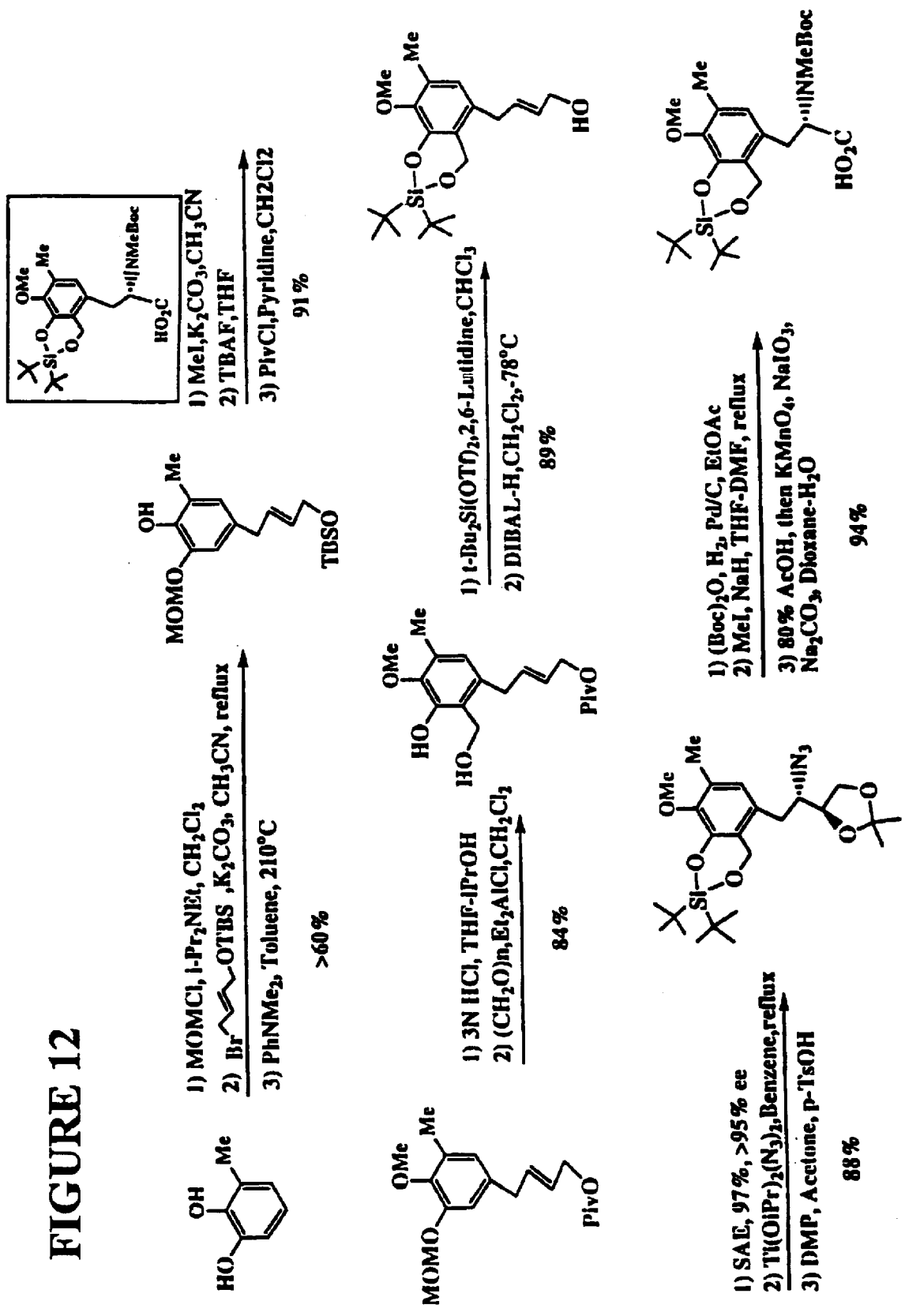
FIG. 12 shows the enantioselective synthesis of amino acid for the synthesis of ET 743.
Figure 13:
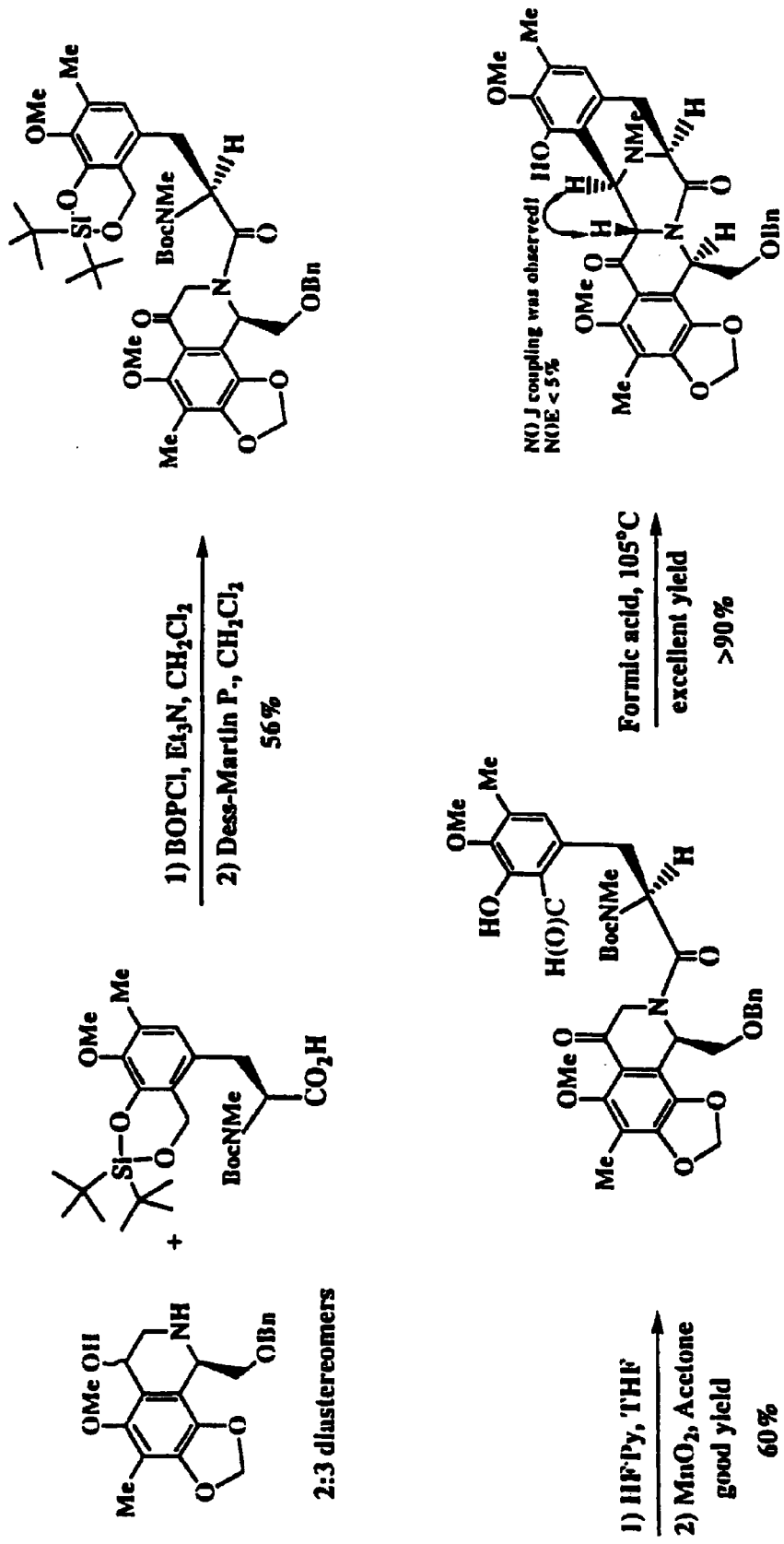
FIG. 13 shows the coupling and the cyclization steps in synthesis for ET 743.
Figure 14:
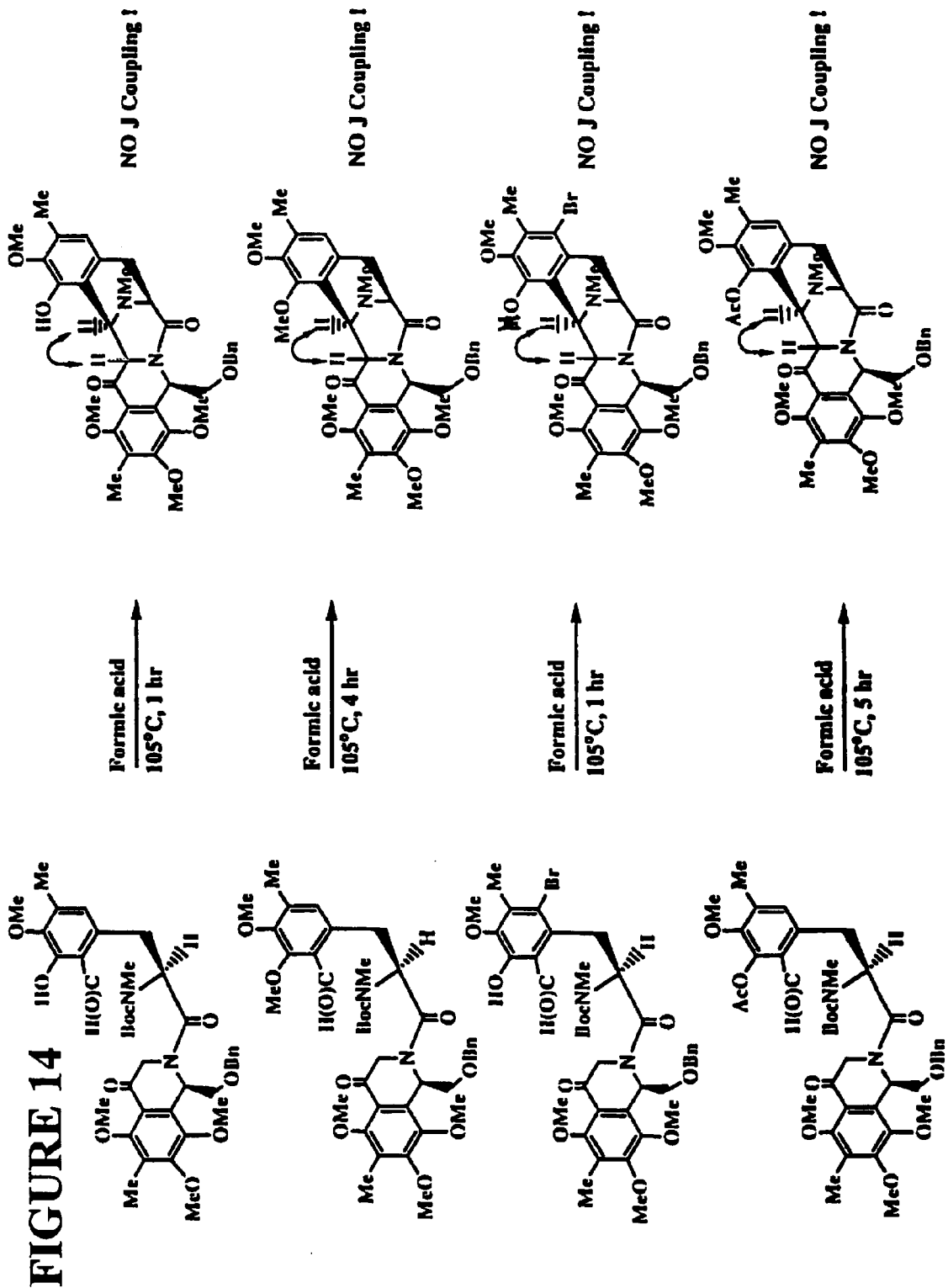
FIG. 14 shows the ET 743 series cyclization analogs.
Figure 15:
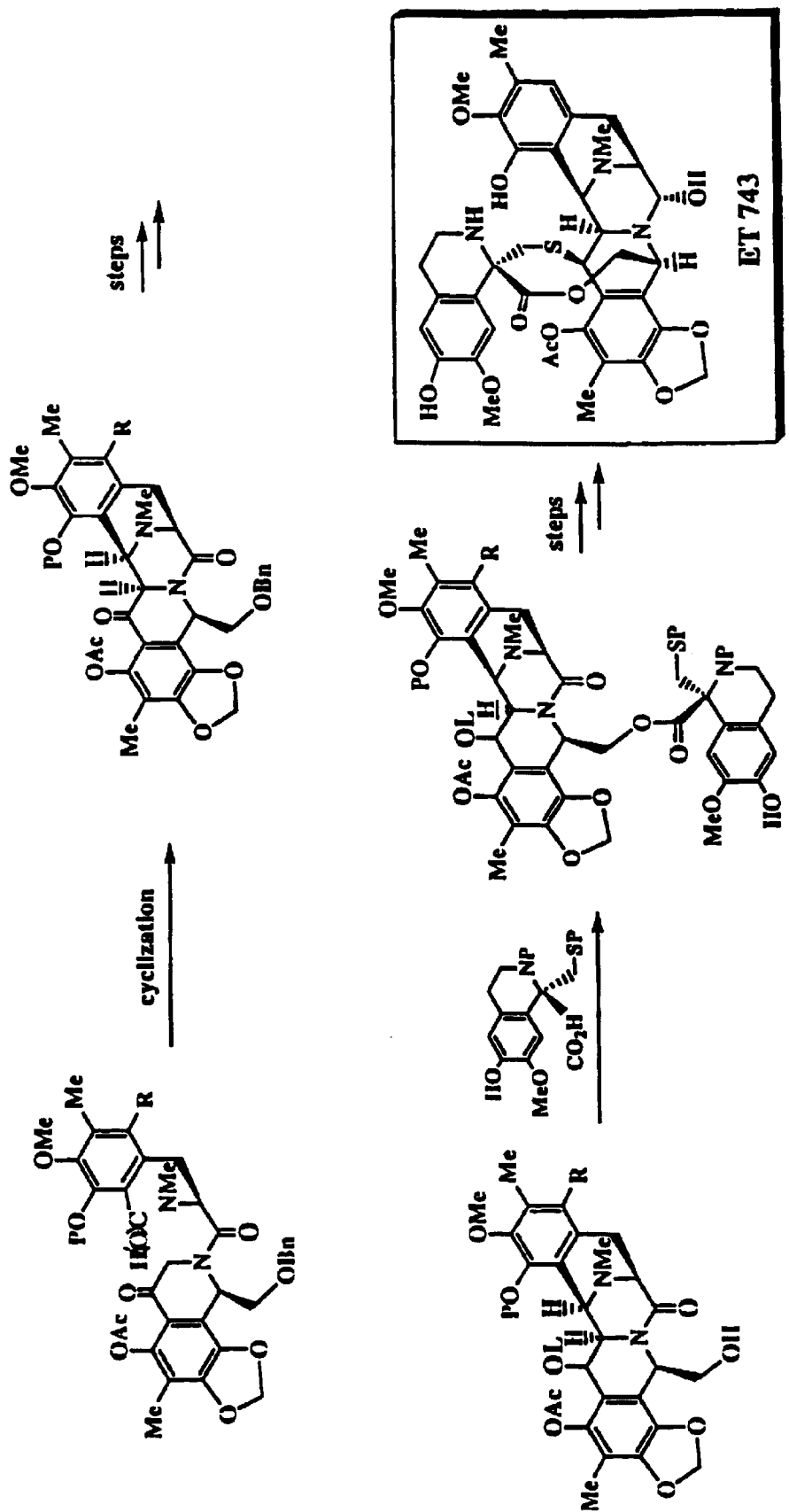
FIG. 15 shows the plan for the total synthesis of ET 743.

In embodiment of the subject invention provides compounds having the formula:

wherein $R_1$ and $R_4$ is H, a $C_1$ to $C_4$ alkyl group, or an acyl group;

wherein $R_2$ is an ether, ester, amide, a phthalimide group, a substituted phathalimide group or is covalently bound to $R_6$;

wherein $R_3$ is =O, OH, an ether group, an acyl group, or a sulfide group;

wherein $R_5$ is H, halogen, OH, an ether group, an acyl group, or an amide group;

wherein $R_6$ is =O, OH, $OCH_3$, CN, an acyloxy group or is covalently bound to $R_2$;

wherein $R_7$, is =O, OH, halogen, an ether group, or an acyl group;

wherein $R_8$ and $R_9$ are independently H, $CH_3$, $OCH_3$, $OC_2H_5$, Br, F, $CF_3$, or $R_8$ and $R_9$ are joined together as a methylenedioxy group, or other five or six membered ring;

wherein $R_{10}$ and $R_{11}$ are independently $CH_3$, $OCH_3$, $OC_2H_5$, $SCH_3$, or $SC_2H_5$;

wherein $R_{12}$ is H, a $C_1$ to $C_4$ alkyl group, or an acyl group; and wherein the chiral center marked * has the R or the S configuration.

In another embodiment, the compound has the formula:

where $R_1$, $R_2$, $R_3$, $R_4$, $R_5$, $R_6$, $R_7$, $R_8$, and $R_9$ are as defined above.

In yet another embodiment, the compound has the formula:

where $R_1$, $R_2$, $R_3$, $R_4$, $R_5$, $R_6$, and $R_7$ are as defined above.

In preferred embodiments of the immediately preceding formula, $R_1$ is $CH_3$, $R_3$ is =O, $R_4$ is $CH_3$, $R_5$ is $OCH_3$, $R_6$ is =O, and $R_7$ is H.

In another preferred embodiment of the preceding formula, $R_1$ is H, $R_3$ is =O, $R_4$ is $CH_3$, $R_5$ is $OCH_3$, $R_6$ is =O, and $R_7$ is H.

In yet another preferred embodiment of the preceding formula, $R_1$ is H, $R_3$ is =O, $R_4$ is benzyl, $R_5$ is $OCH_3$, $R_6$ is =O, and $R_7$ is H.

In yet another preferred embodiment of the preceding formula, $R_1$ is H, $R_3$ is =O, $R_4$ is H, $R_5$ is $OCH_3$, $R_6$ is =O, and $R_7$ is H.

In yet another preferred embodiment of the preceding formula, $R_1$ is H, $R_3$ is =O, $R_4$ is H, $R_5$ is H, $R_6$ is =O, and $R_7$ is H.

In yet another preferred embodiment of the preceding formula, $R_1$ is H, $R_3$ is =O, $R_4$ is H, $R_5$ is halogen, $R_6$ is =O, and $R_7$ is H.

In all of the embodiments, and particularly in the preferred embodiments, $R_2$ is OC(O)H, $R_2$ is H, $R_2$ is OH, $R_2$ is —O-benzyl, $R_2$ is OCOCH$_3$, $R_2$ is —O-t-butyldimethylsilyl, or $R_2$ is —O-Pivaloyl.

In yet another embodiment, the compound has the formula:

[Chemical structure]

where $R_1$, $R_2$, $R_3$, $R_4$, $R_5$, $R_6$, and $R_7$ are as defined above.

In preferred embodiments of the immediately preceding formula, $R_1$ is CH$_3$, $R_3$ is =O, $R_4$ is CH$_3$, $R_5$ is OCH$_3$, $R_6$ is =O, and $R_7$ is H.

In another preferred embodiment of the preceding formula, $R_1$ is H, $R_3$ is =O, $R_4$ is CH$_3$, $R_5$ is OCH$_3$, $R_6$ is =O, and $R_7$ is H.

In yet another preferred embodiment of the preceding formula, $R_1$ is H, $R_3$ is =O, $R_4$ is benzyl, $R_5$ is OCH$_3$, $R_6$ is =O, and $R_7$ is H.

In yet another preferred embodiment of the preceding formula, $R_1$ is H, $R_3$ is =O, $R_4$ is H, $R_5$ is OCH$_3$, $R_6$ is =O, and $R_7$ is H.

In yet another preferred embodiment of the preceding formula, $R_1$ is H, $R_3$ is =O, $R_4$ is H, $R_5$ is H, $R_6$ is =O, and $R_7$ is H.

In yet another preferred embodiment of the preceding formula, $R_1$ is H, $R_3$ is =O, $R_4$ is H, $R_5$ is halogen, $R_6$ is =O, and $R_7$ is H.

In all of the embodiments, and particularly in the preferred embodiments, $R_2$ is OC(O)H, $R_2$ is H, $R_2$ is OH, $R_2$ is —O-benzyl, $R_2$ is OCOCH$_3$, $R_2$ is —O-t-butyldimethylsilyl, or $R_2$ is —O-Pivaloyl.

The subject invention also provides compounds having the formula:

[Chemical structure 2]

wherein $R_1$ and $R_4$ is H, a $C_1$ to $C_4$ alkyl group, or an acyl group;

wherein $R_2$ is an ether, ester, amide, or a phthalimide group;

wherein $R_5$ is H, halogen, OH, an ether group, an acyl group, or an amide group;

wherein $R_6$ is =O, OH, OCH$_3$, CN, or an acyloxy group;

wherein $R_7$, is =O, OH, halogen, an ether group, or an acyl

In a preferred embodiment, the compound has the formula:

[Chemical structure]

where $R_1$, $R_2$, $R_4$, $R_5$, $R_6$, and $R_7$ are as defined above.

In preferred embodiments of the immediately preceding formula, $R_1$ is CH$_3$, $R_4$ is CH$_3$, $R_5$ is OCH$_3$, $R_6$ is =O, and $R_7$ is H.

In another preferred embodiment of the preceding formula, $R_1$ is H, $R_4$ is CH$_3$, $R_5$ is OCH$_3$, $R_6$ is =O, and $R_7$ is H.

In yet another preferred embodiment of the preceding formula, $R_1$ is H, $R_4$ is benzyl, $R_5$ is OCH$_3$, $R_6$ is =O, and $R_7$ is H.

In yet another preferred embodiment of the preceding formula, $R_1$ is H, $R_4$ is H, $R_5$ is OCH$_3$, $R_6$ is =O, and $R_7$ is H.

In yet another preferred embodiment of the preceding formula, $R_1$ is H, $R_4$ is H, $R_5$ is H, $R_6$ is =O, and $R_7$ is H.

In yet another preferred embodiment of the preceding formula, group;

wherein $R_8$ and $R_9$ are independently H, CH$_3$, OCH$_3$, OC$_2$H$_5$, Br, F, CF$_3$, or $R_8$ and $R_9$ are joined together as a methylenedioxy group, or other five or six membered ring;

wherein $R_{10}$ and $R_{11}$ are independently CH$_3$, OCH$_3$, OC$_2$H$_5$, SCH$_3$, or SC$_2$H$_5$;

wherein $R_{12}$ is H, a $C_1$ to $C_4$ alkyl group, or an acyl group.

In another embodiment, the compound has the formula:

[Chemical structure]

where $R_1$, $R_2$, $R_4$, $R_5$, $R_6$, $R_7$, $R_8$ and $R_9$ are as defined above.

$R_1$ is H, $R_4$ is H, $R_5$ is halogen, $R_6$ is =O, and $R_7$ is H.

In all of the embodiments, and particularly in the preferred embodiments, $R_2$ is OC(O)H, $R_2$ is H, $R_2$ is OH, $R_2$ is —O-benzyl, $R_2$ is OCOCH$_3$, $R_2$ is —O-t-butyldimethylsilyl, or $R_2$ is —O-Pivaloyl.

In another preferred embodiment, the compound has the formula:

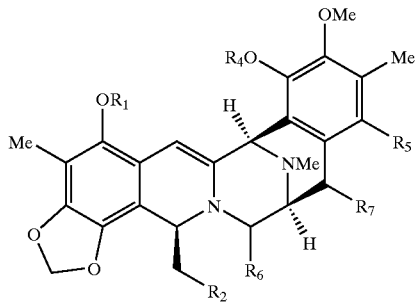

where $R_1$, $R_2$, $R_4$, $R_5$, $R_6$, and $R_7$ are as defined above.

In preferred embodiments of the immediately preceding formula, $R_1$ is CH$_3$, $R_4$ is CH$_3$, $R_5$ is OCH$_3$, $R_6$ is =O, and $R_7$ is H.

In another preferred embodiment of the preceding formula, $R_1$ is H, $R_4$ is CH$_3$, $R_5$ is OCH$_3$, $R_6$ is =O, and $R_7$ is H.

In yet another preferred embodiment of the preceding formula, $R_1$ is H, $R_4$ is benzyl, $R_5$ is OCH$_3$, $R_6$ is =O, and $R_7$ is H.

In yet another preferred embodiment of the preceding formula, $R_1$ is H, $R_4$ is H, $R_5$ is OCH$_3$, $R_6$ is =O, and $R_7$ is H.

In yet another preferred embodiment of the preceding formula, $R_1$ is H, $R_4$ is H, $R_5$ is H, $R_6$ is =O, and $R_7$ is H.

In yet another preferred embodiment of the preceding formula, $R_1$ is H, $R_4$ is H, $R_5$ is halogen, $R_6$ is =O, and $R_7$ is H.

In yet another preferred embodiment of the preceding formula, $R_1$ is H, $R_4$ is CH$_3$, $R_5$ is CH$_3$, $R_6$ is =O, and $R_7$ is H (Compound 110).

In all of the embodiments, and particularly in the preferred embodiments, $R_2$ is OC(O)H, $R_2$ is H, $R_2$ is OH, $R_2$ is —O-benzyl, $R_2$ is OCOCH$_3$, $R_2$ is —O-t-butyldimethylsilyl, or $R_2$ is —O-Pivaloyl.

The subject invention also provides compounds having the following general formula which are used in the synthesis of compounds within the saframycin-ecteinascidin series:

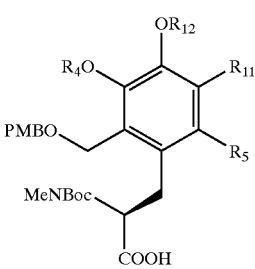

A wherein $R_4$ is H, a $C_1$ to $C_4$ alkyl group, or an acyl group;
wherein $R_5$ is H, halogen, OH, an ether group, an acyl group, a sulfide group or an amide group;
wherein $R_{11}$ is CH$_3$, OCH$_3$, OC$_2$H$_5$, SCH$_3$, or SC$_2$H$_5$; and
wherein $R_{12}$ is H, a $C_1$ to $C_4$ alkyl group, or an acyl group.

In another embodiment, the compound has the formula:

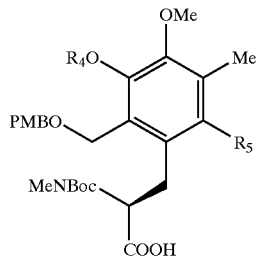

where $R_4$ and $R_5$ are defined as above.

In a preferred embodiment of the immediately preceding formula, $R_4$ is CH$_3$ and $R_5$ is CH$_3$ (compound 1).

In another preferred embodiment of the preceding formula, $R_4$ is Benzene and $R_5$ is H (compound 3).

The subject invention also provides compounds having the following general formula which are used in the synthesis of compounds within the saframycin-ecteinascidin series:

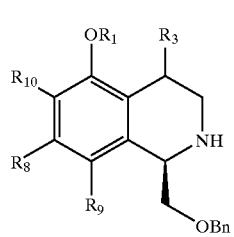

B wherein $R_1$ is H, a $C_1$ to $C_4$ alkyl group, or an acyl group;
wherein $R_3$ is =O, OH, an ether group, an acyl group, a sulfide group or an amide group;
wherein $R_8$ and $R_9$ are independently H, CH$_3$, OCH$_3$, OC$_2$H$_5$, SCH$_3$, SC$_2$H$_5$, or $R_8$ and $R_9$ are joined together to form a five or six membered ring;
wherein $R_{10}$ is CH$_3$, OCH$_3$, OC$_2$H$_5$, SCH$_3$, or SC$_2$H$_5$.

In another embodiment, of the immediately preceding formula the compound having the formula:

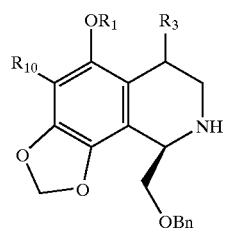

where $R_1$, $R_3$ and $R_{10}$ are defined as above.

The subject invention also provides compounds having the following general formula which are used in the synthesis of compounds within the saframycin-ecteinascidin series:

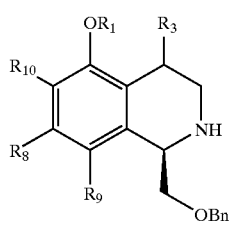

wherein $R_1$ is H, a $C_1$ to $C_4$ alkyl group, or an acyl group;
wherein $R_3$ is =O, OH, an ether group, an acyl group, a sulfide group, an amide group or H;
wherein $R_8$ and $R_9$ are independently H, $CH_3$, $OCH_3$, $OC_2H_5$, $SCH_3$, $SC_2H_5$, or $R_8$ and $R_9$ are joined together to form a five or six membered ring;
wherein $R_{10}$ is $CH_3$, $OCH_3$, $OC_2H_5$, $SCH_3$, or $SC_2H_5$.

In another embodiment, of the immediately preceding formula the compound having the formula:

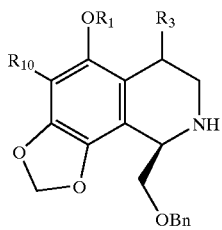

where $R_1$, $R_3$ and $R_{10}$ are defined as above.

The subject invention also provides a method of producing the compounds within the saframycin-ecteinascidin series such as compound 1, which method comprises reacting a compound having the formula

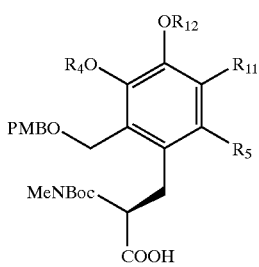

A with a compound having the formula

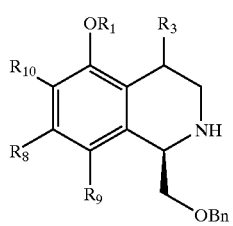

B wherein $R_1$ and $R_4$ is H, a $C_1$ to $C_4$ alkyl group, or an acyl group;
wherein $R_3$ is =O, OH, an ether group, an acyl group, a sulfide group or an amide group;
wherein $R_5$ is H, halogen, OH, an ether group, an acyl group, or an amide group;

wherein $R_8$ and $R_9$ are independently H, $CH_3$, $OCH_3$, $OC_2H_5$, Br, F, $CF_3$, or $R_8$ and $R_9$ are joined together as a methylenedioxy group, or other five or six membered ring;

In yet another preferred embodiment, the compound has the formula:

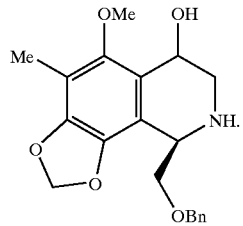

C

In yet another preferred embodiment, the compound has the formula:

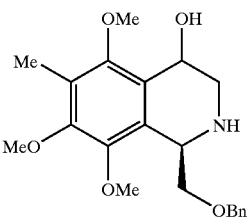

wherein $R_{10}$ and $R_{11}$ are independently $CH_3$, $OCH_3$, $OC_2H_5$, $SCH_3$, or $SC_2H_5$; and
wherein $R_{12}$ is H, a $C_1$ to $C_4$ alkyl group, or an acyl group.

In an embodiment of the preceding method, the reaction is performed in the presence of N,N-bis(2-oxo-3-oxazolidinyl)phosphinic chloride.

In another embodiment of the method, the reaction is performed in the presence of Dess-Martin periodinane. In this embodiment, the reaction is further performed in the presence of $CH_2Cl_2$.

This invention also provides a method of producing the compound 2 above, which comprises reacting compound 1 above with camphor sulfonic acid (CSA) in the presence of toluene.

This invention also provides a method of producing the compound 1 above, which comprises reacting compound 2 above with $H_2$, 10% Pd/C, Ethanol-ascetic acid in the presence hydrochloric acid.

In another embodiment the subject invention provides for a compound having the formula:

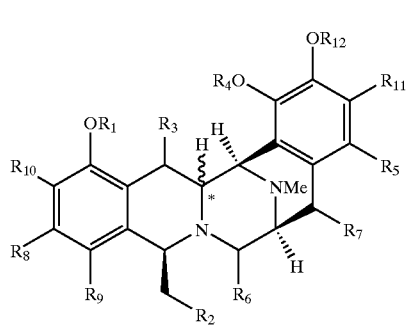

3 wherein $R_1$ and $R_4$ is H, a $C_1$ to $C_4$ alkyl group, or an acyl group;

wherein $R_2$ is an ether, ester, amide, aromatic group or is covalently bound to $R_6$;

wherein $R_3$ is =O, OH, H, an ether group, an acyl group, or a sulfide group;

wherein $R_5$ is H, halogen, OH, —$OC_{(2-6)}$ alkyl group, an ether group, an acyl group, or an amide group;

wherein $R_6$ is =O, OH, $OCH_3$, CN, or an acyloxy group or is covalently bound to $R_2$;

wherein $R_7$, is H, =O, OH, $OCH_3$, halogen, an ether group, or an acyl group;

wherein $R_8$ and $R_9$ are independently H, $CH_3$, $OCH_3$, $OC_2H_5$, Br, F, $CF_3$, or $R_8$ and $R_9$ are joined together as a methylenedioxy group, or other five or six membered ring;

wherein $R_{10}$ and $R_{11}$ are independently $CH_3$, $OCH_3$, $OC_2H_5$, $SCH_3$, or $SC_2H_5$;

wherein $R_{12}$ is H, a $C_1$ to $C_4$ alkyl group, or an acyl group; and wherein the chiral center marked * has the R or the S configuration.

In yet another embodiment the compound has the formula:

wherein $R_1$, $R_2$, $R_3$, $R_4$, $R_5$, $R_6$, $R_7$, $R_8$, and $R_9$ are defined as in the preceding formula.

In yet another embodiment, the compound has the formula:

wherein $R_1$, $R_2$, $R_3$, $R_4$, $R_5$, $R_6$, and $R_7$ are defined as in the formula above.

In a preferred embodiment of the immediately preceding formula, $R_1$ is H, $R_2$ is OH, $R_3$ is H, $R_4$ is H, $R_5$, is H, $R_6$ is =O, and $R_7$ is H (Compound 113).

In another preferred embodiment of the preceding formula, $R_1$ is $CH_3$, $R_2$ is OH, $R_3$ is H, $R_4$ is $CH_3$, $R_5$ is $OCH_3$, $R_6$ is H and $R_7$ is H (Compound 107).

In yet another preferred embodiment of the preceding formula, $R_1$ is H, $R_2$ is OH, $R_3$ is H, $R_4$ is $CH_3$, $R_5$ is $OCH_3$, $R_6$ is =O and $R_7$ is H (Compound 104).

In yet another preferred embodiment of the preceding formula, $R_1$ is H, $R_2$ and $R_6$ are joined as an ester bond, $R_3$ is H, $R_4$ is $CH_3$, $R_5$ is $OCH_3$, and $R_7$ is H (Compound 105).

In yet another preferred embodiment of the preceding formula, $R_1$ is $CH_3$, $R_2$ and $R_6$ are joined as an ester bond, $R_9$ is H, $R_4$ is $CH_3$, $R_5$ is $OCH_3$, and $R_7$ is H (Compound 106).

In another embodiment, the compound has the formula:

wherein $R_1$, $R_2$, $R_3$, $R_4$, $R_5$, $R_6$, and $R_7$ are defined as in the preceding formula.

In a preferred embodiment of the immediately preceding formula, $R_1$ is H, $R_2$ is OH, $R_3$ is OH, $R_4$ is $CH_3$, $R_5$ is $OCH_3$, $R_6$ is =O, and $R_7$ is H (Compound 109).

In another preferred embodiment of the preceding formula, $R_1$ is H, $R_2$ is OH, $R_3$ is H, $R_4$ is $CH_3$, $R_5$ is $OCH_3$, $R_6$ is =O, and $R_7$ is H (Compound 111).

In yet another preferred embodiment of the preceding formula, $R_1$ is H, $R_2$ is OH, $R_3$ is =O, $R_4$ is $CH_3$, $R_5$ is $OCH_3$, $R_6$ is =O, and $R_7$ is H (Compound 108).

The subject invention also provides for a method of producing compound 3, comprising reacting a compound having the formula A with a compound having the formula C.

In an embodiment of the preceding method, the reaction is performed in the presence of N,N-bis(2-oxo-3-oxazolidinyl)phosphinic chloride.

In another embodiment of the preceding method, the reaction is performed in the presence of Dess-Martin periodinate.

In yet another embodiment of the preceding method, the reaction is further performed in the presence of $CH_2Cl_2$.

In yet another embodiment of the preceding method, the reaction is performed with $H_2$, 10% Pd/C, Ethanol-ascetic acid in the presence hydrochloric acid.

This invention also provides a method of producing the compound 3 above, which comprises reacting compound 2 above with $H_2$, 10% Pd/C, Ethanol-ascetic acid in the presence hydrochloric acid.

This invention also provides a method of producing the compound 2 above, which comprises reacting compound 3 above with camphor sulfonic acid (CSA) in the presence of toluene.

This invention also provides a pharmaceutical composition for treating a tumor in a subject, which comprises a pharmaceutically effective amount of compound 1 above or compound 2 above or compound 3 above.

This invention also provides a method of inhibiting proliferation of tumor cells which comprises contacting the cells under suitable conditions with an effective amount of compound 1 above or compound 2 above or compound 3 above.

This invention also provides a method of treating a patient having a tumor characterized by proliferation of neoplastic cells which comprises administering to the patient an effective amount of compound 1 above or compound 2 above or compound 3 above. In this method the effective amount may be from about 0.5 mg to about 5 mg per day, preferably from about 1 mg to about 3 mg per day, and most preferably about 2 mg per day.

The abbreviation used throughout this disclosure and in the synthesis schemes are abbreviations commonly used in the art of synthetic chemistry and may be readily found in a synthetic chemistry text book.

The abbreviations used in this disclosure are also provided below:

| | |
|---|---|
| Ac | acetyl |
| BOC | t-butoxycarbonyl |
| DAM | di(4-methoxyphenyl)methyl |
| Dmp | dimethylphosphinyl |
| DMPM | 3,4-dimethoxybenzyl |
| MOM | methoxymethyl |
| PMB or MPM | p-methoxybenzyl or p-methoxyphenylmethyl- |
| PMBM | p-methoxybenzyloxymethyl |
| Pv or Piv | pivaloyl |
| TBS or TBDMS | t-butyldimethylsilyl |
| THF | tetrahydrofuranyl |
| Tos or Ts | p-toluenesulfonyl |
| BOP—Cl | N,N-bis(2-oxo-3-oxazolidinyl)phosphinic chloride |
| CSA | camphorsulfonic acid |
| DDQ | 2,3-dichloro-5,6-dicyano-1,4-benzoquinone |
| DIBAL—H | diisobutylaluminum hydride |
| DMAP | 4-N,N-dimethylaminopyridine |
| DMF | N,N-dimethylformamide |
| DMPU | 1,3-dimethyl-3,4,5,6-tetrahydro-2(1H)-pyrimidinone |
| NBS | N-bromosuccinimide |
| TFA | trifluoroacetic acid |

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Example 1

Synthetic Explorations in the Saframycin-Ecteinascidin Series: Construction of Major Chiral Subunits Through Catalytic Asymmetric Induction We undertook to test a synthesis directed to systems of the 4-Oxy-saframycin type. From the perspective of its two aromatic sectors, 4-Oxy-saframycin can be viewed as more closely related to compounds of the saframycin series (Saframycin B, A, and S) than to ET. (5) Indeed, the aromatic rings in III can be regarded as modified hydroquinone versions of the quinone moieties of saframycin, with the important proviso that III also contains a 4-oxo group. This function, in the context of appropriate aromatic domains, is potentially valuable for synthesizing ET and a new range of analogs thereof.

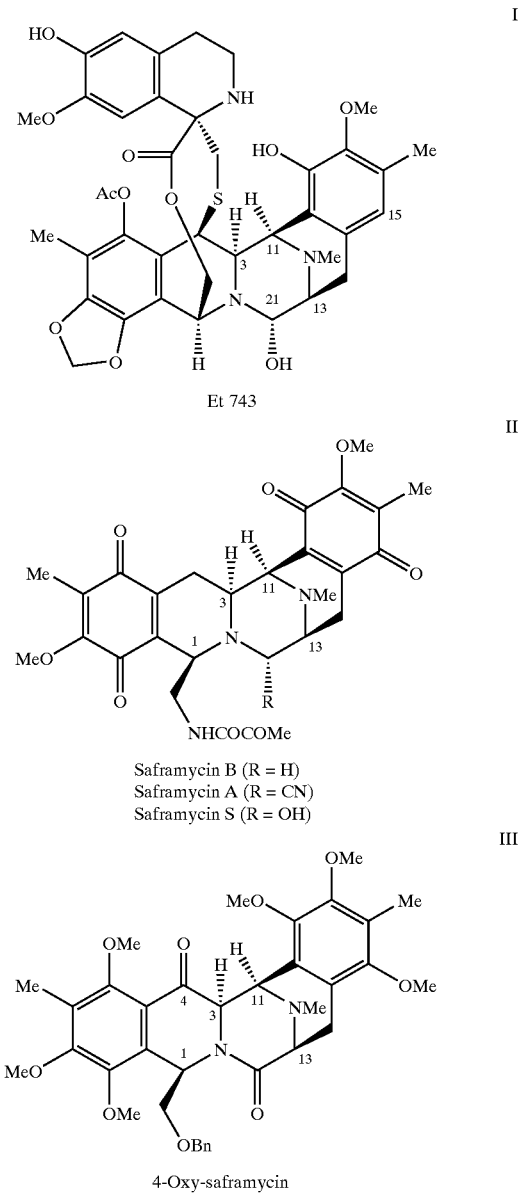

Referring to Scheme 1, our approach to III contemplated the merger of two moieties, 1 and 2, wherein each component would bear the absolute configuration appropriate to the goal system in high enantiomeric excess. In this experiment, we describe the pathways, which we followed for reaching the key building blocks. Our inquiry was directed to the applicability of catalytic oxidative asymmetric induction to these targets, and was strongly influenced by precedents from Sharpless. (6a–c)

Scheme 1.

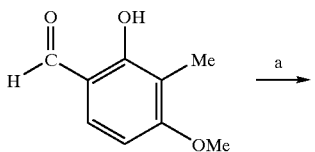

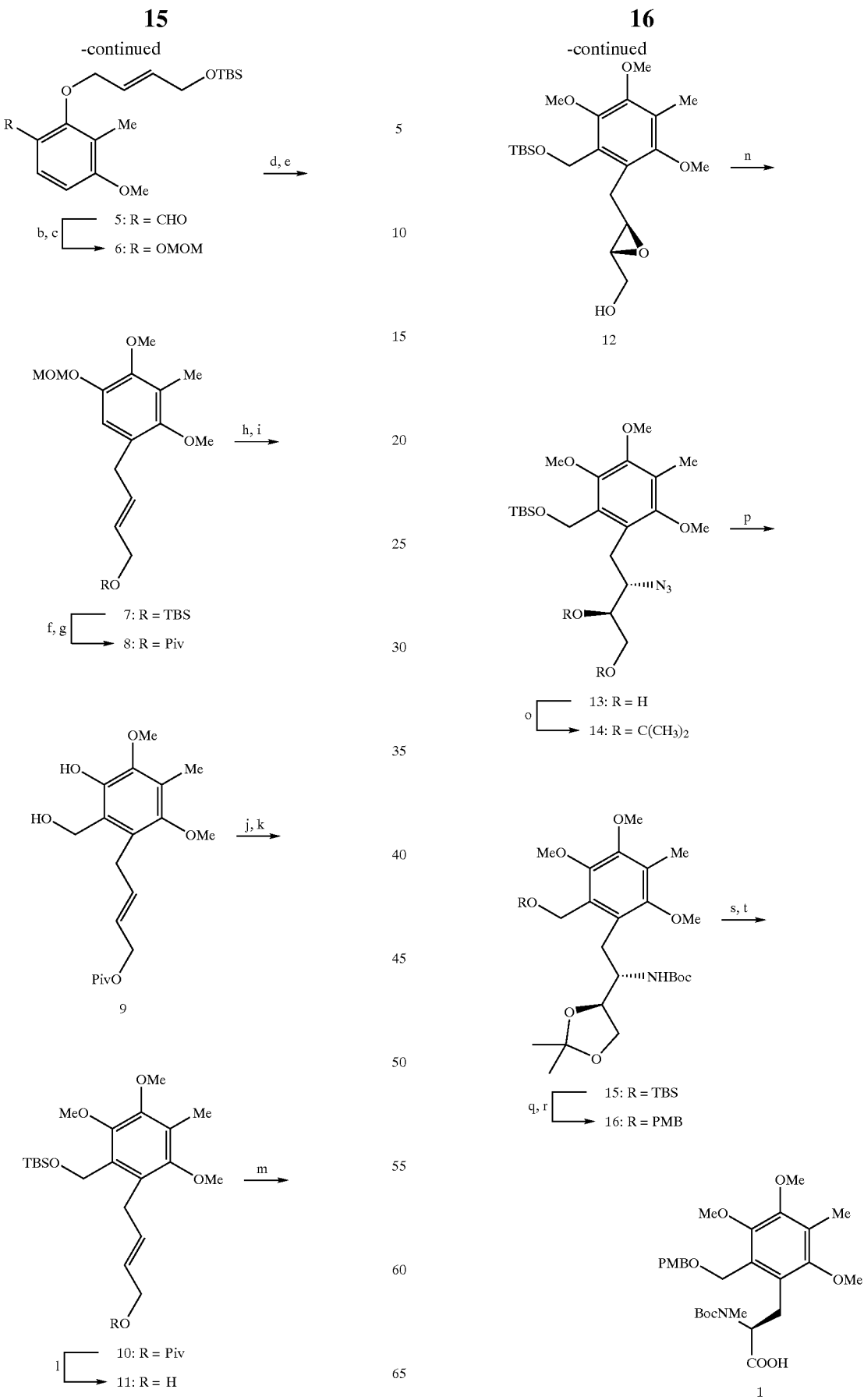

-continued a) 1.1 eq. BrCH$_2$CH=CHCH$_2$OTBS, 1.5 eq. K$_2$CO$_3$, CH$_3$CN, reflux, 5 h, 100%; b) 1.1 eq. 30% H$_2$O$_2$, cat. SeO$_2$, t-BuOH, 40° C, 5 h, then Et$_3$N, MeOH, 85%; c) 1.1 eq. MOMCl, 1.5 eq. (i-Pr)$_2$NEt, CH$_2$Cl$_2$, 80° C, 12 h, 100%; d) 1.1 eq. Me$_2$NPh, toluene, 210° C, 12 h, 96%; e) MeI (xs), 1.5 eq. K$_2$CO$_3$, CH$_3$CN, reflux, 12 h, 87%; f) 1.5 eq. TBAF, THF, 1 h; g) 1.1 eq. PivCl, pyridine-CH$_2$Cl$_2$ (1:20), 3 h; h) 3N HCl, THF-i-PrOH (2:1), 12 h, 99% for 3 steps; i) 3 eq. Et$_2$AlCl, (CH$_2$O)$_n$(xs), CH$_2$Cl$_2$, 12 h, 96%; j) MeI (xs), 1.5 eq. K$_2$CO$_3$, CHCl$_3$—MeOH (2:1), reflux, 12 h, 90%; k) 1.2 eq. TBSCl, 1.5 eq. imidazole, cat. DMAP, CH$_2$Cl$_2$, 1 h, 99%; l) 2.5 eq. DIBAL-H, CH$_2$Cl$_2$, -78° C, 30 min, 94%; m) 8% (D)-DET, 5.6% Ti(OiPr)$_4$, 2 eq. t-BuOOH, m.s. 4Å, -20° C, 1 d, 98% (95% ee); n) 3.5 eq. Ti(OiPr)$_2$(N$_3$)$_2$, PhH, 80° C, 76% (single isomer); o) DMP-acetone (1:2), cat. p-TsOH•H$_2$O, 10 min, 100%; p) H$_2$, Pd/C, EtOAc, 1.2 eq. (Boc)$_2$O, 5 h, 100%; q) 1.5 eq. TBAF, THF, 1 h; r) 1.2 eq. PMBCl, 2 eq. NaH, cat. n-BuN$^+$I$^-$, THF-DMF (5:1), 5 h, 96% for 2 steps; s) MeI (xs), 5 eq. NaH, THF-DMF (5:1), 12 h, reflux, 93%; t) i, 80% AcOH, 12 h; ii, 0.2 eq. KMnO$_4$, 4 eq. NaIO$_4$, 0.5 eq. Na$_2$CO$_3$, Dioxane-H$_2$O (2.5:1), 10 h, 95%

We begin with the route followed to reach 1. The starting material was the readily accessible 4, (7) obtained from the commercially available 2,4-dimethoxy-3-methyl benzaldehyde. Compound 4 was converted by O-alkylation, as shown to ether 5. Dakin-like (8) oxidative cleavage of the aryl aldehyde linkage generated a formate, which was de-acylated by trans esterification. Protection of the resultant phenol afforded 6. The allylic ether had served to protect the C2 hydroxyl group while the substituent at C1 was being adjusted in a constructive way. At this point, p-Claisen rearrangement and sequential protection of the phenol and primary allylic alcohol functions, as indicated, led to 7 and thence 8. Cleavage of the MOM group was now readily accomplished and the resultant phenol function was exploited to bring about O-hydroxymethylation (see compound 9). Selective methylation of the phenolic hydroxyl and silylation of the primary benzylic alcohol led to compound 10.

The setting was in place to introduce the L-amino acid functionality. An allylic alcohol (compound 11) was exposed on cleavage of the pivaloate. Sharpless A.E., (6a) under the conditions shown, led to 12 in high e.e. (>95%). Azidolysis of the oxirane linkage under titanium mediated direction (6c) afforded a diol 13. To allow for building the required N-methyl 'Boc linkage, the diol was protected as its acetonide (see structure 14). From that point, the azide linkage was reductively cleaved in the presence of Boc anhydride to afford 16. Subsequent to cleavage of the TBS group and installation of a p-methoxybenzyl function, 16 was in hand. Following N-methylation, hydrolysis of the acetonide, and oxidative cleavage of the diol, (9) compound 1 was secured.

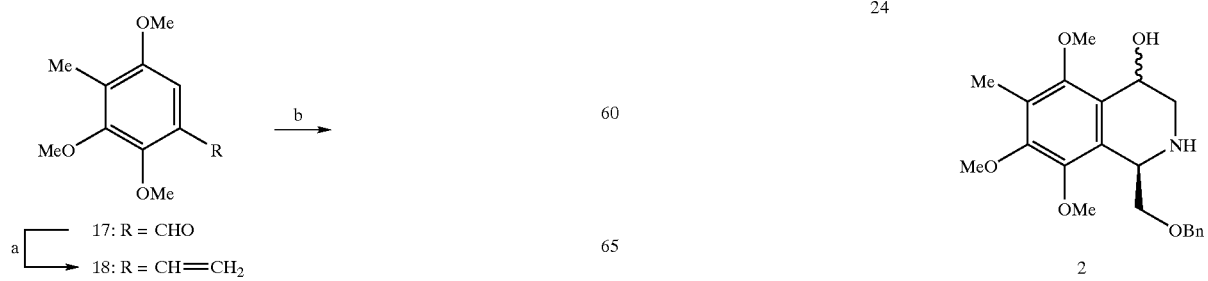

-continued a) 1.6 eq. Ph₃P═CH₂Li, THF, 0° C, 1 h, 96%; b) 1.1 eq. AD-mix-α, t-BuOH-H₂O (1:1), 0° C, 3 d, 99%; c) 1.1 eq. TsCl, pyridine-CH₂Cl₂ (1:1), 1 d, 95%; d) 2 eq. K₂CO₃, MeOH, 4 h, 95%; e) 4 eq. NaN₃, 15 eq. LiClO₄, CH₃CN, 60° C, 5 h, (2°:1° = 6.5:1); f) 1.1 eq. BnBr, 5 eq. NaH, cat. n-BuN⁺I⁻, THF, 5 h, 90% for 2 steps; g) H₂, Pd/C, EtOAc, 1.2 eq. (Boc)₂O, 5 h, 100%; h) TFA-CH₂Cl₂ (1:2), then NaHCO₃; i) 4 eq. K₂CO₃, 5 eq. BrCH₂CH(OEt)₂, CH₃CN, reflux, 3 d, 80% for 2 steps; j) 12 N HCl-THF (1:1), then NaOH, 88% (β-OH:α-OH = 4:1).

Referring to scheme 2, the synthesis of 2, with the suitable S configuration at the future C13, commenced with the known and readily available benzaldehdye 17, (10) which was converted to 18. Asymmetric di-hydroxylation (6b) of the styrene like double bond through the action of AD mix-α gave rise to 19 (>95% e.e.), from which the epoxide 20 was derived as shown. Azidolysis of the epoxide compound, under the conditions indicated, resulted in a 6.5:1 preference for attack at the benzylic, as opposed to primary carbon. The major product, 21, was converted to its O-benzyl derivative 22.

The azide linkage was reduced in the presence of Boc anhydride to afford 23. The ′Boc protection maneuver was conducted for convenience in the isolation process. Cleavage of the Boc group of 23 was followed by monoalkylation of the resultant amine function with diethylbromoacetal in high yield (see compound 24). Finally, the tetrahydroisoquinole ring was produced by the Pomerantz-Fritsch type cyclization of 24. (11) Product 2 was obtained as a 4:1 mixture of β,α stereoisomers at the future C4. As will be seen, this stereochemical issue is without consequence, since this center is destined to become a ketone in short order.

Example 1 shows that a suitably directed p-Claisen rearrangement followed by Sharpless A.E. (6a) can be used to generate a significantly functionalized tyrosine (see compound 1) analogue. Furthermore, Sharpless A.D., (6b) followed in due course by a modified Pomerantz-Fritsch cyclization, has been used to reach a valuable heavily functionalized tetrahydroisoquinoline subtype 2 in high e.e. Thus, the major subunits needed to reach the targets have been assembled by chemistry, which included p-Claisen rearrangement, asymmetric epoxidation and asymmetric dihydroxylation.

Example 2

Construction of Two Additional Chiral Subunits for Use in Preparation of the Saframycin-Ecteinascidin Series The following Schemes 3 and 4 resulted in two additional subunits, 3 and 4, respectively, which were used to prepare analogues within Saframycin-Ecteinascidin Series.

Scheme 3.

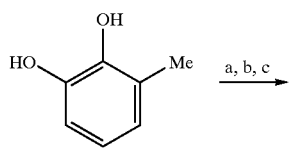

a, b, c

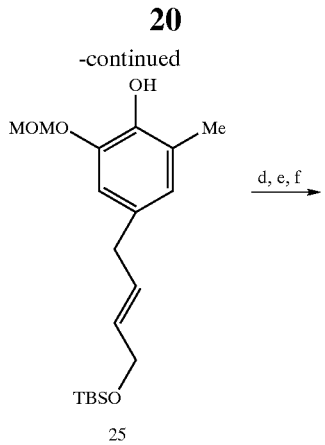

25 d, e, f

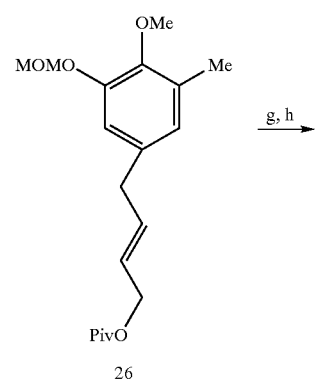

26 g, h

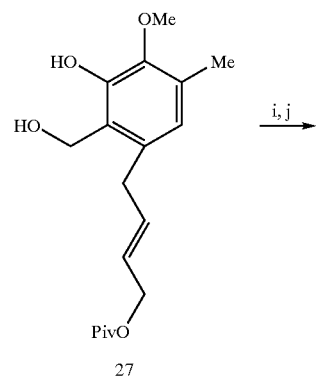

27 i, j

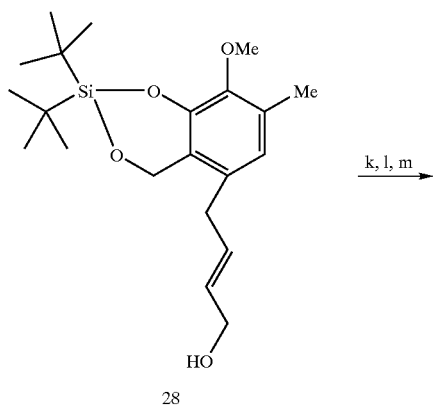

28 k, l, m

-continued

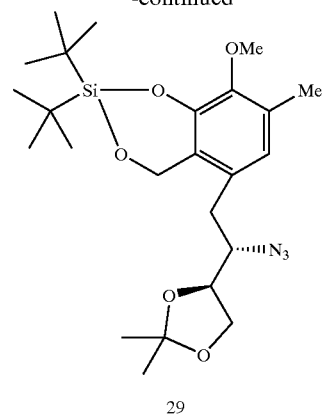

29

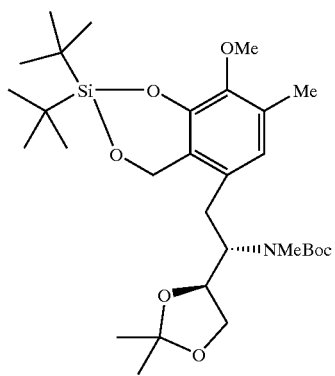

30

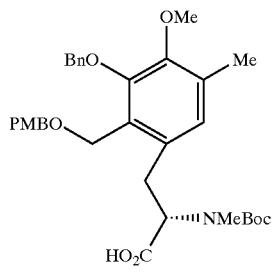

3 a) MOMCl, i-Pr₂NEt, CH₂Cl₂; b) Br⟶OTBS,
K₂CO₃, CH₃CN, reflux; c) PhNMe₂, Toluene, 210° C, 60% for 3 steps; d) MeI, K₂CO₃, CH₃CN; e) TBAF, THF; f) PivCl, Pyridine, CH₂Cl₂, 91% for 3 steps; g) 3 N HCl, THF-iPrOH; h) Et₂AlCl, (CH₂O)ₙ, CH₂Cl₂, 84% for 2 steps; i) t-Bu₂Si(OTf)₂, 2,6-Lutidine, CHCl₃; j) DIBAL-H, CH₂Cl₂, -78° C, 89% for 2 steps; k) SAE, 97%, > 95% ee; l) Ti(OiPr)₂(N₃)₂, Benzene, reflux; m) DMP, Acetone, p-TsOH, 88% for 3 steps; n) (Boc)₂O, H₂, Pd/C, EtOAc; o) MeI, NaH, THF-DMF, reflux, 95% for 2 steps; p) TBAF, THF; q) BnBr, K₂CO₃, nBu₄N⁺I⁻, CHCl₃, MeOH; r) PMBCl, NaH, nBu₄N⁺I⁻, THF, DMF, 75% for 3 steps; s) 80% AcOH, then KMnO₄, NaIO₃, Na₂CO₃, Dioxane-H₂O, 94% for 3 steps Scheme 4.

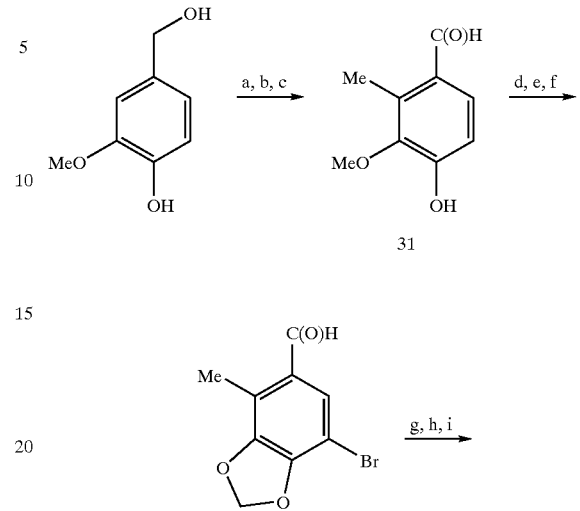

31

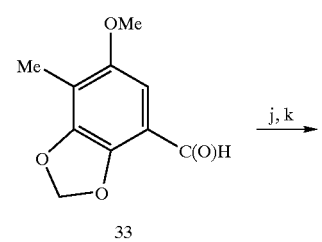

32

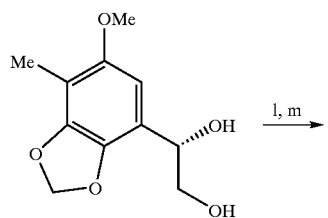

33

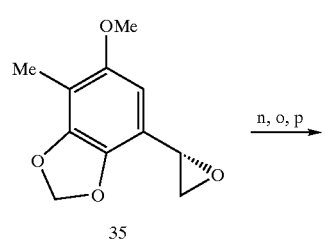

34

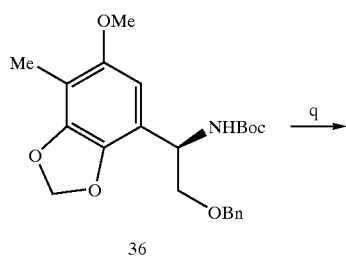

35

36

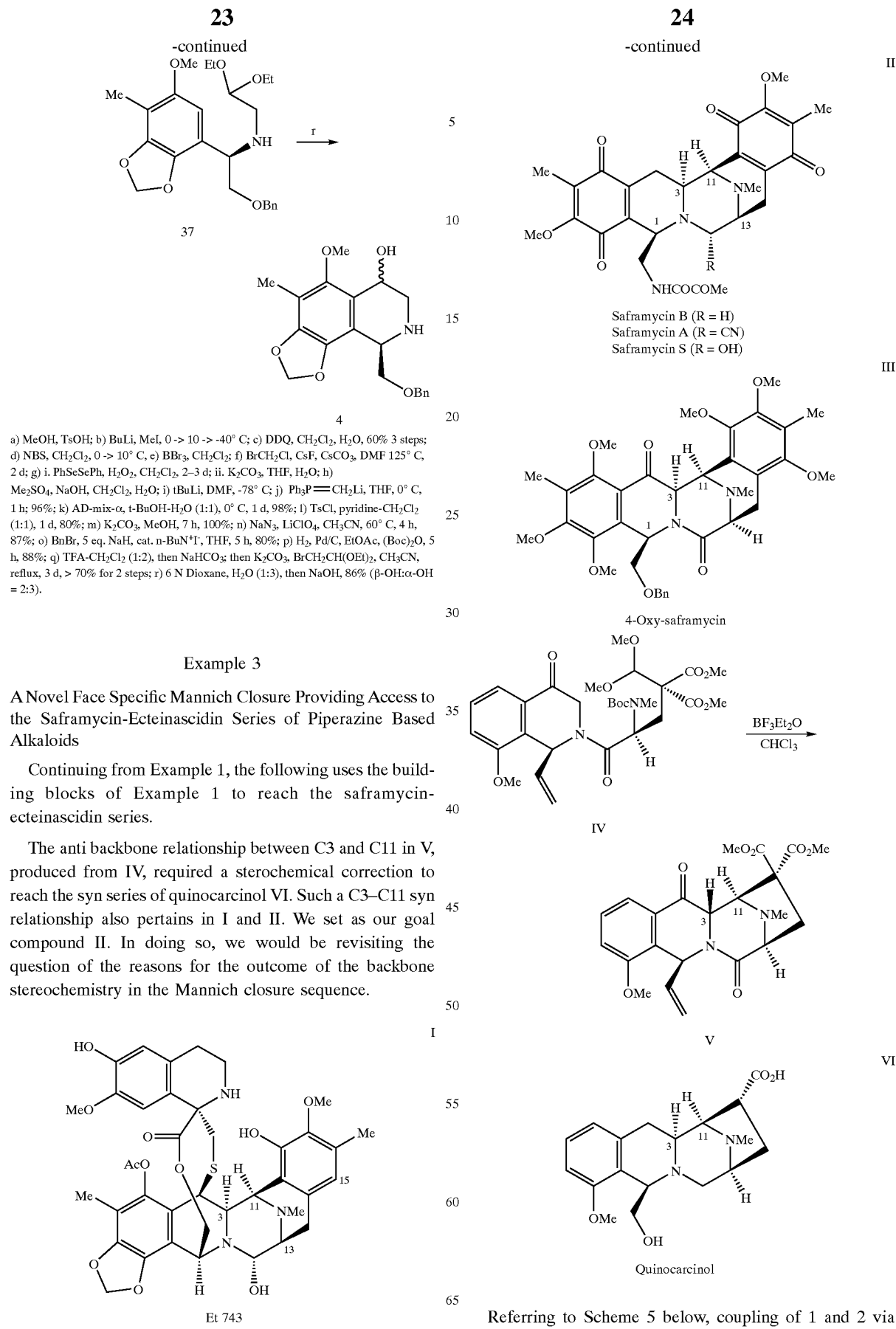

a) MeOH, TsOH; b) BuLi, MeI, 0 -> 10 -> -40° C; c) DDQ, CH$_2$Cl$_2$, H$_2$O, 60% 3 steps; d) NBS, CH$_2$Cl$_2$, 0 -> 10° C, e) BBr$_3$, CH$_2$Cl$_2$; f) BrCH$_2$Cl, CsF, CsCO$_3$, DMF 125° C, 2 d; g) i. PhSeSePh, H$_2$O$_2$, CH$_2$Cl$_2$, 2–3 d; ii. K$_2$CO$_3$, THF, H$_2$O; h) Me$_2$SO$_4$, NaOH, CH$_2$Cl$_2$, H$_2$O; i) tBuLi, DMF, -78° C; j) Ph$_3$P=CH$_2$Li, THF, 0° C, 1 h; 96%; k) AD-mix-α, t-BuOH-H$_2$O (1:1), 0° C, 1 d, 98%; l) TsCl, pyridine-CH$_2$Cl$_2$ (1:1), 1 d, 80%; m) K$_2$CO$_3$, MeOH, 7 h, 100%; n) NaN$_3$, LiClO$_4$, CH$_3$CN, 60° C, 4 h, 87%; o) BnBr, 5 eq. NaH, cat. n-BuN$^+$I$^-$, THF, 5 h, 80%; p) H$_2$, Pd/C, EtOAc, (Boc)$_2$O, 5 h, 88%; q) TFA-CH$_2$Cl$_2$ (1:2), then NaHCO$_3$; then K$_2$CO$_3$, BrCH$_2$CH(OEt)$_2$, CH$_3$CN, reflux, 3 d, > 70% for 2 steps; r) 6 N Dioxane, H$_2$O (1:3), then NaOH, 86% (β-OH:α-OH = 2:3).

Example 3

A Novel Face Specific Mannich Closure Providing Access to the Saframycin-Ecteinascidin Series of Piperazine Based Alkaloids Continuing from Example 1, the following uses the building blocks of Example 1 to reach the saframycin-ecteinascidin series.

The anti backbone relationship between C3 and C11 in V, produced from IV, required a sterochemical correction to reach the syn series of quinocarcinol VI. Such a C3–C11 syn relationship also pertains in I and II. We set as our goal compound II. In doing so, we would be revisiting the question of the reasons for the outcome of the backbone stereochemistry in the Mannich closure sequence.

Referring to Scheme 5 below, coupling of 1 and 2 via amide bond formation was accomplished through the action of BOPCl, (12) as shown, in 60–65% yield. Oxidation of the diastereomeric alcohol functions gave rise to 38 (75–80%), as a homochiral entity. To set the stage for the envisaged annulation, it was necessary to expose the aryl aldehyde function from its protected benzyl alcohol precursor. Following deprotection and oxidation, the homochiral 39, bearing the strategic aldehyde, was in hand. However, attempts to reach III by means of a 3-point-attachment of a formic acid equivalent were unsuccessful. Only with aromatic aldehyde in place was the cyclization realized.

In the event, exposure of compound 39 to the action of formic acid accomplished cleavage of the 'Boc group, thereby triggering Mannich-like double closure to produce 40 (which is also III) (75%) and 41 (17%). These products differ only in the "solvolytic" state of the primary center. In a subsequent step, 40 was converted to 41. Characterization of 40 and 41 by extensive NMR measurements (including COSY, ROESY, HMQC and HMBC techniques) established an unexpected and most welcome result. Not only had cyclization occurred, but also the piperazinone ring had been elaborated with the syn C3–C11 backbone stereochemical relationship required for I and II. The stereochemistry assigned to 40 (III) and 41 was verified by a crystallographic determination at a later stage of the synthetic sequence.

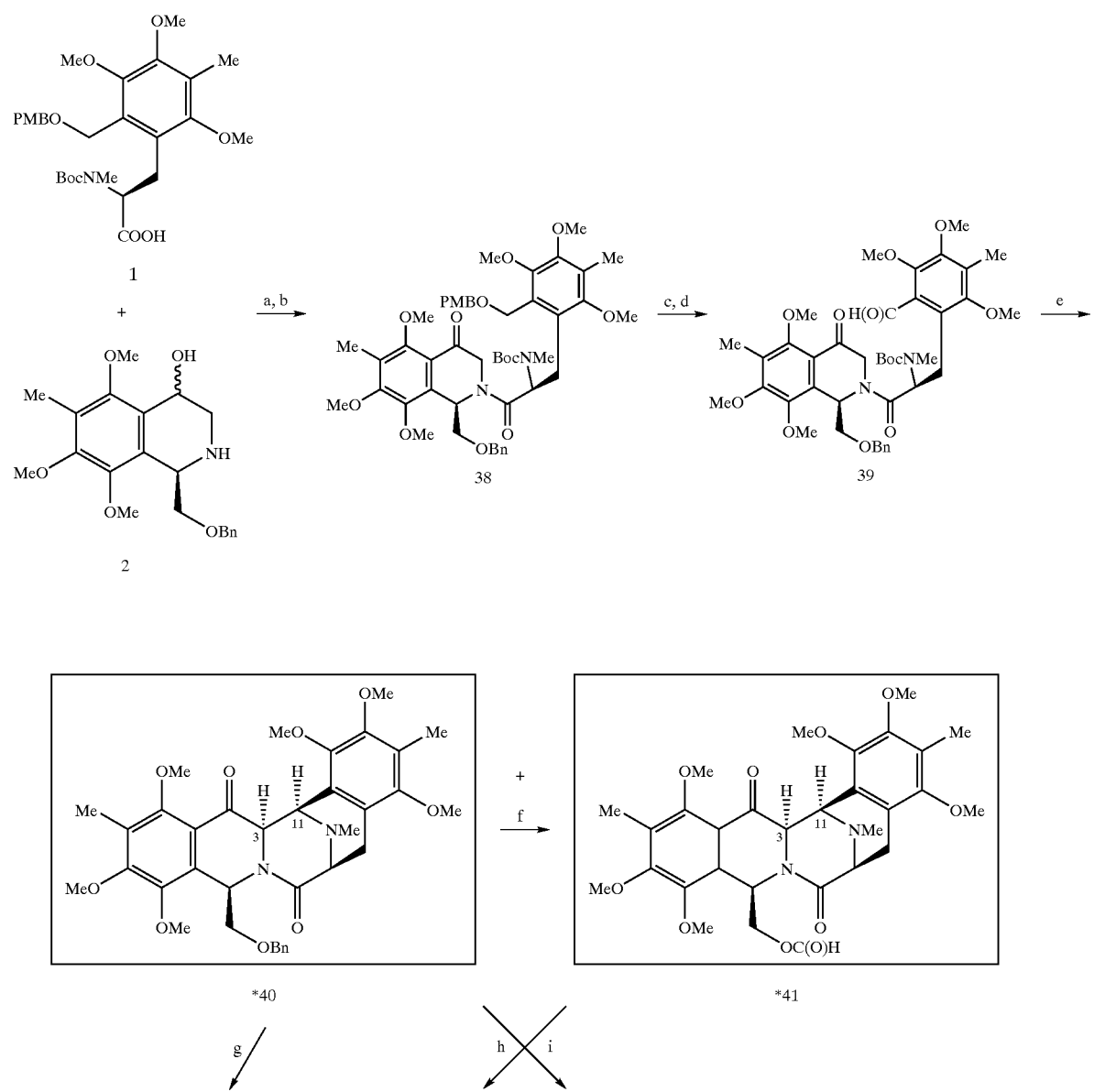

Scheme 5.

-continued
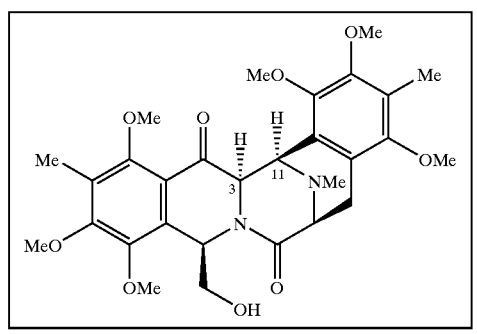
*42
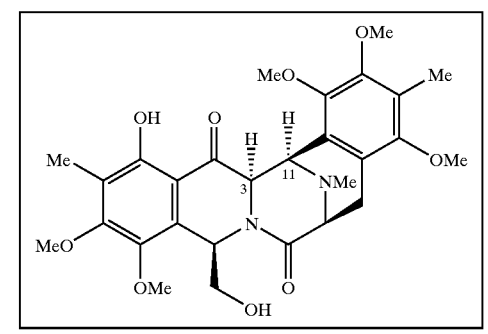
*43
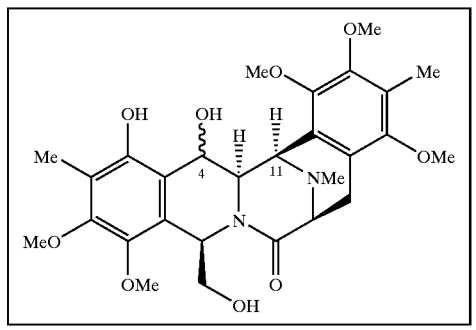
44 (α-OH)
*45 (β-OH)
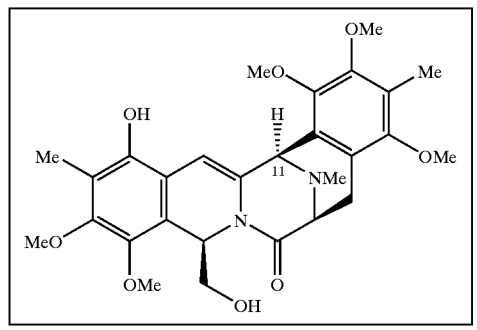
46
40 →l→ 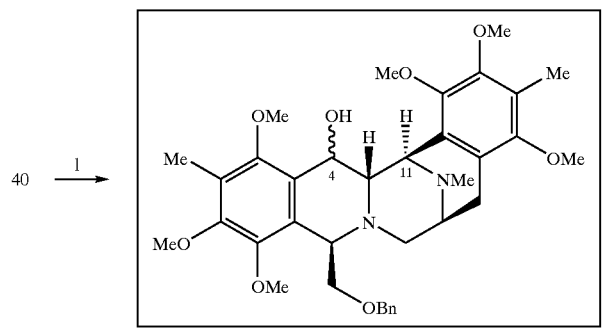
47 (α-OH)
*48 (β-OH) major
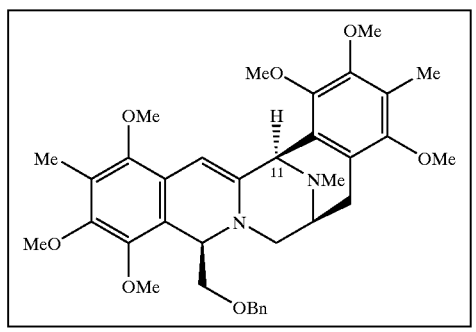
*49
a) 1.1 eq. BOPCl, 2.5 eq. Et₃N, CH₂Cl₂, 10 h, 63%; b) 1.5 eq. Dess-Martin periodinate, CH₂Cl₂, 30 min, 78%; c) 1.5 eq. DDQ, CH₂Cl₂-buffer 7.0-H₂O (20:1:1), 3 h, 84%; d) 2 eq. NMO, cat. TPAP, m.s. 4Å, CH₂Cl₂, 30 min, 84%; e) formic acid, reflux, 10 h, 75% for 40, 17% for 41, f) formic acid, reflux; g) H₂, Pd/C, EtOAc, 5 h, > 50%; h) NaHCO₃, MeOH, > 50%; i) BBr₃, CH₂Cl₂, 78° C, ~80%; j) NaBH₄, MeOH, 0° C., ~50%; k) CSA, Toluene, reflux, 62% for 49; l) AlH₃, THF, 0° C. -> r.t., ~70%.

Example 4
Synthesis of analogue 55 within the Saframycin-Ecteinascidin Series—Scheme 6
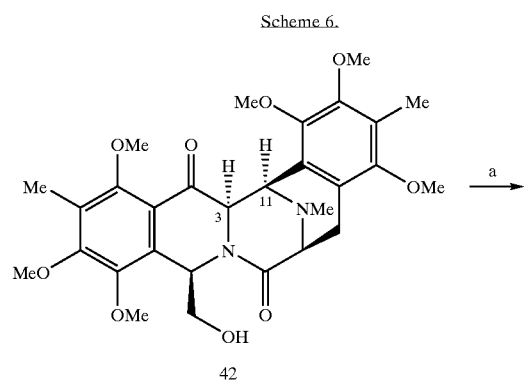
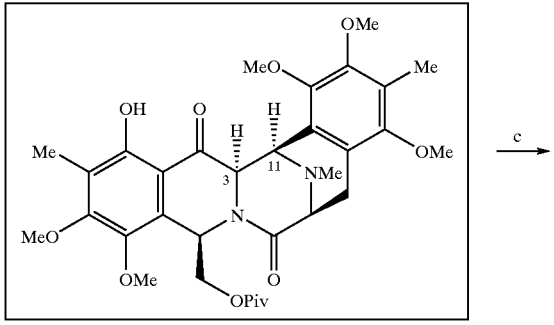
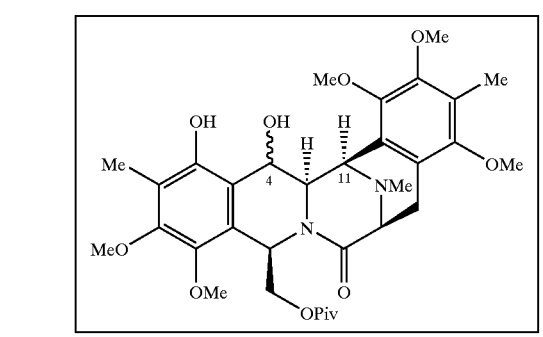
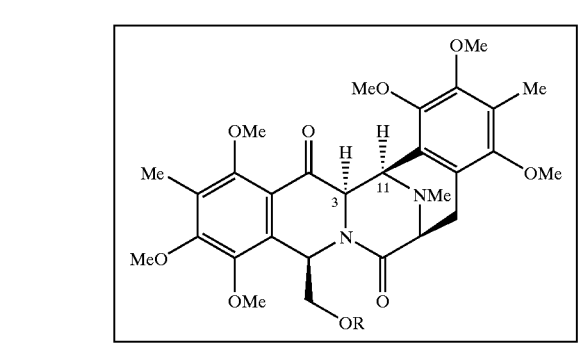
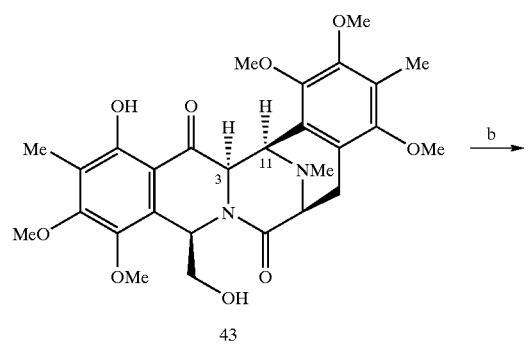
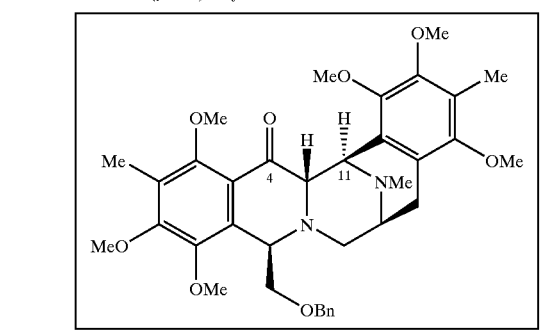
a) AcO₂, Pyridine, CH₂Cl₂, ~70% for 50; or TBSCl, Imidazole, DMAP (Cat.), ~70% for 51; b) PivCl Pyridine, CH₂Cl₂, ~60%; c) NaBH₄, MeOH, 0° C., ~50%; d) Dess-Martin/periodinane Ch₂Cl₂, ~70%.

Example 5
Synthesis of analogue 63 within the Saframycin-Ecteinascidin Series using subunits 1 and 4—Scheme 7
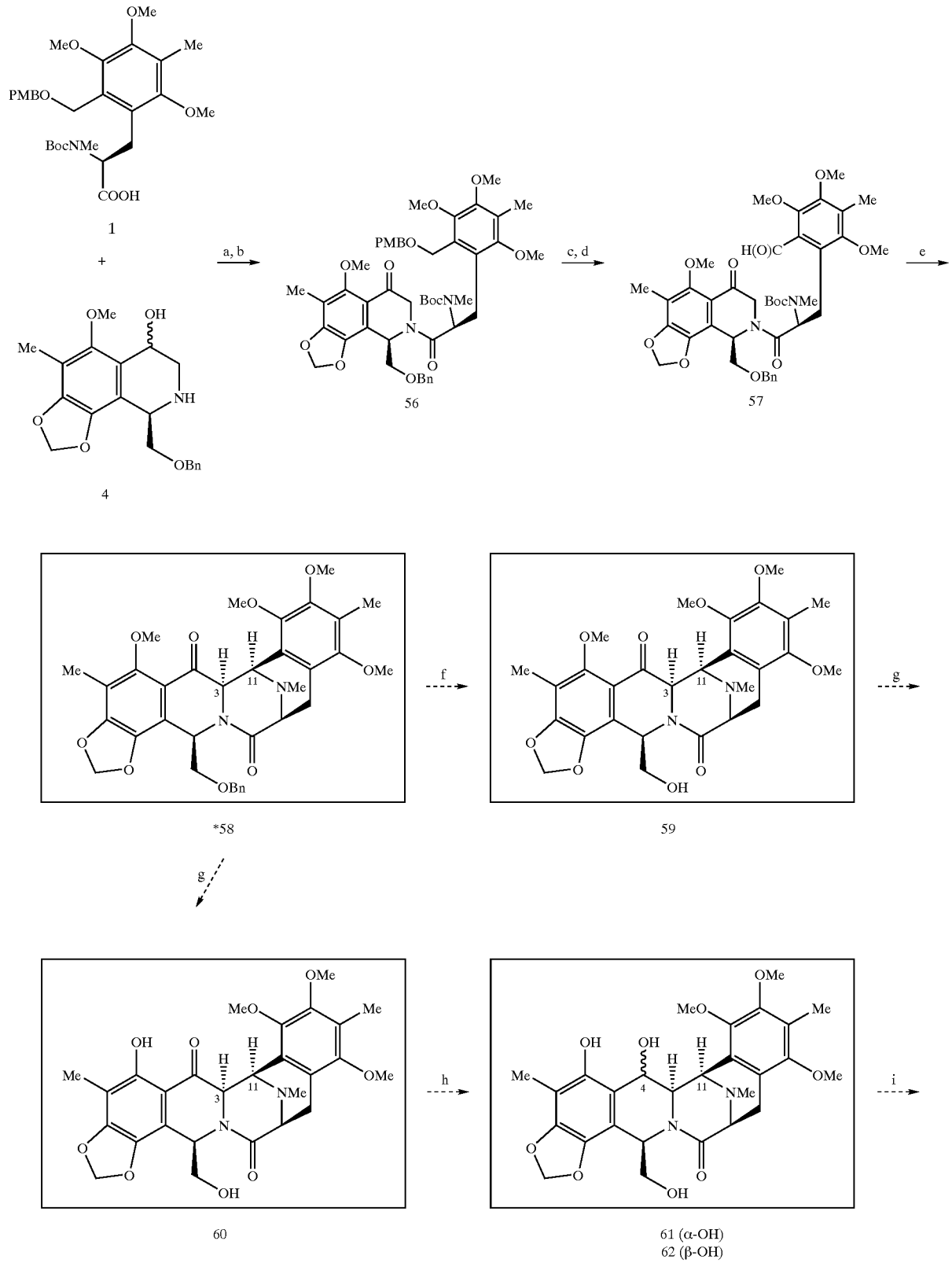

-continued

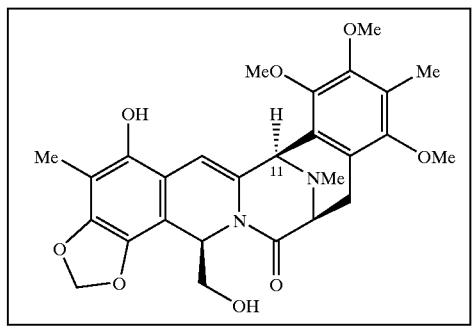

63 a) 1.1 eq. BOPCl, 2.5 eq. Et$_3$N, CH$_2$Cl$_2$, 10 h; b) 1.5 eq. Dess-Martin periodinane, CH$_2$Cl$_2$, 30 min, ~46% for 2 steps; c) 1.5 eq. DDQ, CH$_2$Cl$_2$-buffer 7.0-HO (20:1:1), 3 h, 80%; d) 2 eq. NMO, cat. TPAP, m.s. 4 Å, CH$_2$Cl$_2$, 30 min, 80%; e) formic acid, rflux, 1 h, 60–70%; f) H$_2$, Pd/C, EtOAc, 5 h; g) BBr$_3$, CH$_2$Cl$_2$, -78° C.; h) NaBH$_4$, MeOH, 0° C.; i) CSA, Toluene, reflux.

Example 6
Synthesis of analogues within the Saframycin-Ecteinascidin Series using subunits 3 and 4—Scheme 8

Scheme 8.

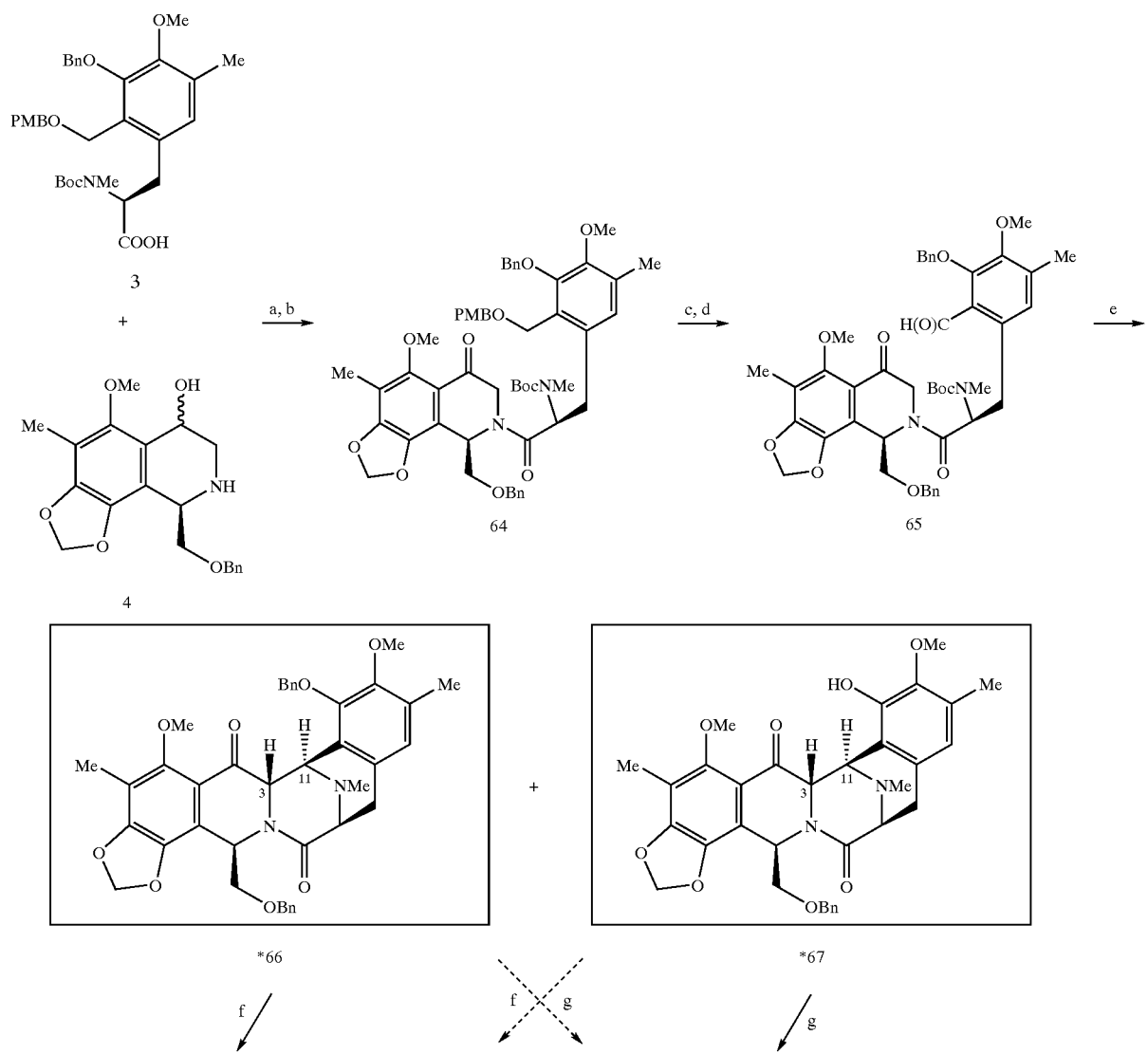

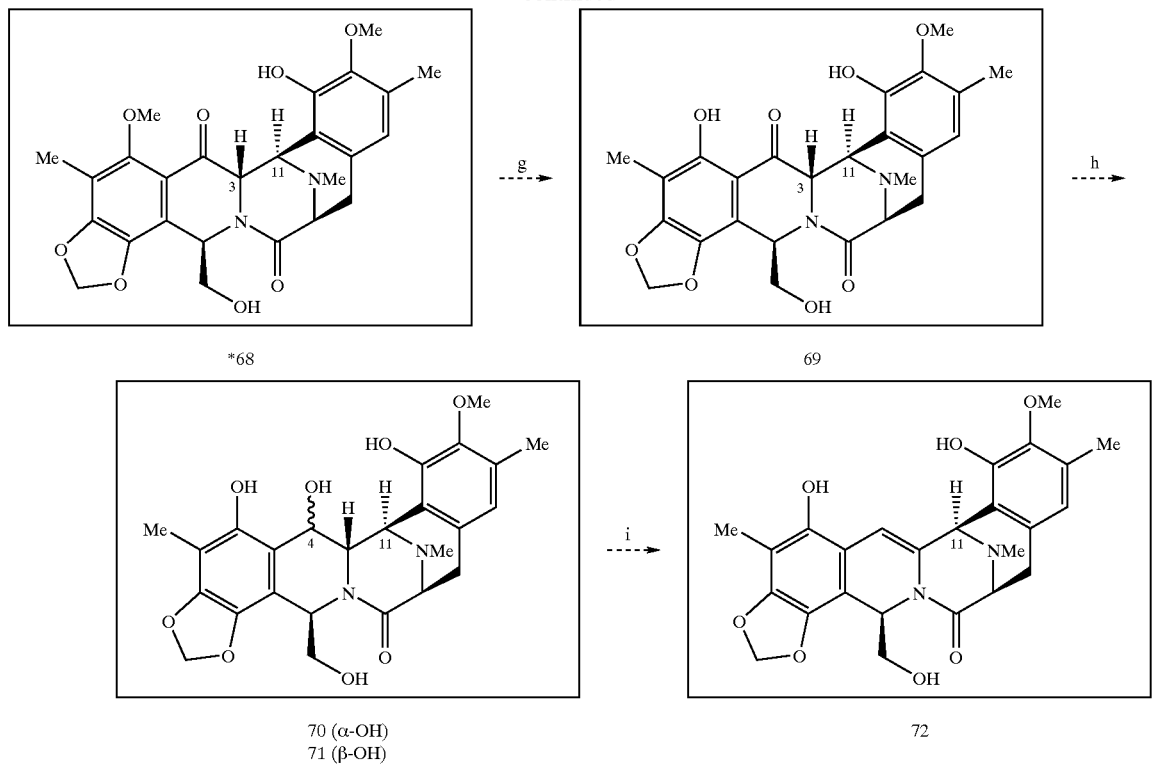
a) 1.1 eq. BOPCl, 2.5 eq. Et₃N, CH₂Cl₂, 10 h; b) 1.5 eq. Dess-Martin periodinane, Ch₂Cl₂, 30 min. ~48% for 2 steps; c) 1.5 eq. DDQ, CH₂Cl₂-buffer 7.0-H₂O (20:1:1), 3 h, 80%; d) 2 eq. NMO, cat. TPAP, m.s 4 A, CH₂Cl₂, 30 min. 80%; e) formic acid, reflux, 1 h, 60–70%, (66:67 = ~5:1); f) H₂, Pd/C, EtOAc, 5 H, >90%; g) BBr₃, Ch₂Cl₂, -78° C.; h) NaBH₄ MeOH, 0° C.; i) CSA, Toluene, reflux.
Example 7
Synthesis of analogues within the Saframycin-Ecteinascidin Series using sub units 3 and 2—Scheme 9
Scheme 9.
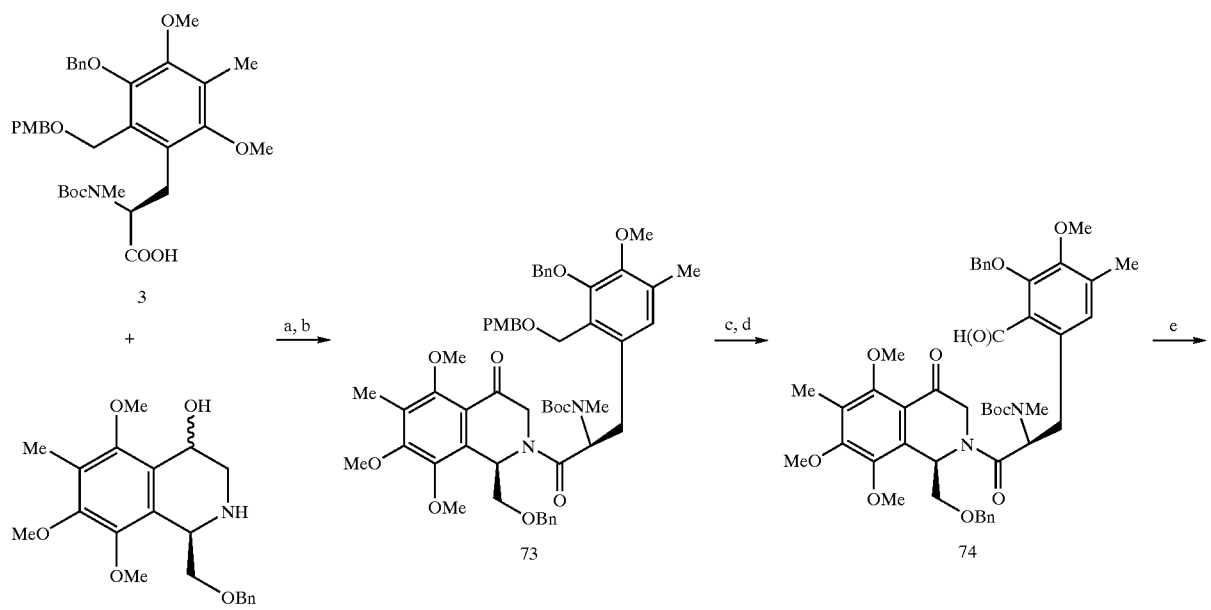

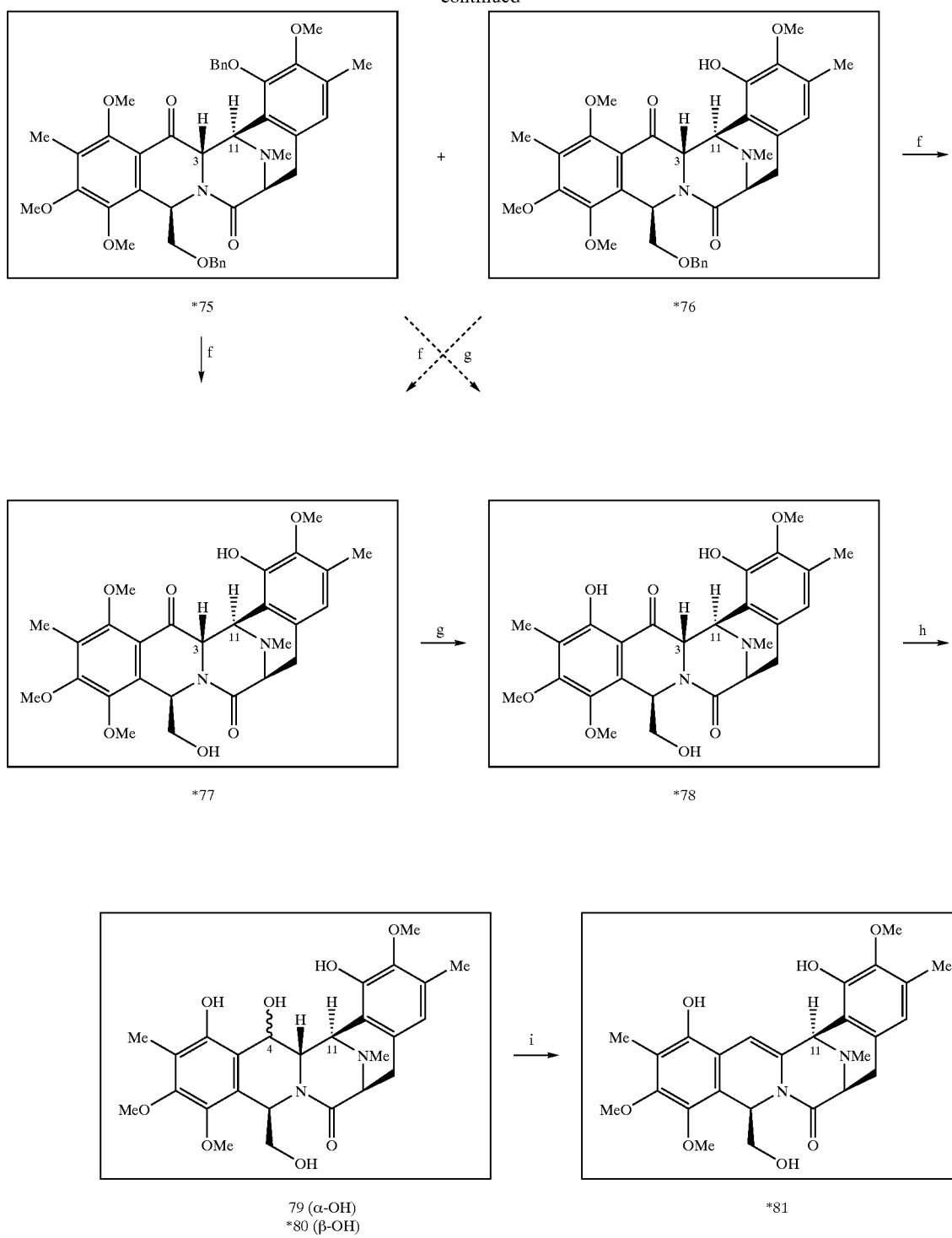
a) 1.1. eq. BOPCl, 2.5 eq. ET₃N, CH₂CL₂, 10 h; b) 1.5 eq. Dess-Martin periodinane, CH₂Cl₂, 30 min, ~50% for 2 steps; c) 1.5 eq. DDQ, CH₂CL₂-buffer 7.0-H₂O (20:1:1), 3 h, 70–80%; d) 2 eq. NMO, cat. TPAP, m.s. 4 A, CH₂Cl₂, 30 min, 70–80%; e) formic acid, reflux, 1 h, 60–70% (75:76 = 5:1); f) H₂, Pd/C, EtOAc, 5 h; g) BBr₃, CH₂Cl₂, -78° C. 93–99%; h) NaBH₄, MeOH, 0° C., 50%; i) CSA, Toluene, reflux, 92%.

Example 8
Synthesis of analogues within the Saframycin-Ecteinascidin Series—Scheme 10
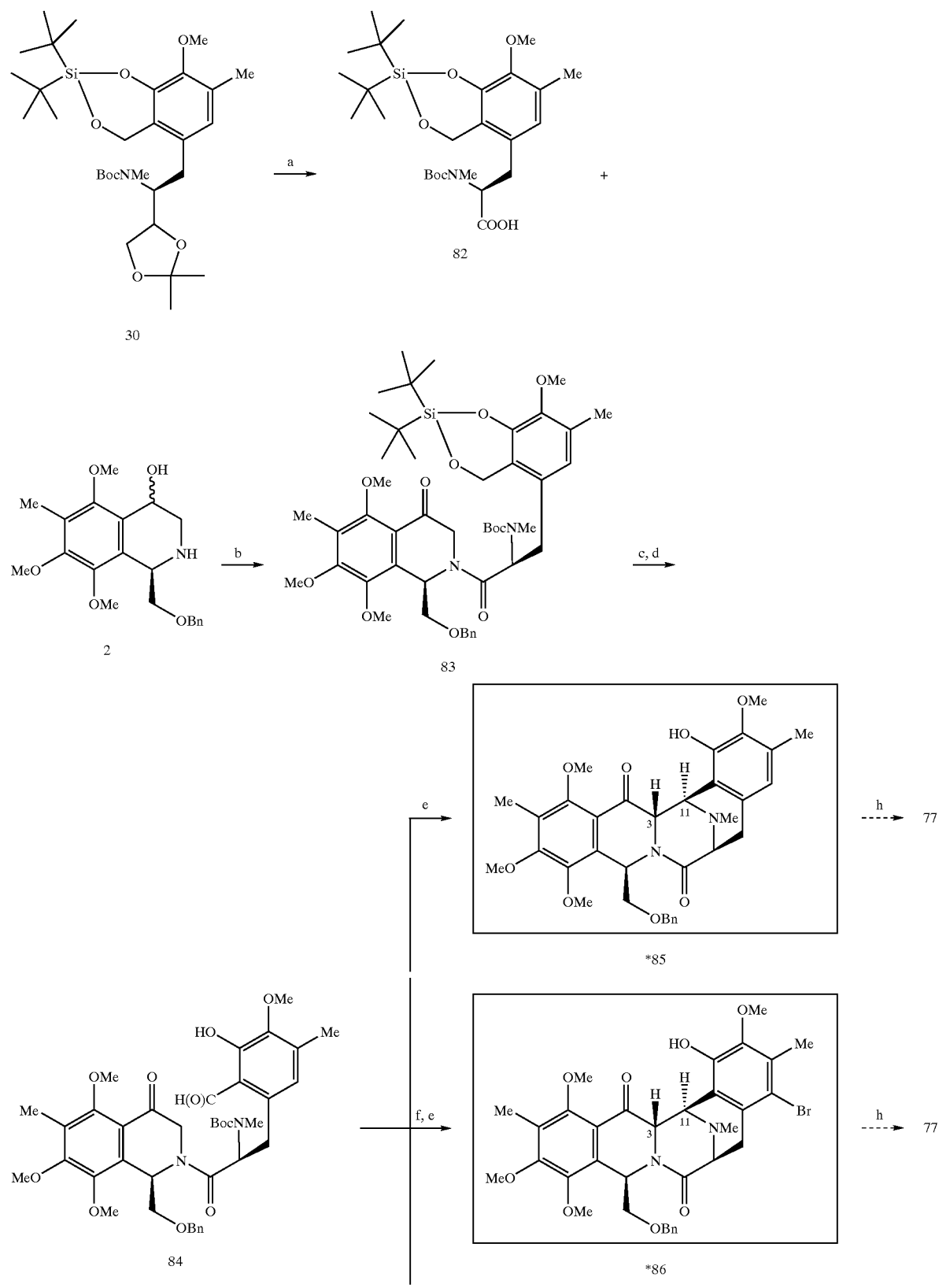

-continued
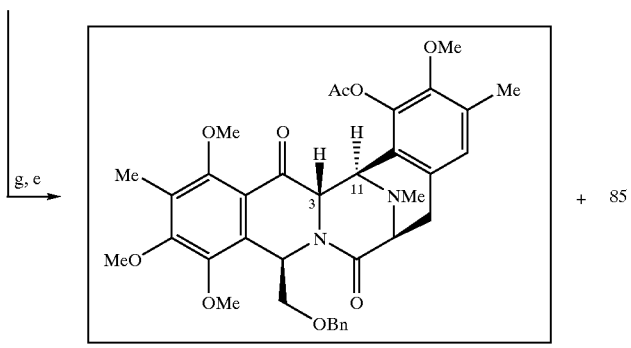
*87
a) 80% AcOH, 10 h, then KMnO₄, NaIO₄, Na₂CO₃; Dioxane, H₂O, > 90%; b) i. 1.1 eq. BOPCl, 2.5 eq. ET₃N, CH₂Cl₂, 10 h; ii. Dess-Martin periodinane, CH2Cl2, 60% for 2 steps; c) HF-Py, THF, AcOH (Cat), 93%; d) MnO₂, acetone, 72%; e) formic acid, reflux, 1 h, 60–70%; f) Br₂ or NBS, CCl₄, ~60%; g) Ac₂O, Pyridine, Ch₂Cl₂, ~70%, (87:85 = 1:1); h) H₂, Pd/C, (Et)Ac.
Example 9
Synthesis of analogues within the Saframycin-Ecteinascidin Series—Scheme 11
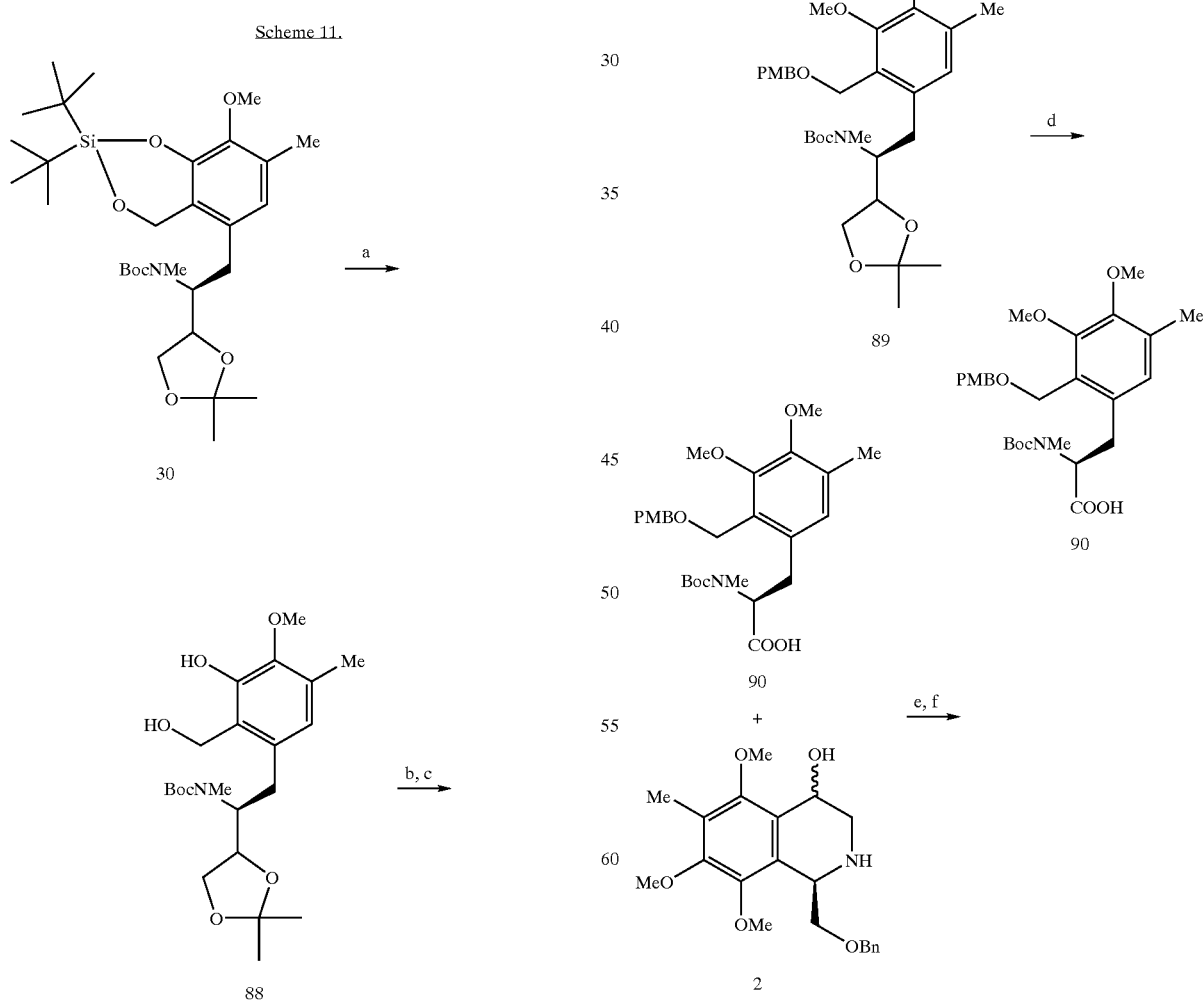

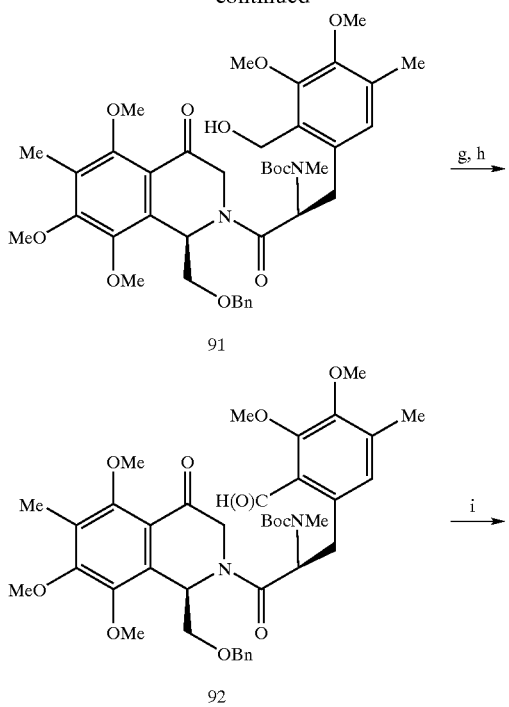

91

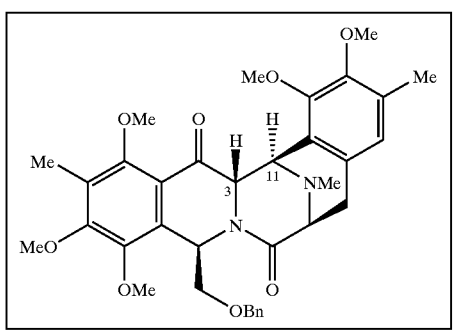

92

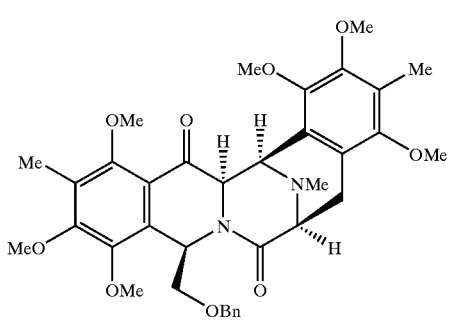

*93

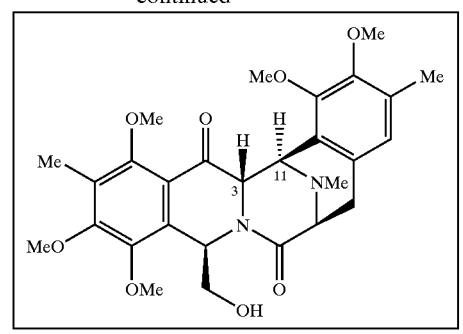

94 a) TBAF, THF, >90%; b) MeI, K$_2$CO$_3$, CHCl$_3$, MeOH, reflux, 80%; c) PMBCl, MaH, nBuN$^+$T, THF, DMF, 90%; d) 80% AcOH, 10 h, then KMnO$_4$, NaIO$_4$, Na$_2$CO$_3$, Dioxane, H$_2$O, 90% for steps; e) 1.1 eq. BOPCl, 2.5 eq. Et$_3$N, CH$_2$Cl$_2$, 10 h; f) Des-Martin periodinane, CH$_2$Cl$_2$, ~50% for 2 steps; g) DDQ, CH$_2$Cl$_2$, H$_2$O, Buffer 7.0, 85%; h) NMO, TPAP, 4 A ms, CH$_2$Cl$_2$, 70%, i) formic acid, reflux, 1 h, 60–70%; j) H$_2$, Pd/C, Et)Ac.

Mass Spectroscopy and $^1$H-NMR Data for Selected Compounds

The following table provides the $^1$H-NMR and MS data for selected compounds which are useful as cytotoxic agents:

40

$^1$H NMR (CDCl$_3$, 500 MHz) 7.24–7.10 (m, 5H), 6.14 (t, J = 3.4 Hz, 1H), 5.08 (d, J = 3.6 Hz, 1H), 4.66 (d, J = 3.1 Hz, 1H), 4.52 (d, J = 12.2 Hz, 1H), 4.32 (d, J = 12.2 Hz, 1H), 4.0–3.5 (m, 3H), 3.88 (m, 1H), 3.80 (s, 3H), 3.77 (s, 3H), 3.76 (s, 3H), 3,67 (s, 3H), 3.55 (s, 3H), 3.54 (s, 3H), 3.01 (m, 2H), 2.51 (s, 3H), 2.03 (s, 6H); HRMS (FAB+) m/z calcd for C$_{36}$H$_{42}$O$_9$N$_2$K 658.2527, found 658.2557.

-continued

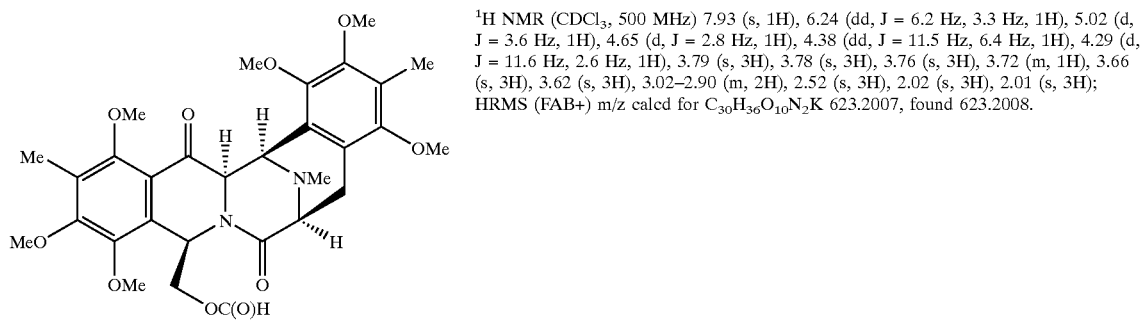

41

¹H NMR (CDCl₃, 500 MHz) 7.93 (s, 1H), 6.24 (dd, J = 6.2 Hz, 3.3 Hz, 1H), 5.02 (d, J = 3.6 Hz, 1H), 4.65 (d, J = 2.8 Hz, 1H), 4.38 (dd, J = 11.5 Hz, 6.4 Hz, 1H), 4.29 (d, J = 11.6 Hz, 2.6 Hz, 1H), 3.79 (s, 3H), 3.78 (s, 3H), 3.76 (s, 3H), 3.72 (m, 1H), 3.66 (s, 3H), 3.62 (s, 3H), 3.02–2.90 (m, 2H), 2.52 (s, 3H), 2.02 (s, 3H), 2.01 (s, 3H); HRMS (FAB+) m/z calcd for $C_{30}H_{36}O_{10}N_2K$ 623.2007, found 623.2008.

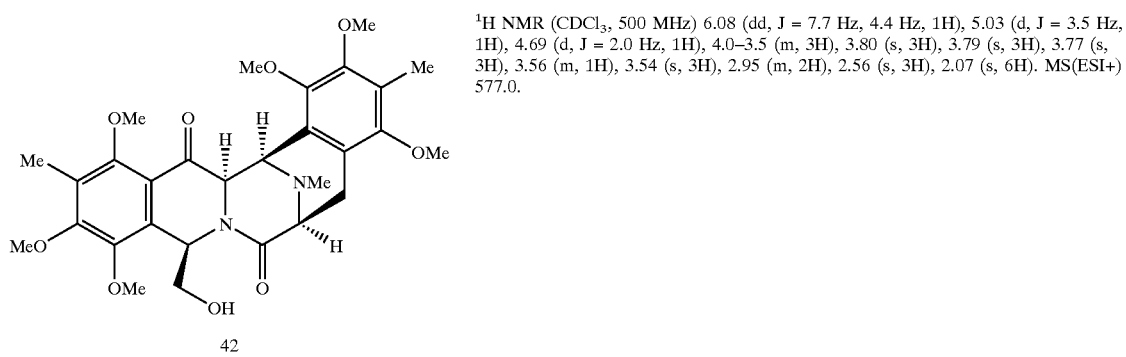

42

¹H NMR (CDCl₃, 500 MHz) 6.08 (dd, J = 7.7 Hz, 4.4 Hz, 1H), 5.03 (d, J = 3.5 Hz, 1H), 4.69 (d, J = 2.0 Hz, 1H), 4.0–3.5 (m, 3H), 3.80 (s, 3H), 3.79 (s, 3H), 3.77 (s, 3H), 3.56 (m, 1H), 3.54 (s, 3H), 2.95 (m, 2H), 2.56 (s, 3H), 2.07 (s, 6H). MS(ESI+) 577.0.

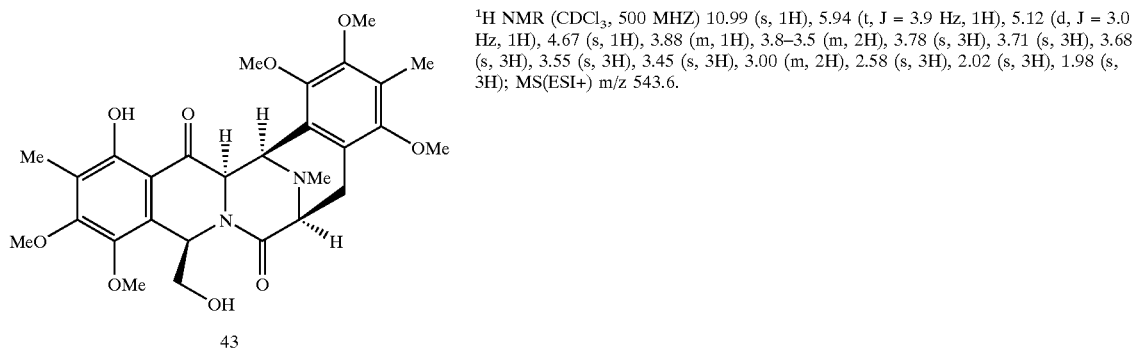

43

¹H NMR (CDCl₃, 500 MHZ) 10.99 (s, 1H), 5.94 (t, J = 3.9 Hz, 1H), 5.12 (d, J = 3.0 Hz, 1H), 4.67 (s, 1H), 3.88 (m, 1H), 3.8–3.5 (m, 2H), 3.78 (s, 3H), 3.71 (s, 3H), 3.68 (s, 3H), 3.55 (s, 3H), 3.45 (s, 3H), 3.00 (m, 2H), 2.58 (s, 3H), 2.02 (s, 3H), 1.98 (s, 3H); MS(ESI+) m/z 543.6.

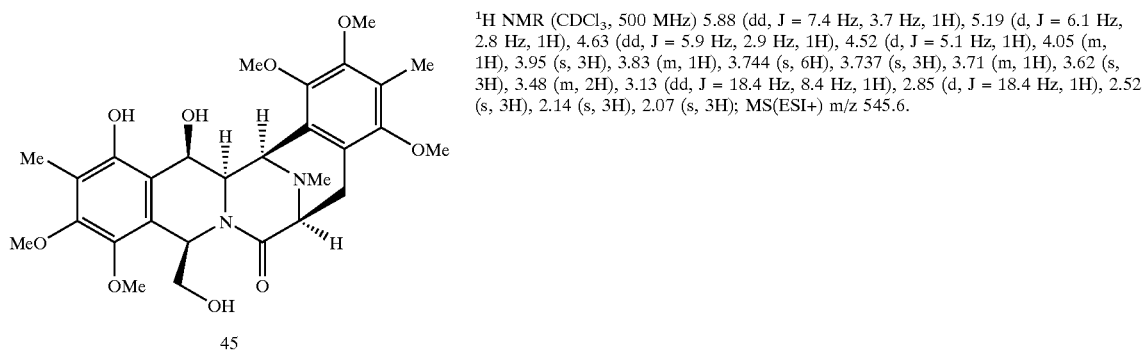

45

¹H NMR (CDCl₃, 500 MHz) 5.88 (dd, J = 7.4 Hz, 3.7 Hz, 1H), 5.19 (d, J = 6.1 Hz, 2.8 Hz, 1H), 4.63 (dd, J = 5.9 Hz, 2.9 Hz, 1H), 4.52 (d, J = 5.1 Hz, 1H), 4.05 (m, 1H), 3.95 (s, 3H), 3.83 (m, 1H), 3.744 (s, 6H), 3.737 (s, 3H), 3.71 (m, 1H), 3.62 (s, 3H), 3.48 (m, 2H), 3.13 (dd, J = 18.4 Hz, 8.4 Hz, 1H), 2.85 (d, J = 18.4 Hz, 1H), 2.52 (s, 3H), 2.14 (s, 3H), 2.07 (s, 3H); MS(ESI+) m/z 545.6.

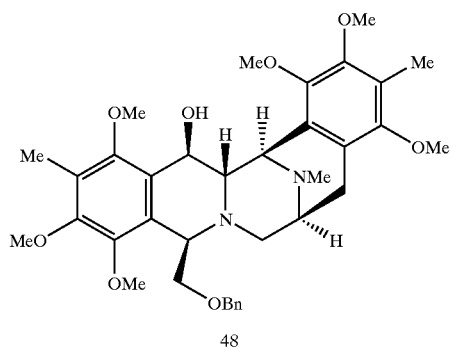

48

$^1$H NMR (CDCl$_3$, 500 MHz) 7.30–7.15 (m, 5H), 5.08 (s, 1H), 4.45 (s, 2H), 4.26 (m, 2H), 3.90–3.70 (m, 2H), 3.85 (s, 3H), 3.71 (s, 3H), 3.63 (s, 6H), 3.61 (s, 3H), 3.583 (s, 3H), 3.577 (s, 3H), 3.56 (m, 1H), 3.54 (d, J = 10.2 Hz, 1H), 3.35 (br s, 1H), 3.24 (d, J = 12.4 Hz, 1H), 3.15 (br s, 1H), 3.00 (dd, J = 18.3 Hz, 8.3 Hz, 1H), 2.78 (d, J = 18.4 Hz, 1H), 2.20 (s, 3H), 2.15 (s, 6H); MS(ESI+) m/z 635.3.

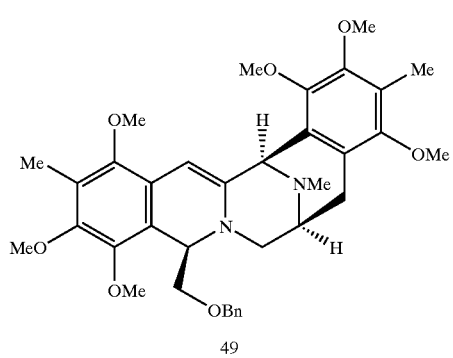

49

$^1$H NMR (CDCl$_3$, 500 MHz) 7.28–7.16 (m, 5H), 5.09 (dd, J = 8.7 Hz, 4.1 Hz, 1H), 5.45 (s, 2H), 4.28 (d, J = 5.2 Hz, 2H), 4.18 (s, 1H), 3.82 (s, 3H), 3.68 (s, 3H), 3.63 (s, 3H), 3.60 (s, 3H), 3.58 (s, 3H), 3.57 (s, 3H), 3.84–3.38 (m, 5H), 3.24 (m, 1H), 3.06 (m, 2H), 2.66 (d, J = 17.6 Hz, 1H), 2.18 (s, 3H), 2.02 (s, 6H); MS (APCI+) m/z 604.0.

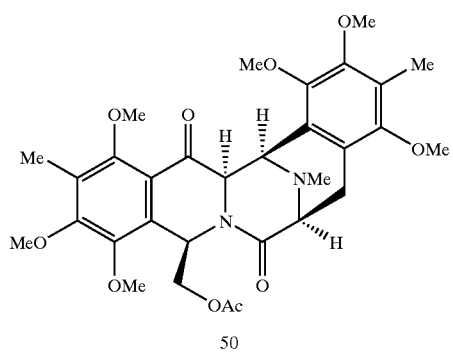

50

$^1$H NMR (CDCl$_3$, 500 MHz) 6.18 (t, J = 2.9 Hz, 1H), 5.04 (d, J = 3.5 Hz, 1H), 4.63 (d, J = 3.0 Hz, 1H), 4.38 (dd, J = 11.6 Hz, 4.6 Hz, 1H), 4.2 (dd, J = 11.6 Hz, 2.6 Hz, 1H), 3.67 (s, 3H), 3.79 (s, 3H), 3.78 (s, 3H), 3.76 (s, 3H), 3.71 (d, J = 6.5 Hz, 1H), 3.57 (s, 3H), 3.55 (s, 3H), 2.98 (m, 2H), 2.53 (s, 3H), 2.02 (s, 3H), 2.01 (s, 3H), 1.92 (s, 3H); MS(ESI+) m/z 599.5.

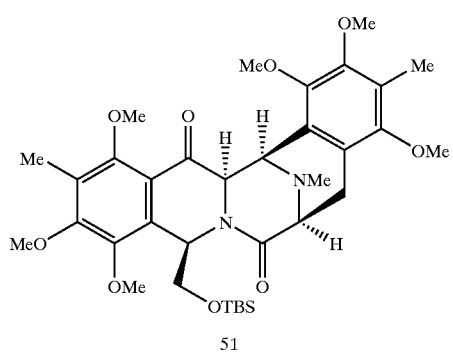

51

$^1$H NMR (CDCl$_3$, 400 MHz) 5.92 (s, 1H), 5.10 (s, 1H), 4.63 (s, 1H), 4.08 (m, 1H), 3.89 (m, 1H), 3.81 (s, 3H), 3.76 (s, 3H), 3.75 (s, 3H), 3.66 (m, 1H), 3.51 (s, 3H), 3.44 (s, 3H), 2.97 (m, 2H), 2.54 (s, 3H), 2.02 (s, 6H); MS(ESI+) m/z 670.8.

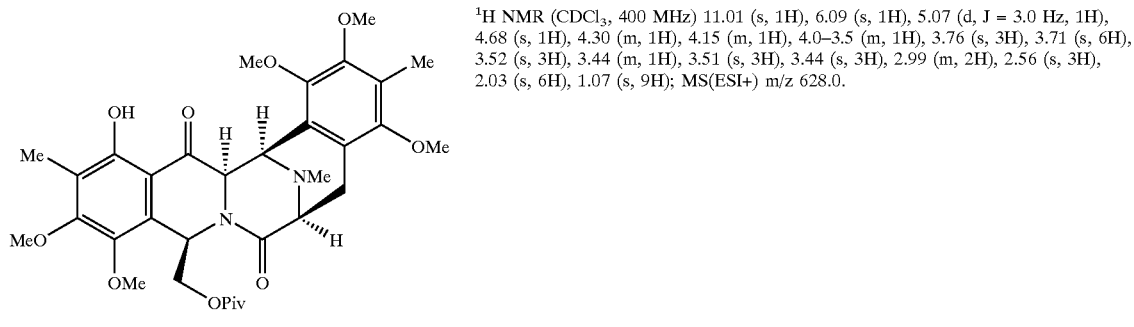

52

$^1$H NMR (CDCl$_3$, 400 MHz) 11.01 (s, 1H), 6.09 (s, 1H), 5.07 (d, J = 3.0 Hz, 1H), 4.68 (s, 1H), 4.30 (m, 1H), 4.15 (m, 1H), 4.0–3.5 (m, 1H), 3.76 (s, 3H), 3.71 (s, 6H), 3.52 (s, 3H), 3.44 (m, 1H), 3.51 (s, 3H), 3.44 (s, 3H), 2.99 (m, 2H), 2.56 (s, 3H), 2.03 (s, 6H), 1.07 (s, 9H); MS(ESI+) m/z 628.0.

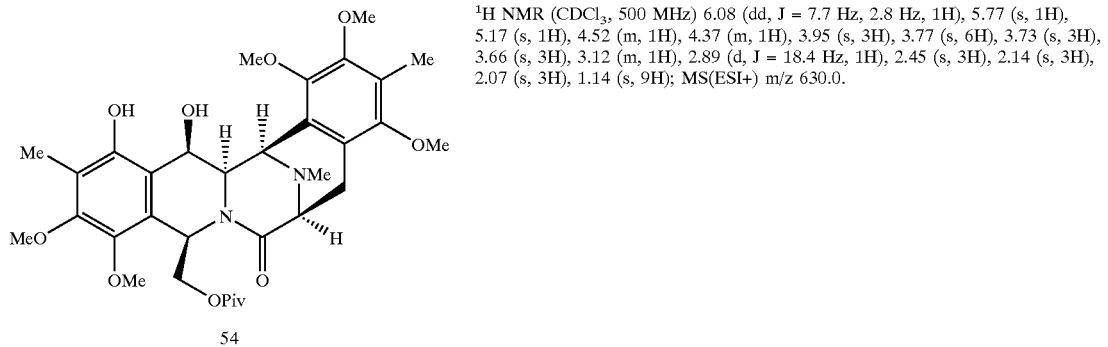

54

$^1$H NMR (CDCl$_3$, 500 MHz) 6.08 (dd, J = 7.7 Hz, 2.8 Hz, 1H), 5.77 (s, 1H), 5.17 (s, 1H), 4.52 (m, 1H), 4.37 (m, 1H), 3.95 (s, 3H), 3.77 (s, 6H), 3.73 (s, 3H), 3.66 (s, 3H), 3.12 (m, 1H), 2.89 (d, J = 18.4 Hz, 1H), 2.45 (s, 3H), 2.14 (s, 3H), 2.07 (s, 3H), 1.14 (s, 9H); MS(ESI+) m/z 630.0.

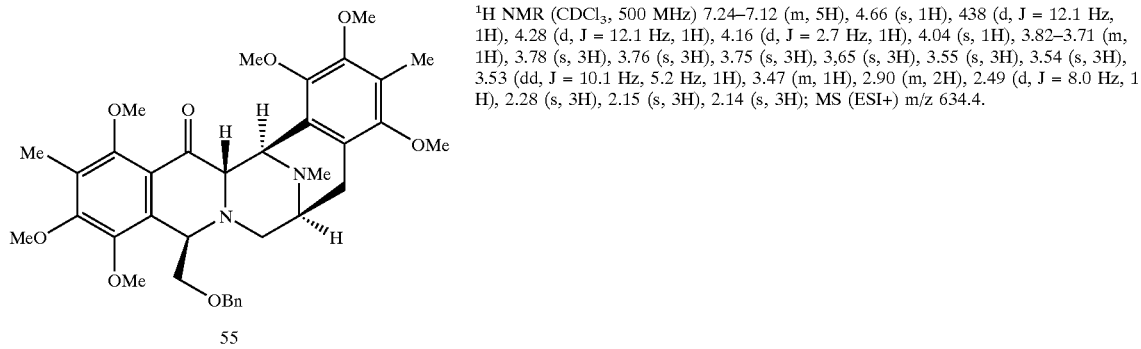

55

$^1$H NMR (CDCl$_3$, 500 MHz) 7.24–7.12 (m, 5H), 4.66 (s, 1H), 438 (d, J = 12.1 Hz, 1H), 4.28 (d, J = 12.1 Hz, 1H), 4.16 (d, J = 2.7 Hz, 1H), 4.04 (s, 1H), 3.82–3.71 (m, 1H), 3.78 (s, 3H), 3.76 (s, 3H), 3.75 (s, 3H), 3.65 (s, 3H), 3.55 (s, 3H), 3.54 (s, 3H), 3.53 (dd, J = 10.1 Hz, 5.2 Hz, 1H), 3.47 (m, 1H), 2.90 (m, 2H), 2.49 (d, J = 8.0 Hz, 1H), 2.28 (s, 3H), 2.15 (s, 3H), 2.14 (s, 3H); MS (ESI+) m/z 634.4.

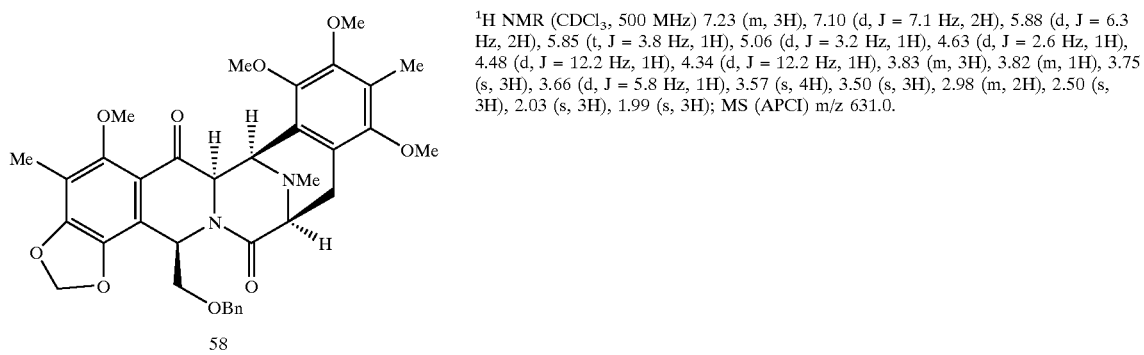

58

$^1$H NMR (CDCl$_3$, 500 MHz) 7.23 (m, 3H), 7.10 (d, J = 7.1 Hz, 2H), 5.88 (d, J = 6.3 Hz, 2H), 5.85 (t, J = 3.8 Hz, 1H), 5.06 (d, J = 3.2 Hz, 1H), 4.63 (d, J = 2.6 Hz, 1H), 4.48 (d, J = 12.2 Hz, 1H), 4.34 (d, J = 12.2 Hz, 1H), 3.83 (m, 3H), 3.82 (m, 1H), 3.75 (s, 3H), 3.66 (d, J = 5.8 Hz, 1H), 3.57 (s, 4H), 3.50 (s, 3H), 2.98 (m, 2H), 2.50 (s, 3H), 2.03 (s, 3H), 1.99 (s, 3H); MS (APCI) m/z 631.0.

-continued

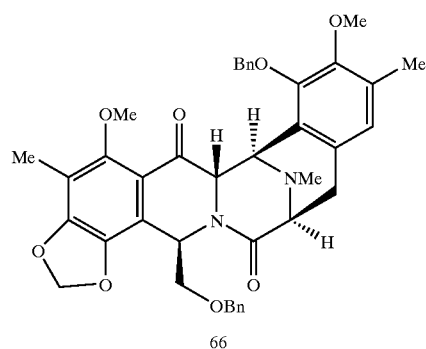

66

¹H NMR (CDCl₃, 500 MHz) 7.50 (d, J = 7.5 Hz, 2H), 7.32 (m, 3H), 7.10 (m, 3H), 6.79 (d, J = 7.4 Hz, 2H), 6.64 (s, 1H), 6.06 (m, 1H), 5.94 (s, 2H), 5.17 (s, 1H), 5.12 (d, J = 10.9 Hz, 1H), 5.01 (d, J = 10.8 Hz, 1H), 4.52 (s, 1H), 4.11 (m, 1H), 4.01 (d, J = 9.4 Hz, 1H), 3.83 (s, 3H), 3.66 (m, 2H), 3.60 (s, 3H), 3.59 (m, 1H), 3.13 (m, 1H), 2.78 (d, J = 17.3 Hz, 1H), 2.25 (s, 3H), 2.18 (s, 3H), 2.14 (s, 3H); MS (FAB+) m/z 667.4.

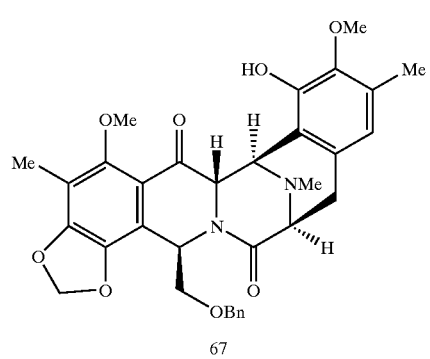

67

¹H NMR (CDCl₃, 500 MHz) 7.16 (m, 3H), 6.82 (m, 2H), 6.45 (s, 1H), 6.10 (dd, J = 6.4 Hz, 3.5 Hz, 1H), 5.97 (d, J = 2.0 Hz, 2H), 5.67 (s, 1H), 5.24 (s, 1H), 4.56 (s, 1H), 4.10 (m, 2H), 3.85 (s, 3H), 3.70–3.60 (m, 2H), 3.68 (s, 3H), 3.14 (dd, J = 17.3 Hz, 7.8 Hz, 1H), 2.80 (d, J = 17.3 Hz, 1H), 2.40 (s, 3H), 2.20 (s, 3H), 2.14 (s, 3H); MS (ESI+) m/z 587.1.

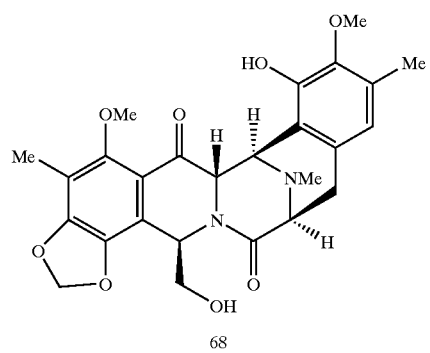

68

¹H NMR (CDCl₃, 500 MHz) 6.47 (s, 1H), 6.04 (s, 1H), 6.00 (s, 1H), 5.99 (m, 1H), 5.24 (s, 1H), 4.28 (s, 1H), 3.90–3.70 (m, 2H), 3.80 (s, 3H), 3.74 (s, 3H), 3.65 (d, J = 6.5 Hz, 1H), 3.13 (dd, J = 16.2 Hz, 9.0 Hz, 1H), 2.78 (d, J = 16.2 Hz, 1H), 2.42 (s, 3H), 2.22 (s, 3H), 2.13 (s, 3H); MS (FAB+) m/z 497.1.

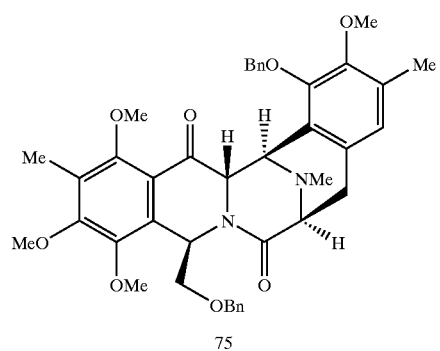

75

¹H NMR (CDCl₃, 500 MHz) 7.54 (d, J = 7.3 Hz, 2H), 7.35–7.25 (m, 3H), 7.10 (m, 3H), 6.81 (d, J = 7.2 Hz, 2H), 6.65 (s, 1H), 6.26 (dd, J = 7.8 Hz, 3.5 Hz, 1H), 5.13 (s, 1H), 5.12 (d, J = 10.8 Hz, 1H), 5.04 (d, J = 10.8 Hz, 1H), 4.46 (s, 1H), 4.14 (d, J = 11.8 Hz, 1H), 3.99 (d, J = 11.8 Hz, 1H), 3.84 (s, 3H), 3.82 (s, 3H), 3.80 (s, 3H), 3.70 (dd, J = 10.9 Hz, 3.6 Hz, 1H), 3.61 (s, 3H), 3.59 (m, 1H), 3.11 (dd, J = 17.3 Hz, 6.8 Hz, 1H), 2.76 (d, J = 17.3 Hz, 1H), 2.22 (s, 3H), 2.172 (s, 3H), 2.169 (s, 3H); HRMS (FAB+) m/z calcd for $C_{41}H_{45}O_8N_2$ 693.3176, found 693.3168.

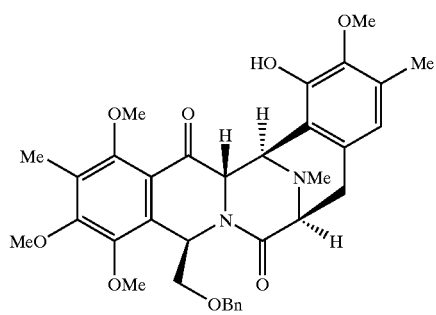

76

$^1$H NMR (CDCl$_3$, 500 MHz) 7.16 (m, 3H), 6.84 (m, 2H), 6.45 (s, 1H), 6.30 (dd, J = 7.5 Hz, 3.8 Hz, 1H), 5.72 (s, 1H), 5.21 (s, 1H), 4.48 (s, 1H), 4.18 (d, J = 11.8 Hz, 1H), 4.07 (d, J = 11.8 Hz, 1H), 3.90–3.70 (m, 2H), 3.85 (s, 3H), 3.83 (s, 3H), 3.80 (s, 3H), 3.73 (s, 3H), 3.70–3,65 (m, 1H), 3.15 (dd, J = 17.3 Hz, 6.8 Hz, 1H), 2.79 (d, J = 17.3 Hz, 1H), 2.38 (s, 3H), 2.19 (s, 3H), 2.17 (s, 3H); MS (ESI+) m/z 603.3.

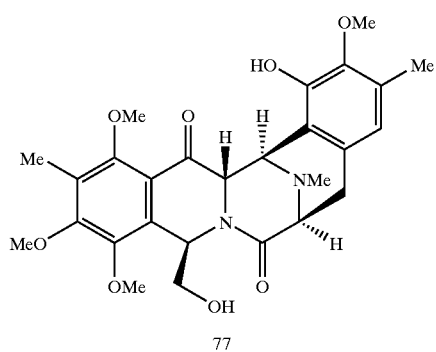

77

$^1$H NMR (CDCl$_3$, 500 MHz) 6.51 (s, 1H), 6.15 (dd, J = 8.5 Hz, 4.4 Hz, 1H), 5.77 (s, 1H), 5.20 (s, 1H), 4.23 (s, 1H), 3.90 (s, 3H), 3.90–3.70 (m, 2H), 3.89 (s, 3H), 3.81 (s, 3H), 3.76 (s, 3H), 3.65 (m, 1H), 3.15 (dd, J = 17.3 Hz, 6.7 Hz, 1H), 2.77 (d, J = 17.3 Hz, 1H), 2.40 (s, 3H), 2.24 (s, 3H), 2.18 (s, 3H); MS (ESI+) m/z 513.5.

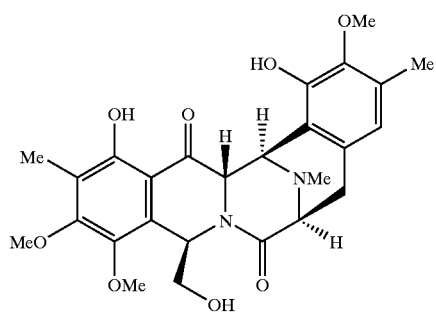

78

$^1$H NMR (CDCl$_3$, 500 MHz) 12.26 (s, 1H), 6.50 (s, 1H), 6.15 (dd, J = 7.2 Hz, 4.3 Hz, 1H), 5.86 (s, 1H), 5.21 (s, 1H), 4.41 (s, 1H), 3.88 (s, 3H), 3.82 (s, 3H), 3.80 (m, 1H), 3.76 (s, 3H), 3.67 (m, 2H), 3.15 (dd, J = 17.4 Hz, 6.7 Hz, 1H), 2.78 (d, J = 17.4 Hz, 1H), 2.38 (s, 3H), 2.24 (s, 3H), 2.11 (s, 3H); MS (ESI+) m/z 500.1.

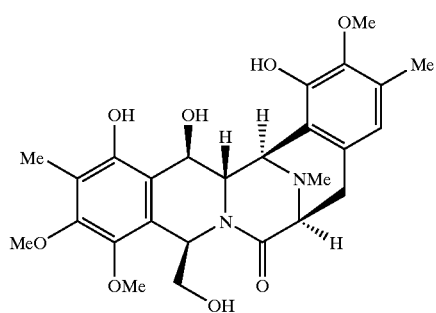

80

$^1$H NMR (CDCl$_3$, 500 MHz) 6.50 (s, 1H), 5.76 (dd, J = 8.2 Hz, 4.1 Hz, 1H), 5.24 (m, 1H), 4.50 (s, 1H), 3.90–3.60 (m, 13H), 3.46 (m, 1H), 3.12 (dd, J = 17.4 Hz, 6.1 Hz, 1H), 2.68 (d, J = 17.4 Hz, 1H), 2.42 (s, 3H), 2.18 (s, 3H), 2.12 (s, 3H); MS (ESI+) m/z 501.4.

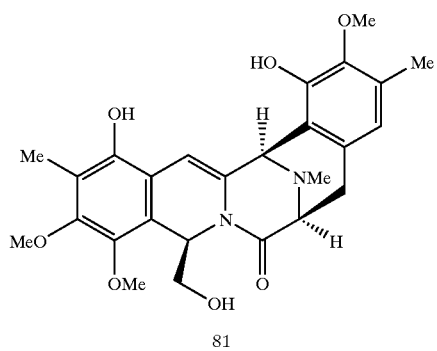
81
¹H NMR (CDCl₃, 500 MHz) 6.52 (s, 1H), 6.26 (s, 1H), 6.04 (s, 1H), 5.81 (br s, 1H), 4.62 (s, 1H), 3.83 (s, 3H), 3.82 (m, 1H), 3.79 (s, 3H), 3.70 (s, 3H), 3.55 (m, 2H), 3.29 (m, 2H), 3.15 (br s, 1H), 3.14 (d, J = 17.4 Hz, 1H), 2.54 (s, 3H), 2.22 (s. 3H), 2.02 (s, 3H); MS (ESI+) m/z 483.5.
¹H NMR (CD₃OD, 500 MHz) 6.50 (s, 1H), 6.48 (s, 1H), 5.95 (t, J = 6.7 Hz, 1H), 4.67 (s, 1H), 3.81 (s, 3H), 3.75 (s, 3H), 3.67 (s, 3H), 3.62 (d, J = 6.2 Hz, 1H), 3.34 (S, 1H), 3.08 (dd, J = 10.8 Hz, 6.3 Hz, 1H), 2.95 (m, 2H), 2.51 (s, 3H), 2.21 (s, 3H), 2.11 (s, 3H).
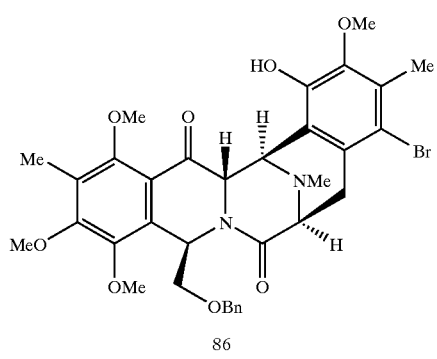
86
¹H NMR (CDCl₃, 500 MHz) 7.40–7.15 (m, 5H), 6.84 (s, 1H), 6.29 (m, 1H), 5.72 (s, 1H), 5.22 (s, 1H), 4.51 (s, 1H), 4.22 (d, J = 11.5 Hz, 1H), 4.09 (d, J = 11.5 Hz, 1H), 3.90–3.60 (m, 15H), 2.95 (m, 2H), 2.38 (s, 3H), 2.36 (s. 3H), 2.14 (s, 3H); MS (ESI+) m/z 682.9.
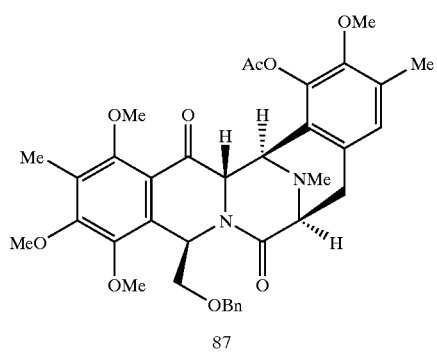
87
¹H NMR (CDCl₃, 500 MHz) 7.20–6.80 (m, 5H), 6.79 (s, 1H), 6.28 (m, 1H), 5.28 (s, 1H), 4.34 (s, 1H), 4.20 (m, 1H), 4.08 (m, 1H), 4.85–3.60 (m, 15H), 3.47 (m, 1H), 3.15 (m, 1H), 2.84 (d, J = 17.3 Hz, 1H), 2.35 (s, 3H), 2.33 (s, 3H), 2.28 (s, 3H).
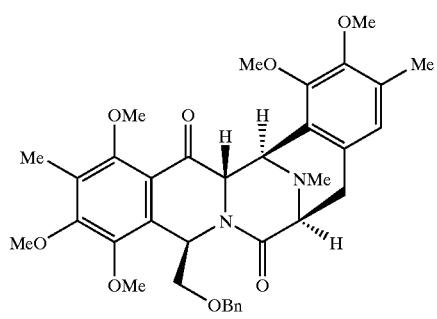
93
¹H NMR (CDCl₃, 400 MHz) 7.20–6.80 (m, 5H), 6.63 (s, 1H), 6.28 (t, J = 3.6 Hz, 1H), 5.17 (s, 1H), 4.46 (s, 1H), 4.20–3.60 (m, 18H), 3.15 (m, 1H), 2.80 (d, J = 17.3 Hz, 1H), 2.38 (s, 3H), 2.21 (s, 3H), 2.18 (s, 3H); MS (ESI+) m/z 616.8.

Discussion

Referring to Scheme α, below, there is a strikingly different outcome in the seemingly similar ring closure steps of IV to V and 39 to 40 (or III). We focus on the hypothetical iminium ions VII and IX which presumably appear in the two progressions. In each case, the system has been programmed such that attack of the nucleophile can only occur from one face of the iminium electrophile (β-as drawn). The interesting issue arises with respect to the stereochemistry of the reaction of the nucleophile. If the enol is attacked from its α-face, the "anti" backbone will be produced (cf. IV to V). Alternatively, attack from the β-face of the enol would give rise to a syn backbone product (39 to 40).

direction of orthogonalization. From this perspective the syn backbone cyclization product would be expected (see stereostructure IX, which leads to 40 (or III).

Comparable modeling reveals that in the case of hypothetical stereostructure VIII, which could also arise from IV, attack at the β-face of the enol, though favored from the perspective of maximal maintenance of amide coplanarity, would incur a serious steric interaction between ring B and the two carbon bridge. This hindrance would be compounded by a particularly close abutment between the β-disposed vinyl and carbomethoxy groups if cyclization leading to the hypothetical X were to ensue. Hence, V rather than X is produced. By contrast, in IX, where the

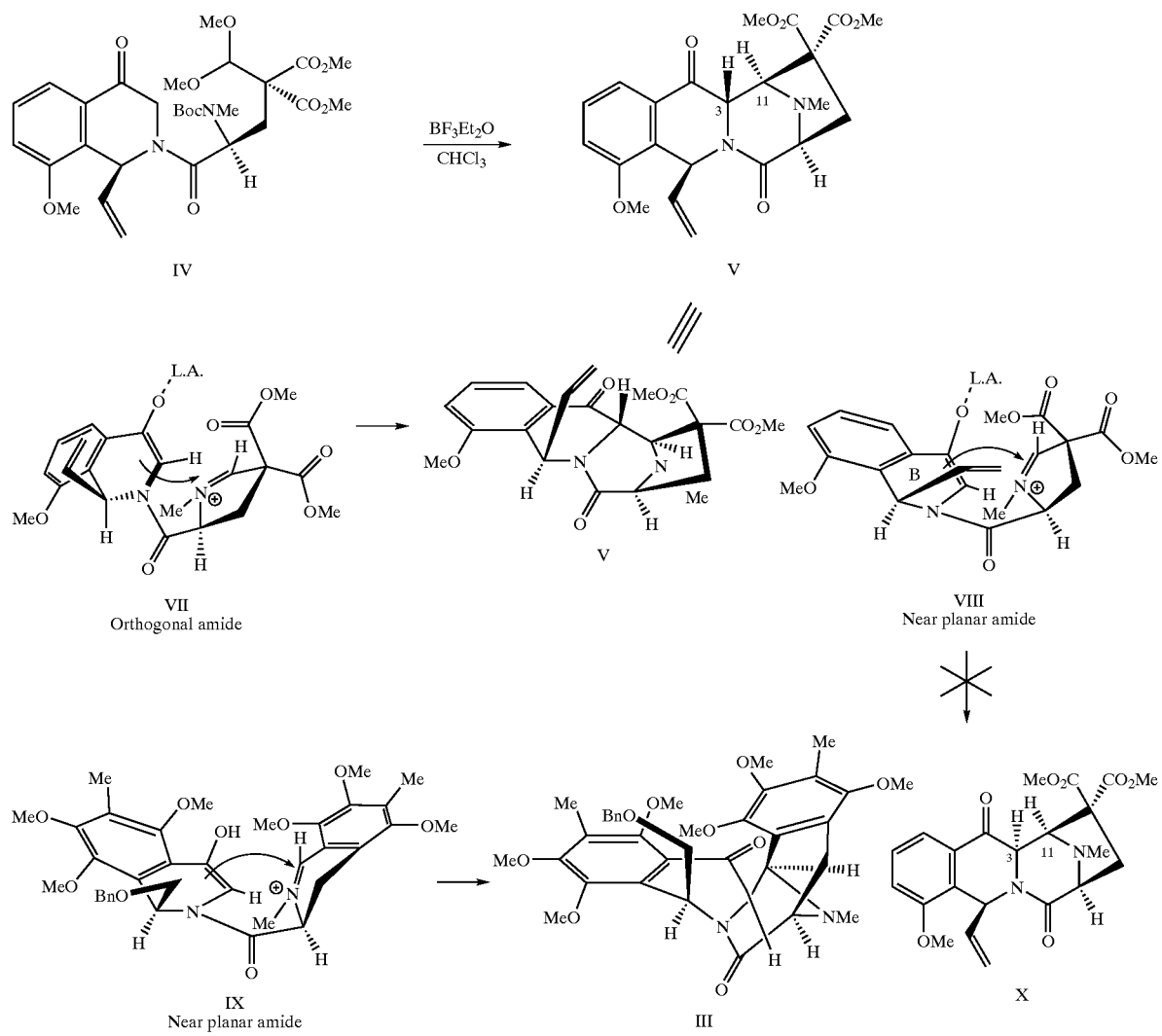

SCHEME α

Aside from issues of steric hindrance, there is a potentially important stereoelectronic consideration. In modeling the closure reaction, it is seen that the coplanarity of the amide substituents can be maintained only if the enol is attacked from its β-face. By contrast, attack at the α-face of the enol seems to require rotation about the amide in the 6-membered iminium ring contains two additional $sp^2$ centers, the steric problems arising from the emerging syn backbone bridged system are perhaps reduced. In summary, it is proposed that cyclization of 39 (by way of stereostructure IX) is governed by the stereoelectronic factor (maintenance of amide coplanarity), while cyclization of IV (by way of stereostructure VII), is dictated by an overriding steric hindrance effect, leads to V.

Subsequent studies revealed that the stereochemical outcome of the Mannich closure step is also a function of the substitution pattern on the aldehyde-containing aromatic ring that enters into the cyclization event.

This shows that the Mannich-like closure of 39 to 40 (III) directly provides the backbone stereochemistry required for the subject alkaloids, in contrast to the stereochemical outcome in a related, earlier case (IV to V).

Based on prior art, compounds which contain a two tetrahydroisoquinoline aromatic carbon nitrogen framework, such as saframycin B, saframycin A (13,14), saframycin S (15), ecteinascidin 729 (Et 729) (16), Et 743 and Phthalascidin (3) have consistently exhibited pharmacological, antibiotic, cytotoxic, antitumor, anti-tumorigenic and cellular anti-proliferative activity both in vivo and in vitro. Several publications reveal that compounds which possess a two tetrahydroisoquinoline aromatic carbon nitrogen framework can function as cytotoxic antitumor agents. (13, 14, 15, 16, 3) Saframycins are also known for their antibiotic capabilities. (19) These cytotoxic antitumor agents have been shown to interact with DNA. (18, 14) In similar core structured saframycins and ecteinacidins as the compounds of this invention, interactions occur between DNA and the core tetrahydroisoquinoline aromatic carbon nitrogen framework. (2, 18, 20) Compounds disclosed in this invention, based on chemical and structural similarities to pthalicidins, ecteinicidins and saframycins, are therefore capable of interacting with DNA as well as possessing antitumor, antibiotic, cytotoxic and cellular anti-proliferative activity both in vivo and in vitro.

The pharmacological, antitumor, anti-tumorigenic, cytotoxic and cellular anti-proliferative activity of the compounds disclosed here both in vivo and in vitro can be determined by using published test procedures.

In vivo assays to determine a compound's antitumor capabilities are typically performed in rodents or other species. Tumor growth is determined by the growth of tumors from transplanted transformed cells or tumor xenographs into or onto the animal. (See,. eg., 13, 16, 21) In vitro assays to determine a compound's antitumor capabilities can be performed using a soft agar cloning assay to determine the in vitro effects of the disclosed compounds against primary tumor specimens taken directly from patients. (See, eg., 22) Anti-proliferative efficacy and cytotoxicity typically can be determined by absorbance of viable cells and the use of a reference wavelength to serve as an index for the viable cells. (See, eg., 3)

Example 10

Alternative construction of chiral subunits 3 and 4 for use in preparation of the Saframycin-Ecteinascidin Series.

The following schemes 12 and 13 result in subunits, 3 and 4, which were used to prepare analogues within the Saframycin-Ecteinascidin Series.

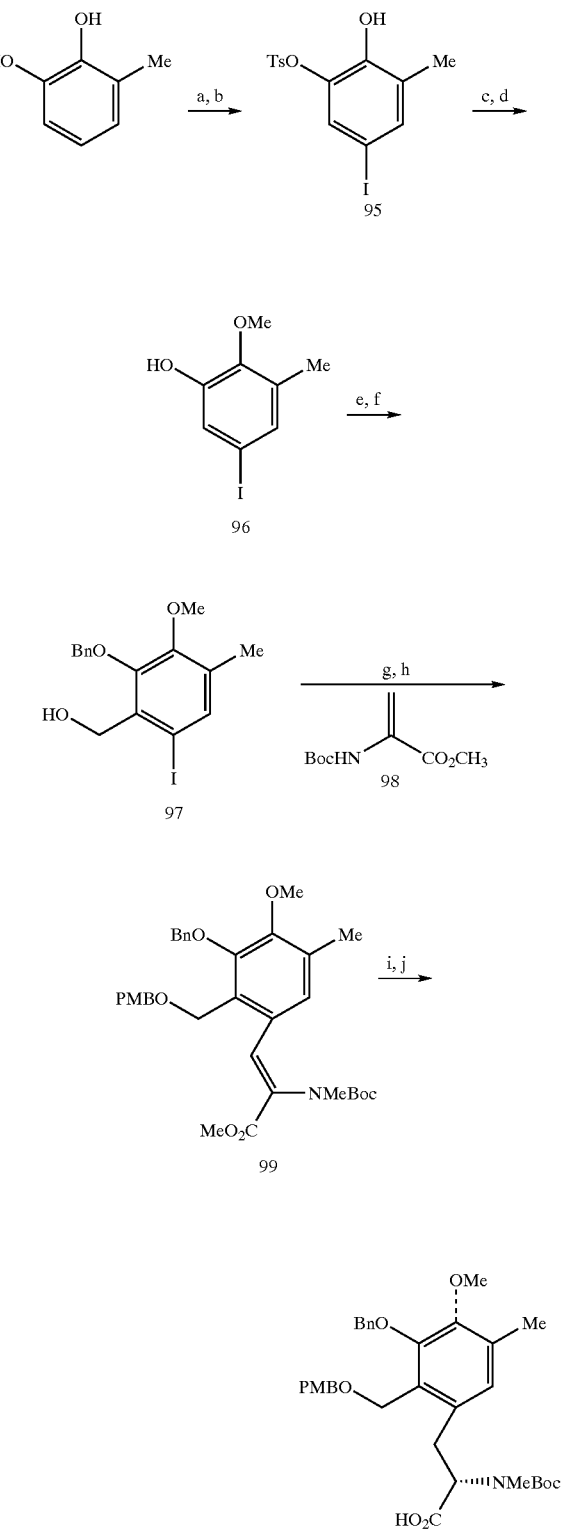

Scheme 12.

a) TsCl, Et$_3$N, CH$_2$Cl$_2$, 0° C., 2 h, 93%; b) ICl, AcOH, 70° C., 20 h, 92%; c) CH$_3$I, K$_2$CO$_3$, acetone, reflux, 12 h, 100%; d) NaOH, EtOH, H$_2$O, reflux, 4 h, 94%; e) (CH$_2$O)$_n$, Me$_2$AlCl, CH$_2$Cl$_2$, 0° C. -> rt, 12 h, 77%; f) BnBr, K$_2$CO$_3$, acetone, reflux, 12 h, 95%; g) PMBCl, NaH, n-Bu$_4$N$^+$I$^-$, THF-DMF, rt, 12 h, 99%; h) 28, (o-tolyl)$_3$P, Et$_3$N, Bu$_4$N$^+$Cl$^-$, Pd(OAc)$_2$, DMF, 130° C., 12 h, 78%; i) (S,S)-Et-DuPhos, H$_2$ (100 psi), MeOH, rt, 2 d, 90%; j) NaH, MeI, THF, 0° C. -> rt, 12 h, 60%.

Scheme 13.

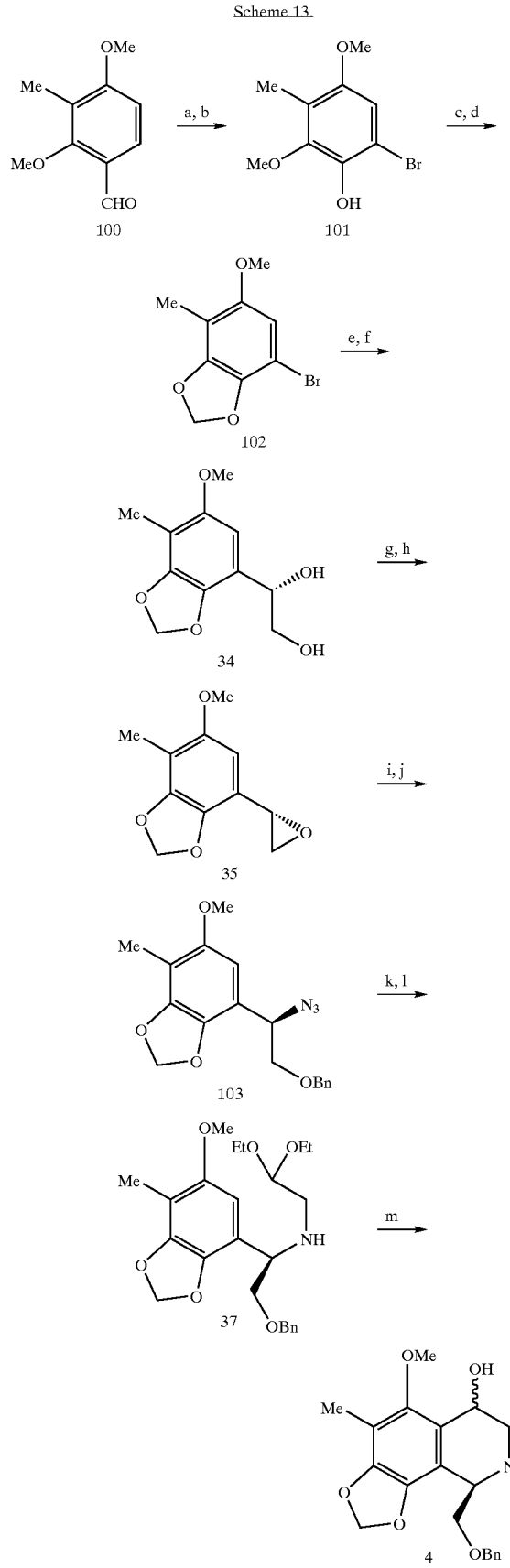

-continued (a) m-CPBA, p-TsOH, $CH_2Cl_2$; then $Et_3N$, $CH_2Cl_2$-MeOH, 100%; (b) $Br_2$, $K_2CO_3$, $CH_2Cl_2$, -78° C., 80%; (c) $AlCl_3$, $CH_2Cl_2$, rt, overnight, 99%; (d) $BrCH_2Cl$, $Cs_2CO_3$, MeCN, reflux, 82%; (e) Vinyltributyltin, $Pd(PPh_3)_4$, toluene, reflux, 90%; (f) AD-mix-α, t-BuOH-$H_2O$(1:1), 0° C., 95%; (g) TsCl, pyridine-$CH_2Cl_2$; (h) $K_2CO_3$, MeOH, 72% for 2 steps; (i) $NaN_3$, $LiClO_4$, MeCN, 60° C.; (j) BnBr, NaH, THF, 70% for 2 steps; (k) $H_2$, Pd/C, EtOAc, 90%; (l) $K_2CO_3$, $BrCH_2CH(OEt)_2$, MeCN, reflux, 72%; (m) 6N HCl, Dioxane, $H_2O$, then NaOH, 86% (β-OH:α-OH = 2:3).

Example 11

Synthesis of analogues within the Saframycin-Ecteinascidin Series using sub units 1 and 2—Scheme 14

Scheme 14.

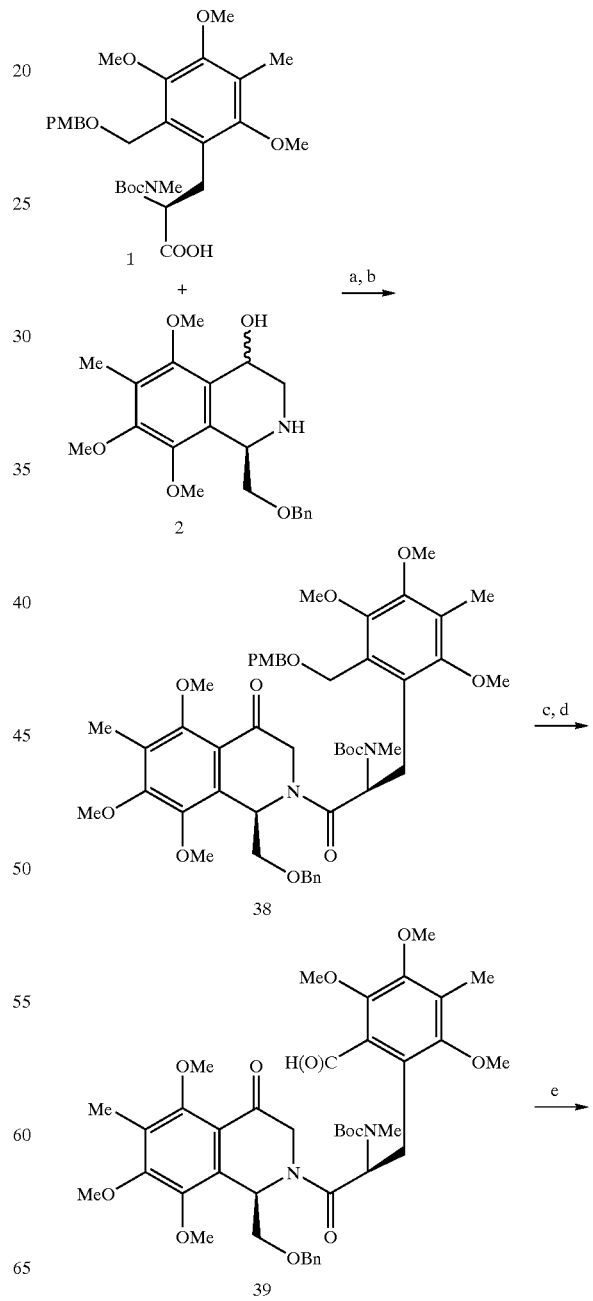

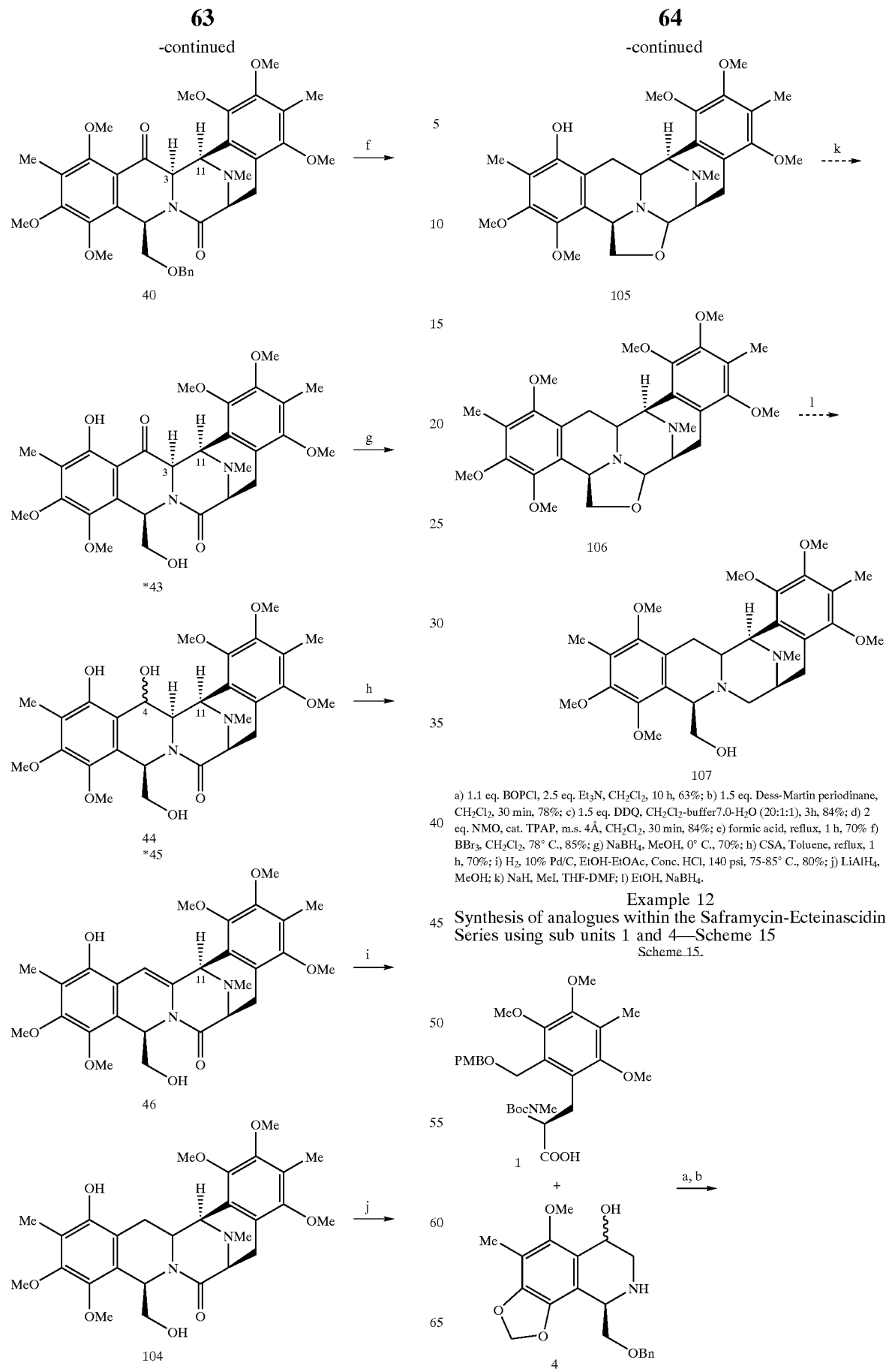

Example 12
Synthesis of analogues within the Saframycin-Ecteinascidin Series using sub units 1 and 4—Scheme 15

Scheme 15.

a) 1.1 eq. BOPCl, 2.5 eq. Et₃N, CH₂Cl₂, 10 h, 63%; b) 1.5 eq. Dess-Martin periodinane, CH₂Cl₂, 30 min, 78%; c) 1.5 eq. DDQ, CH₂Cl₂-buffer7.0-H₂O (20:1:1), 3h, 84%; d) 2 eq. NMO, cat. TPAP, m.s. 4Å, CH₂Cl₂, 30 min, 84%; e) formic acid, reflux, 1 h, 70% f) BBr₃, CH₂Cl₂, 78° C., 85%; g) NaBH₄, MeOH, 0° C., 70%; h) CSA, Toluene, reflux, 1 h, 70%; i) H₂, 10% Pd/C, EtOH-EtOAc, Conc. HCl, 140 psi, 75-85° C., 80%; j) LiAlH₄, MeOH; k) NaH, MeI, THF-DMF; l) EtOH, NaBH₄.

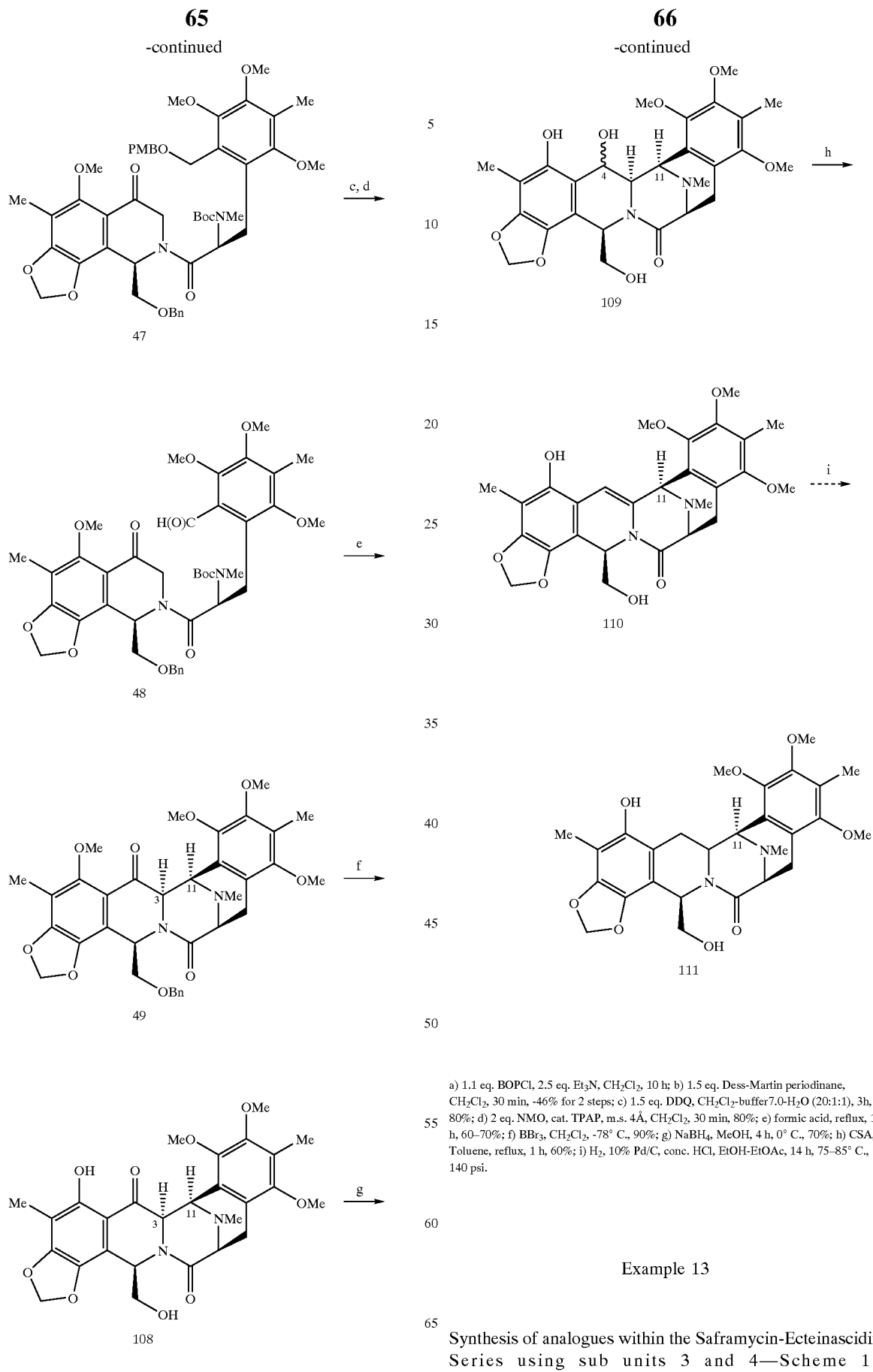
Example 13
Synthesis of analogues within the Saframycin-Ecteinascidin Series using sub units 3 and 4—Scheme 16

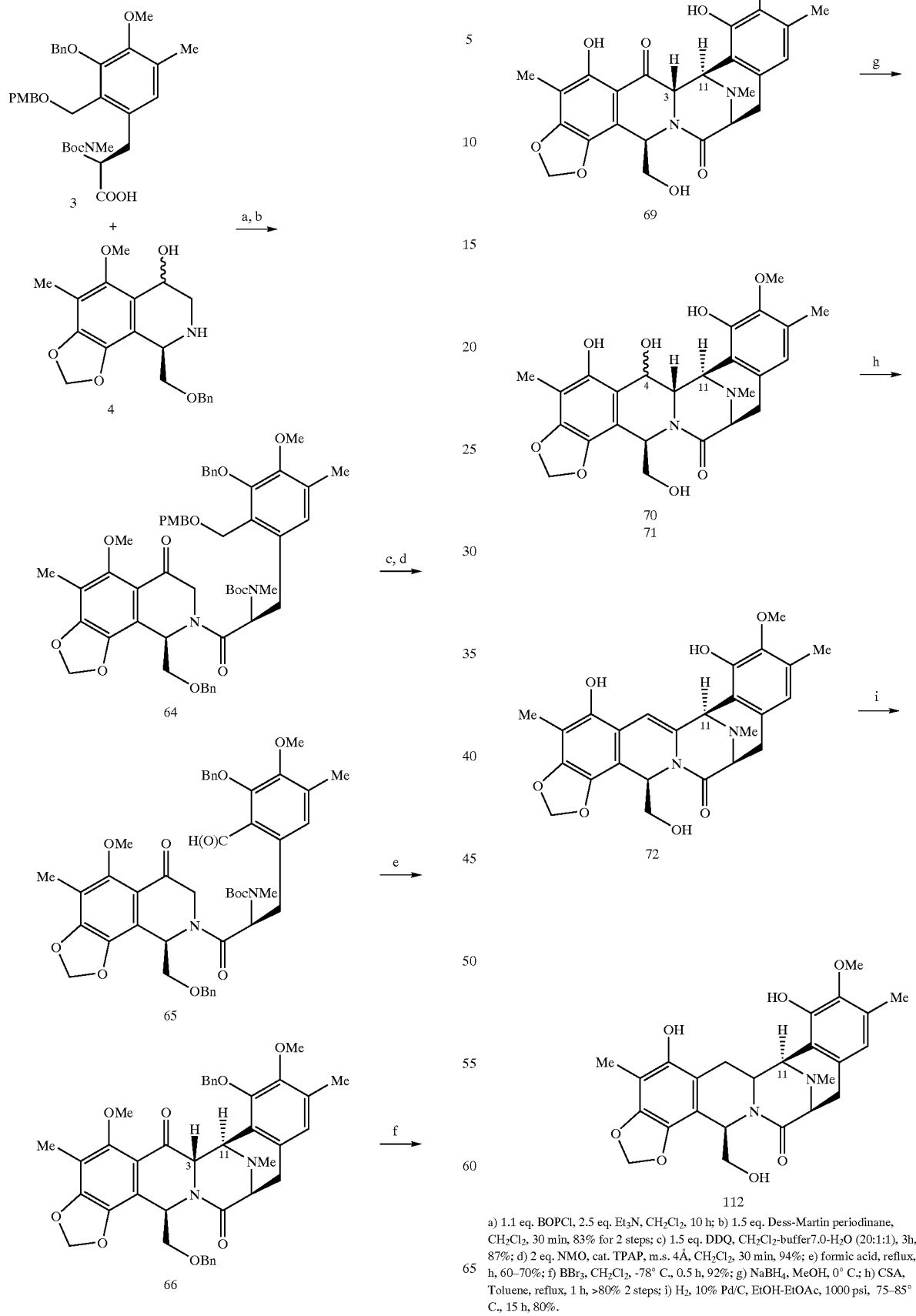
Scheme 16.
a) 1.1 eq. BOPCl, 2.5 eq. Et₃N, CH₂Cl₂, 10 h; b) 1.5 eq. Dess-Martin periodinane, CH₂Cl₂, 30 min, 83% for 2 steps; c) 1.5 eq. DDQ, CH₂Cl₂-buffer7.0-H₂O (20:1:1), 3h, 87%; d) 2 eq. NMO, cat. TPAP, m.s. 4Å, CH₂Cl₂, 30 min, 94%; e) formic acid, reflux, 1 h, 60–70%; f) BBr₃, CH₂Cl₂, -78° C., 0.5 h, 92%; g) NaBH₄, MeOH, 0° C.; h) CSA, Toluene, reflux, 1 h, >80% 2 steps; i) H₂, 10% Pd/C, EtOH-EtOAc, 1000 psi, 75–85° C., 15 h, 80%.

Example 14
Synthesis of Analogues within the Saframycin-Ecteinascidin Series using sub units 3 and 4—Scheme 17
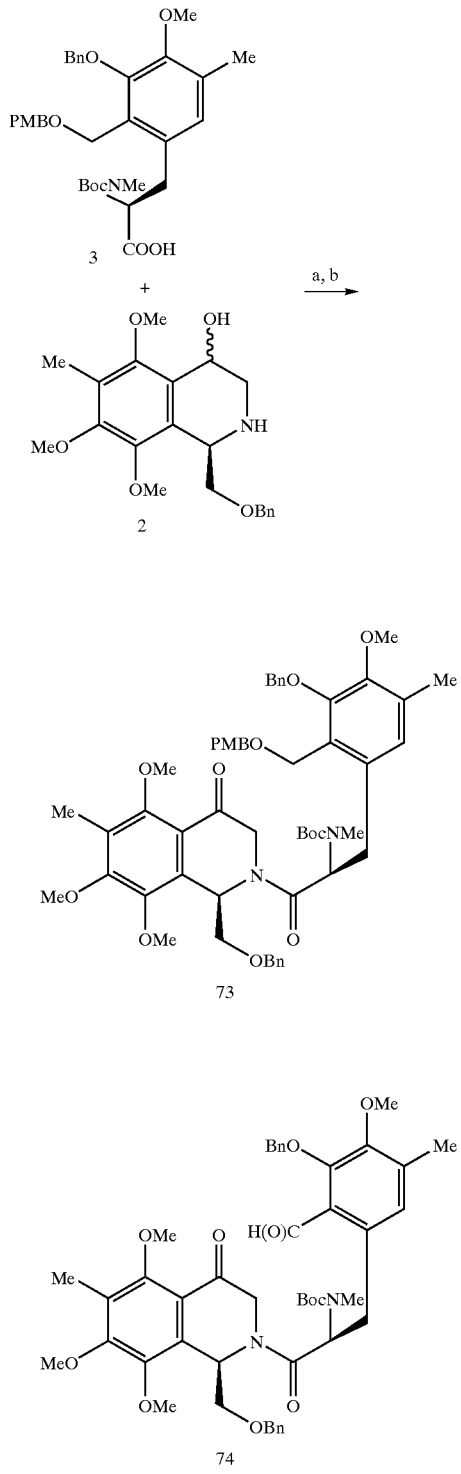
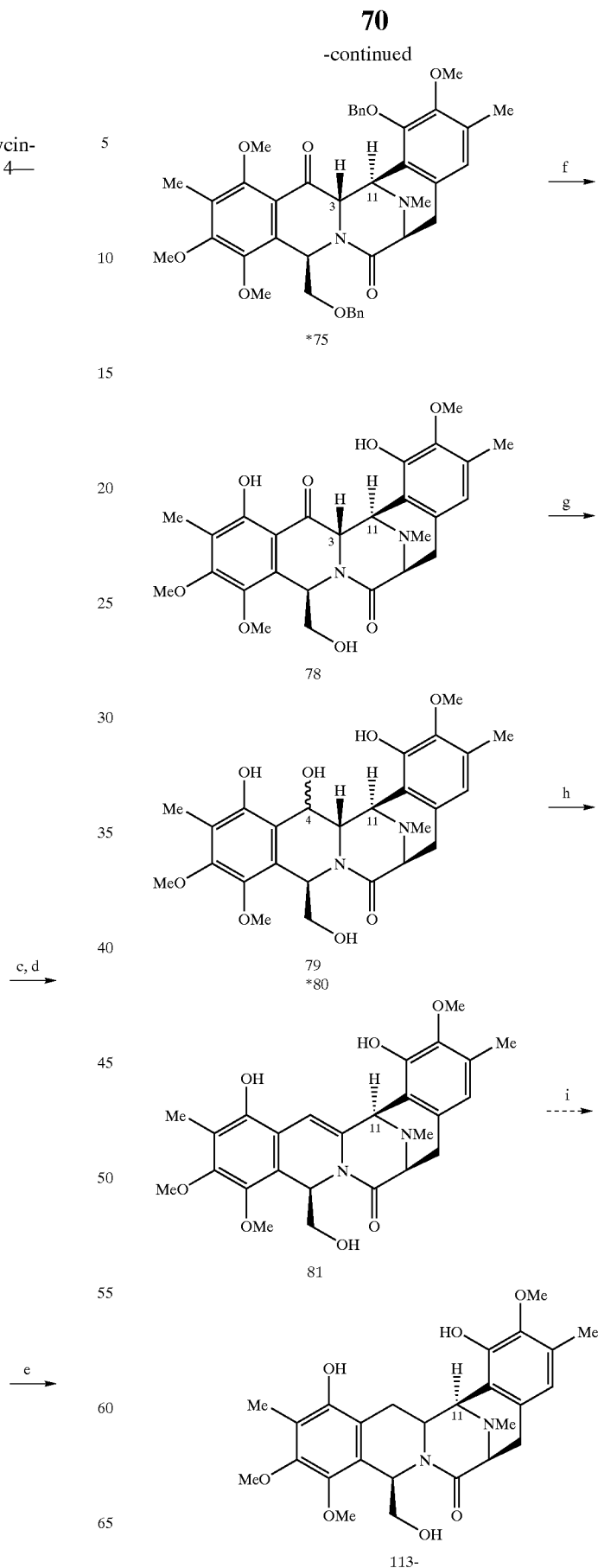

-continued a) 1.1 eq. BOPCl, 2.5 eq. Et$_3$N, CH$_2$Cl$_2$, 10 h; b) 1.5 eq. Dess-Martin periodinane, CH$_2$Cl$_2$, 30 min, -50% for 2 steps; c) 1.5 eq. DDQ, CH$_2$Cl$_2$-buffer7.0-H$_2$O (20:1:1), 3h, 70–80%; d) 2 eq. NMO, cat. TPAP, m.s. 4Å, CH$_2$Cl$_2$, 30 min, 70–80%; e) formic acid, reflux, 1 h, 60–70%; f) BBr$_3$, CH$_2$Cl$_2$, -78° C., 93–99%; g) NaBH$_4$, MeOH, 0° C., 50%; h) CSA, Toluene, reflux, 92%, i) H$_2$, 10% Pd/C, EtOH-EtOAc, 1000 psi, 75–85° C., 15 h.

References

1. R. Sakai, K. L. Rinehart, Y. Guan, A. Wang, *Proc. Natl. Acad. Sci.* 1992, 89, 11456. Rinehart, K. L., et al., *JOC,* 1990, 55, 2355.
2. E. J. Corey, D. Y. Gin, R. S. Kania, *J. Am. Chem. Soc.* 1996, 118, 9202.
3. E. J. Martinez, T. Owa, S. L. Schreiber, E. J. Corey, *Proc. Natl. Acad. Sci.* 1999, 96, 3496.
4. S. J. Danishefsky, P. J. Harrison, R. R. Webb, B. T. O'neill, *J. Am. Chem. Soc.* 1985, 107, 1421.
5. For the previous work on the total syntheses of saframycins see: (a) T. Fukuyama, R. A. Sachleben, *J. Am. Chem. Soc.* 1982, 104, 4957. (b) T. Fukuyama, L. Yang. K. Ajeck, R. A. Sachleben, *J. Am. Chem. Soc.* 1990, 112, 3712. (c) A. Kubo, N. Saito, H. Nishioka, H. Yamato, K. Masubuchi, M. Nakamaura, *J. Org. Chem.* 1988, 53, 4295. A brilliant and ultimately concise total sytnhesis of the saframycins was disclosed by Professor Andrew Myers, Harvard University at the 1998 Tetrahedron Prize Symposium (216th National Meeting of the American Chemical Society, Boston, Mass., 1998). A. G. Myers, D. W. Kung, *J. Am. Chem. Soc.* 1999, 121, 10828.
6. a) K. B. Sharpless, Y. Gao, R. M. Hanson, J. M. Klunder, S. Y. Ko, H. Masamune, *J. Am. Chem. Soc.* 1987, 109, 5765. (b) K. B. Sharpless, J. Hartung, K. Jeong, H. Kwong, K. Morikawa, Z. Wang, D. Xu, X. Zhang, *J. Org. Chem.* 1992, 57, 2768. (c) M. Caron, P. R. Carlier, K. B. Sharpless, *J. Org. Chem.* 1998, 53, 5185.
7. T. Fukuyama, S. D. Linton, M. M. Tun, *Tetrahedron Lett.* 1990, 31, 5989.
8. H. D. Dakin, *Am. Chem. J.* 1909, 42, 477.
9. E. Medina, A. Vial-Ferran, A. Moyano, M. A. Pericas, A. Piera, *Tetrahedron Asym.* 1997, 8, 1581.
10. A. Kubo, Y. Kitahara, S. Nakahara, R. Numata, *Chem. Phar. Bull.* (Japan) 1985, 33, 2122.
11. J. M. Bobbitt, J. M. Kiely, K. L. Khanna, R. Ebermam, *J. Org. Chem.* 1965, 30, 2247.
12. J. Cabre-Castellvi, A. Polomo-Coll, A. C. Palomo-Coll, *Synthesis,* 1981, 616.
13. Okumoto T, Kawana M, Nakamura I, Ikeda Y, Isagai K: Activity of safracins A and B, heterocyclic quinone antibiotics, on experimental tumors in mice, *J Antibiot* (Tokyo), vol. 38, No. 6, June 1985, pages 767–771
14. Kishi K, Yazawa K, Takahashi K, Mikami Y, Arai T: Structure-activity relationships of saframycins, *J Antibiot.* (Tokyo), Vol. 37, No. 8, August 1984 pages 847–852
15. Mikami Y, Yokoyama K, Tabeta H, Nakagaki K, Arai T: Saframycin S, a new saframycin group antibiotic, *J Pharmacobiodyn.* Vol. 4, No. 4, April 1981, pages 282–286
16. Reid J M, Walker D L, Ames M M.: Preclinical pharmacology of ecteinascidin 729, a marine natural product with potent antitumor activity Vol. 38, No. 4 (1996) pp 329–334
17. Sakai R, Jares-Erijman E A, Manzanares I, Silva Elipe M V, Rinehart K L: Ecteinascidins: Putative Biosynthetic Precursors and Absolute Stereochemistry, J. Am. Chem. Soc. Vol. 118, 1996, pages 9017–9023
18. Rao and Lown.: Mode of action of saframycin antitumor antibiotics: sequence selectivities in the covalent binding of saframycins A and S to deoxyribonucleic acid, *Chem Res Toxicol.* Vol. 3, No. 3, May–June 1990, pages 262–267
19. Arai T, Takahashi K, Kubo A, New antibiotics saframycins A, B, C, D and E, *J Antibiot.* (Tokyo), Vol. 30, No. 11, November 1977, pages 1015–1018
20. Guan Y, Sakai R, Rinehart K L, Wang A H, Molecular and crystal structures of ecteinascidins: potent antitumor compounds from the Caribbean tunicate *Ecteinascidia turbinata, J. Biomol Struct. Dyn.* Vol. 10, No. 5, April 1993, pages 793–818
21. Valoti G, Nicoletti M I, Pellegrino A, Jimeno J, Hendriks H, D'Incalci M, Faircloth G, Giavazzi R, Ecteinascidin-743, a new marine natural product with potent antitumor activity on human ovarian carcinoma xenografts, *Clin. Cancer Res.* Vol. 4, No. 8, August 1998, pages 1977–1983
22. Izbicka E, Lawrence R, Raymond E, Eckhardt G, Faircloth G, Jimeno J, Clark G, Von Hoff D D, In vitro antitumor activity of the novel marine agent, ecteinascidin-743 (ET-743, NSC-648766) against human tumors explanted from patients, *Ann. Oncol.* Vol. 9, No. 9, September 1998, pages 981–987

What is claimed is:

1. A compound having the formula:

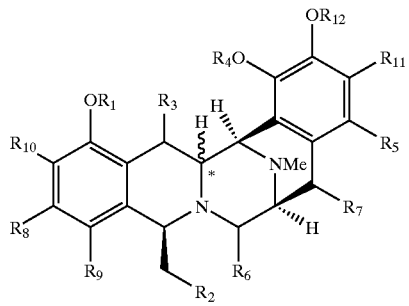

wherein $R_1$ and $R_4$ is H, a $C_1$ to $C_4$ alkyl group, C(O) ($C_1$–$C_4$ alkyl) or additionally $R_4$ is benzyl;

wherein $R_2$ is H, OH, O($C_1$–$C_4$ alkyl), O-benzyl, OC(O) H, OC(O)($C_1$–$C_4$ alkyl), OC(O)benzyl, OSi(CH$_1$)$_2$(t-butyl), or a phthalimide group;

wherein $R_3$ is =O, OH, O($C_1$–$C_4$ alkyl), OC(O)($C_1$–$C_2$ alkyl), or OC(O)benzyl;

wherein $R_5$ is H, halogen, OH, or —OC$_{(1-6)}$ alkyl group;

wherein $R_6$ is =O, OH, OC$_3$, CN, OC(O)H, OC(O) ($C_1$–$C_4$ alkyl), or OC(O)benzyl;

wherein $R_7$, is H, =O, OH, or halogen;

wherein $R_8$ and $R_9$ are independently H, CH$_3$, OCH$_3$, OC$_2$H$_5$, Br, P, or CF$_3$;

wherein $R_{10}$ and $R_{11}$ are independently CH$_3$, OCH$_3$, OC$_2$H$_5$, SCH$_3$, or SC$_2$H$_5$;

wherein $R_{12}$ is H, a $C_1$ to $C_4$ alkyl group, or C(O)($C_1$–$C_4$ alkyl); and wherein the chiral center marked * has the R or the S configuration.

2. The compound of claim 1, having the formula:

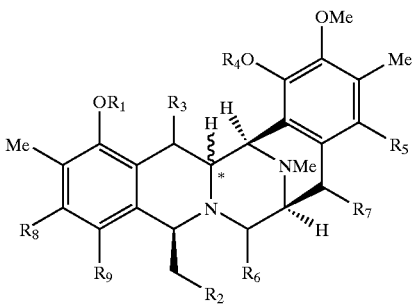

wherein $R_1$ and $R_4$ is H, a $C_1$ to $C_4$ alkyl group, C(O) ($C_1$–$C_4$ alkyl) or additionally $R_4$ is benzyl;

wherein $R_2$ is H, OH, O($C_1$–$C_4$ alkyl), O-benzyl, OC(O)H, OC(O)($C_1$–$C_4$ alkyl), OC(O)benzyl, OSi(CH$_3$)$_2$(t-butyl), or a phthalimide group;

wherein $R_3$ is =O, OH, O($C_1$–$C_4$ alkyl), OC(O)($C_1$–$C_2$ alkyl), or OC(O)benzyl;

wherein $R_5$ is H, halogen, OH, or —OC$_{(1-6)}$ alkyl group;

wherein $R_6$ is =O, OH, OCH$_3$, CN, OC(O)H, OC(O) ($C_1$–$C_4$ alkyl, or OC(O)benzyl;

wherein $R_7$, is H, =O, OH, or halogen;

wherein $R_8$ and $R_9$ are independently H, CH$_3$, OCH$_3$, OC$_2$H$_5$, Br, F, or CF$_3$; and wherein the chiral center marked * has the R or the S configuration.

3. The compound of claim 2, having the formula:

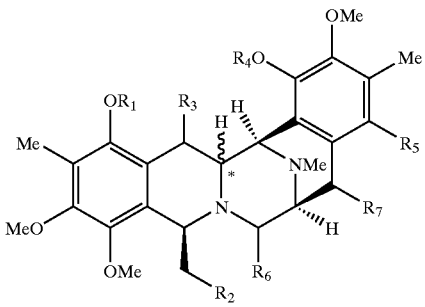

wherein $R_1$ and $R_4$ is H, a $C_1$ to $C_4$ alkyl group, C(O) ($C_1$–$C_4$ alkyl) or additionally $R_4$ is benzyl;

wherein $R_2$ is H, OH, O($C_1$–$C_4$ alkyl), O-benzyl, OC(O)H, Osi(CH$_3$)$_2$(t-butyl), or a phthalimide group;

wherein $R_3$ is =O, OH, O($C_1$–$C_4$ alkyl), OC(O)($C_1$–$C_2$ alkyl), or OC(O)benzyl;

wherein $R_5$ is H, halogen, OH, or —OC$_{(1-6)}$ alkyl group;

wherein $R_6$ is =O, OH, OCH$_3$, CN, OC(O)H, OC(O) $C_1$–$C_4$ alkyl), or OC(O)benzyl;

wherein $R_7$, is H, =O, OH, or halogen and wherein the chiral center marked * has the R or the S configuration.

4. The compound of claim 3, wherein $R_1$ is CH$_3$, $R_3$ is =O, $R_4$ is =O, $R_4$ is CH$_3$, $R_5$ is OCH$_3$, $R_6$ is =O, and $R_7$ is H.

5. The compound of claim 4, wherein $R_2$ is OC(O)H.
6. The compound of claim 4, wherein $R_2$ is H.
7. The compound of claim 4, wherein $R_2$ is OH.
8. The compound of claim 4, wherein $R_2$ is —O-benzyl.
9. The compound of claim 4, wherein $R_2$ is OCOCH$_3$.
10. The compound of claim 4, wherein $R_2$ is —O-t-butyldimethylsilyl.
11. The compound of claim 4, wherein $R_2$ is —O-Pivaloyl.
12. The compound of claim 3, wherein $R_1$ is H, $R_3$ is =O, $R_4$ is CH$_3$, $R_5$ is OCH$_3$, $R_6$ is =O, and $R_7$ is H.
13. The compound of claim 12, wherein $R_2$ is —O-pivaloyl.
14. The compound of claim 3, wherein $R_1$ is H, $R_3$ is =O, $R_4$ is benzyl, $R_5$ is OCH$_3$, $R_6$ is =O, and $R_7$ is H.
15. The compound of claim 3, wherein $R_1$ is H, $R_3$ is =O, $R_4$ is H, $R_5$ is OCH$_3$, $R_6$ is =O, and $R_7$ is H.
16. The compound of claim 3, wherein $R_1$ is H, $R_3$ is =O, $R_4$ is H, $R_5$ is H, $R_6$ is =O, and $R_7$ is H.
17. The compound of claim 3, wherein $R_3$ is =O, $R_4$ is H, $R_5$ is halogen, $R_6$ is =O, and $R_7$ is H.
18. A compound having the formula:

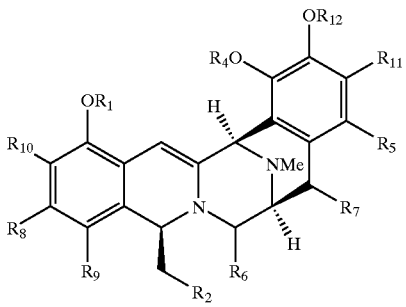

wherein $R_1$ and $R_4$ is H, a $C_1$ to $C_4$ alkyl group, C(O) ($C_1$–$C_4$ alkyl) or additionally $R_4$ is benzyl;

wherein $R_2$ is H, OH, O($C_1$–$C_4$ alkyl), O-benzyl, OC(O)H, OC(O)($C_1$–$C_4$ alkyl), OC(O)benzyl, OSi (CH$_3$)$_2$(t-butyl), or a phthalimide group;

wherein $R_5$ is H, halogen, OH, or O($C_1$–$C_6$ alkyl);

wherein $R_6$ is =O, OH, OCH$_3$, CN, OC(O)H, OC(O) ($C_1$–$C_4$ alkyl), or OC(O)benzyl;

wherein $R_7$, is H, =O, OH, or halogen;

wherein $R_8$ and $R_9$ are independently H, CH$_3$, OCH$_3$, OC$_2$H$_5$, Br, F, or CF$_3$;

wherein $R_{10}$ and $R_{11}$ are independently CH$_3$, OCH$_3$, OC$_2$H$_5$, SCH$_3$, or SC$_2$H$_5$; and wherein $R_{12}$ is H, a $C_1$ to $C_4$ alkyl group, or OC(O)benzyl.

19. The compound of claim 18, having the formula:

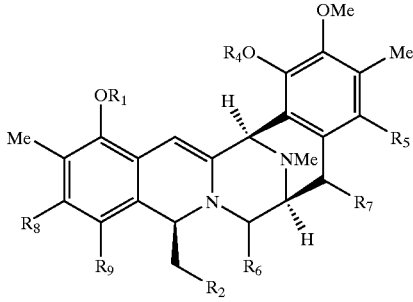

wherein $R_1$ and $R_4$ is H, a $C_1$ to $C_4$ alkyl group, C(O) ($C_1$–$C_4$ alkyl) or additionally $R_4$ is benzyl;

wherein R₂ is H, OH, O(C₁–C₄ alkyl), O-benzyl, OC(O)H, OC(O)(C₁–C₄ alkyl), OC(O)benzyl, OSi(CH₃)₂(t-butyl), or a phthalimide group;

wherein R₅, is H, halogen, OH, or O(C₁–C₆ alkyl);

wherein R₆ is =O, OH, OCH₃, CN, OC(O)H, OC(O)(C₁–C₄ alkyl), or OC(O)benzyl;

wherein R₇, is H, =O, OH, or halogen; and wherein R₈ and R₉ are independently H, CH₃, OCH₃, OC₂H₅, Br, F, or CF₃.

20. The compound of claim 19, having the formula:

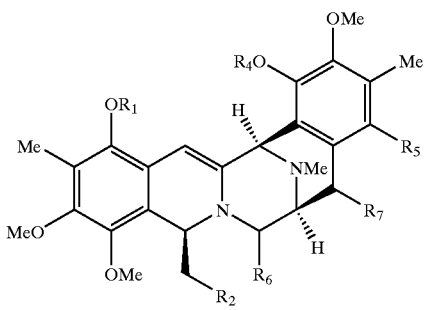

wherein R₁ and R₄ is H, a C₁ to C₄ alkyl group, C(O)(C₁–C₄ alkyl) or additionally R₄ is benzyl;

wherein R₂ is H, OH, O(C₁–C₄ alkyl), O-benzyl, OC(O)H, OC(O)(C₁–C₄ alkyl), OC(O)benzyl, OSi(CH₃)₂(t-butyl), or a phthalimide group;

wherein R₅ is H, halogen, OH, or O(C₁–C₆ alkyl);

wherein R₆ is =O, OH, OCH₃, CN, OC(O)H, OC(O)(C₁–C₄ alkyl), or OC(O)benzyl; and wherein R₇, is H, =O, OH, or halogen.

21. The compound of claim 20, wherein R₁ is CH₃, R₄ is CH₃, R₅ is OCH₃, R₆ is =O, and R₇ is H.

22. The compound of claim 21, wherein R₂ is OC(O)H.

23. The compound of claim 21, wherein R₂ is H.

24. The compound of claim 21, wherein R₂ is OH.

25. The compound of claim 21, wherein R₂ is —O-benzene.

26. The compound of claim 21, wherein R₂ is OCOCH₃.

27. The compound of claim 21, wherein R₂ is —O-t-butyldimethylsilyl.

28. The compound of claim 21, wherein R₂ is —O-Pivaloyl.

29. The compound of claim 20, wherein R₁ is H, R₄ is CH₃, R₅ is OCH₃, R₆ is =O, and R₇ is H.

30. The compound of claim 29, wherein R₂ is —O-pivaloyl.

31. The compound of claim 20, wherein R₁ is H, R₄ is benzyl, R₅ is OCH₃, R₆ is =O, and R₇ is H.

32. The compound of claim 20, wherein R₁ is H, R₄ is H, R₅ is OCH₃, R₆ is =O, and R₇ is H.

33. The compound of claim 20, wherein R₁ is H, R₄ is H, R₅ is H, R₆ is =O, and R₇ is H.

34. The compound of claim 20, wherein R₁ is H, R₄ is H, R₅ is halogen, R₆ is =O, and R₇ is H.

35. A compound having the formula:

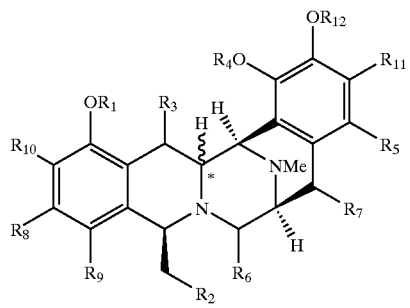

wherein R₁ and R₄ is H, a C₁ to C₄ alkyl group, C(O)(C₁–C₄ alkyl) or additionally R₄ is benzyl;

wherein R₂ is H, OH, O(C₁–C₄ alkyl), O-benzyl, OC(O)H, OC(O)(C₁–C₄ alkyl), OC(O)benzyl, or OSi(CH₃)₂(t-butyl);

wherein R₃ is =O, OH, H, O(C₁–C₄ alkyl), OC(O)(C₁–C₂ alkyl), or OC(O)benzyl;

wherein R₅ is H, halogen, OH, or =OC₍₂₋₆₎ alkyl group;

wherein R₆ is H, =O, OH, OCH₃, CN, OC(O)H, OC(O)(C₁–C₄ alkyl), or OC(O)benzyl;

wherein R₇, is H, =O, OH, OCH₃, or halogen;

wherein R₈ and R₉ are independently H, CR₃, OCH₃, OC₂H₅, Br, F, or CF₃;

wherein R₁₀ and R₁₁ are independently CH₃, OCH₃, OC₂H₅, SCH₃, or SC₂H₅;

wherein R₁₂ is H, a C₁ to C₄ alkyl group, or C(O)(C₁–C₄ alkyl); and wherein the chiral center marked * has the R or the S configuration.

36. The compound of claim 35, having the formula:

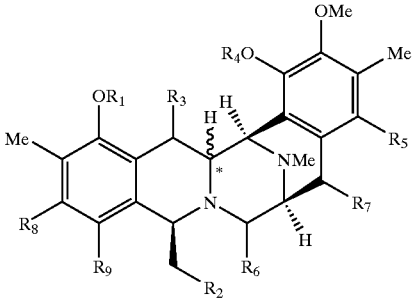

wherein R₁ and is R₄ is H, a C₁ to C₄ alkyl group, C(O)(C₁–C₄ alkyl) or additionlly R₄ is benzyl;

wherein R₂ is H, OH, O(C₁–C₄ alkyl), O-benzyl, OC(O)H, OC(O)(C₁–C₄ alkyl), OC(O)benzyl, or OSi (CH₃)₂(t-butyl);

wherein R₃ is =O, OH, H, O(C₁–C₄ alkyl), OC(O)(C₁–C₂ alkyl), or OC(O)benzyl;

wherein R₅ is H, halogen, OH, or —OC₍₂₋₆₎ alkyl group;

wherein R₆ is H, =O, OH, OCH₃, CN, OC(O)H, OC(O)(C₁–C₄ alkyl), or OC(O)benzyl;

wherein R₇ is H, =O, OH, OCH₃, or halogen;

wherein R₈ and R₉ are independently H, CH₃, OCH₃, OC₂H₅, Br, F, or CF₃; and wherein the chiral center marked * has the R or the S configuration.

37. The compound of claim 36, having the formula:

[Chemical structure diagram with substituents OR₁, R₃, H, Me, MeO, OMe, R₄O, OMe, Me, R₅, NMe, R₇, R₆, R₂, H, N, with chiral center marked *]

wherein R₁ and R₄ is H, a $C_1$ to $C_4$ alkyl group, C(O)($C_1$–$C_4$ alkyl) or additionally R₄ is benzyl;

wherein R₂ is H, OH, O($C_1$–$C_4$ alkyl), O-benzyl, OC(O)H, OC(O)($C_1$–$C_4$ alkyl), OC(O)benzyl, or OSi(CH₃)₂(t-butyl);

wherein R₃ is =O, OH, H, O($C_1$–$C_4$ alkyl), OC(O)($C_1$–$C_2$ alkyl), or OC(O)benzyl;

wherein R₅ is H, halogen, OH, or —OC$_{(2-6)}$ alkyl group;

wherein R₆ is H, =O, OH, OCH₃, CN, OC(O)H, OC(O)($C_1$–$C_4$ alkyl), or OC(O)benzyl;

wherein R₇, is H, =O, OH, OCH₃, or halogen; and wherein the chiral center marked * has the R or the S configuration.

38. The compound of claim 37, wherein R₁ is H, R₂ is OH, R₃ is H, R₄ is H, R₅ is H, R₆ is =O, and R₇ is H.

39. The compound of claim 37, wherein R₃ is H, R₄ is CH₃, R₅ is OCH₃, and R₇ is H.

40. The compound of claim 39, wherein R₂ is OH.

41. The compound of claim 40, wherein R₆ is H and R₁ is CH₃.

42. The compound of claim 40, wherein R₆ is =O and R₁ is H.

43. A compound having the formula:

[Chemical structure diagram with substituents OR₁, R₃, H, R₁₀, R₄O, OR₁₂, R₁₁, R₅, NMe, R₇, R₆, R₂, H, R₈, R₉, N, with chiral center marked *]

wherein R₁ and R₄ is H, a $C_1$ to $C_4$ alkyl group, C(O)($C_1$–$C_4$ alkyl) or additionally R₄ is benzyl;

wherein R₂ is H, OH, O($C_1$–$C_4$ alkyl), O-benzyl, OC(O)H, OC(O)($C_1$–$C_4$ alkyl), OC(O)benzyl, or OSi(CH₃)₂(t-butyl);

wherein R₃ is H;

wherein R₅ is H, halogen, OH, or —OC$_{(1-6)}$ alkyl group;

wherein R₆ is H, =O, OH, OCH₃, CN, OC(O)H, OC(O)($C_1$–$C_4$ alkyl), or OC(O)benzyl;

wherein R₇, is H, =O, OH, OCH₃, or halogen;

wherein R₈ and R₉ are independently H, CH₃, OCH₃, OC₂H₅, Br, F, or CF₃;

wherein R₁₀ and R₁₁ are independently CH₃, OCH₃, OC₂H₅, SCH₃, or SC₂H₅;

wherein R₁₂ is H, a $C_1$ to $C_4$ alkyl group, or C(O)($C_1$–$C_4$ alkyl); and wherein the chiral center marked * has the R or the S configuration.

* * * * *